(12) United States Patent
Siegel et al.

(10) Patent No.: US 7,399,774 B2
(45) Date of Patent: Jul. 15, 2008

(54) 6-SUBSTITUTED NICOTINAMIDE DERIVATIVES AS OPIOID RECEPTOR ANTAGONISTS

(75) Inventors: Miles Goodman Siegel, Indianapolis, IN (US); Russell Dean Stucky, Indianapolis, IN (US); Kumiko Takeuchi, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 579 days.

(21) Appl. No.: 10/546,521

(22) PCT Filed: Feb. 25, 2004

(86) PCT No.: PCT/US2004/003360

§ 371 (c)(1),
(2), (4) Date: Aug. 19, 2005

(87) PCT Pub. No.: WO2004/080968

PCT Pub. Date: Sep. 23, 2004

(65) Prior Publication Data

US 2006/0205715 A1    Sep. 14, 2006

Related U.S. Application Data

(60) Provisional application No. 60/453,414, filed on Mar. 7, 2003.

(51) Int. Cl.
  *C07D 211/72* (2006.01)
  *A61K 31/44* (2006.01)

(52) U.S. Cl. .................................... 514/350; 546/298
(58) Field of Classification Search ................ 546/298; 514/350
See application file for complete search history.

(56) References Cited

FOREIGN PATENT DOCUMENTS

| EP | 0 827 746 | 11/1998 |
|---|---|---|
| WO | WO 95/35316 | 12/1995 |
| WO | WO 96/36620 | 11/1996 |
| WO | WO 99/33806 | 7/1999 |
| WO | WO 01/46198 | 6/2001 |
| WO | WO 02/078693 | 10/2002 |
| WO | WO 2004/026305 | 4/2004 |

*Primary Examiner*—Zinna N Davis
(74) *Attorney, Agent, or Firm*—John C. Demeter; Francis O. Ginah

(57) ABSTRACT

A compound of the formula (I) or a pharmaceutically acceptable salt, enantiomer, racemate, diastereomers or mixtures thereof, or a solvate thereof, formulations and methods of use thereof, as opioid receptor antagonists are disclosed wherein the variables are as described herein.

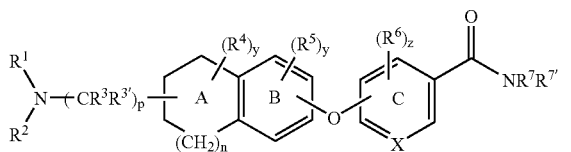

(I)

2 Claims, No Drawings

6-SUBSTITUTED NICOTINAMIDE DERIVATIVES AS OPIOID RECEPTOR ANTAGONISTS

This is the national phase application, under 35 USC 371, for PCT/US2004/003360, filed 24 Feb. 2004, which, claims the benefit, under 35 USC 119(e), of U.S. provisional application No. 60/453,414, filed 7 Mar. 2003.

The present invention is in the field of medicinal chemistry. The invention relates specifically to compounds useful as opioid antagonists, methods of treatment, methods of using, and pharmaceutical compositions thereof.

BACKGROUND

Three types of opioid receptors, mu, kappa, and delta opioid receptors are generally reported. Recent evidence points to the interactions between receptor dimer combinations of mu, kappa and/or delta receptors (called heterodimers) as also contributing to opioid activity. Opioid receptors and their normal regulation or lack thereof, has been implicated in disease states including irritable bowel syndrome, nausea, vomiting, pruritic dermatoses, depression, smoking and alcohol addiction, sexual dysfunction, stroke and trauma in animals. Therefore it is not surprising that the ability to antagonistically bind opioid receptors has been shown to produce ameliorative, preventative and/or treatment effects in animals including humans afflicted with one or more of these disease states.

More recently, antagonists of the opioid receptors have been found to increase metabolic energy consumption, and reduction of weight in obese rats while maintaining muscle mass. These findings indicate that an effective opioid antagonist may be useful in preventing, treating and or ameliorating the effect of obesity. Considering the percentage of the population that is obese in Western societies and the indirect costs associated with treating the effects and symptoms of obesity and Related Diseases, the impact of these findings cannot be overstated.

Though many opioid antagonists have been disclosed, the search continues for alternative and/or improved or more effective antagonists having an overall benefit to the patient with little or no major side effects. U.S. Pat. No. 4,891,379 discloses phenylpiperidine opioid antagonists useful for the treatment of diabetes and obesity. Clinical development of a compound claimed in U.S. Pat. No. 4,191,771 was discontinued due to poor oral bioavailability characteristics. Bicyclic analogs of phenyl piperidine have been prepared and reported as opioid antagonists by Wentland, et al., Biorganic and Medicinal Chemistry Letters 11 (2001) 623-626; see also Wentland, et al., Biorganic and Medicinal Chemistry Letters 11 (2001) 1717-1721. Finally, European Patent application number EP 1 072592A2 filed May 18, 2000, discloses phenylpiperidine compounds of formula I

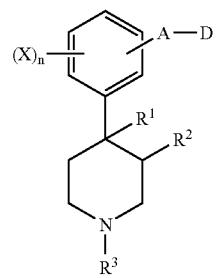

wherein A, D, $R^1$, $R^2$, $R^3X$, and n have meanings given in the description, which are useful in the prophylaxis and in the treatment of diseases mediated by opioid receptors such as pruritus.

In spite of these and other disclosures of compounds useful as opioid receptor antagonists, there remains an unmet medical need for safe, effective and/or alternate treatment or prophylaxis of diseases associated with opioid receptors, particularly obesity and Related Diseases.

SUMMARY OF THE INVENTION

The present invention provides a compound of the formula (I)

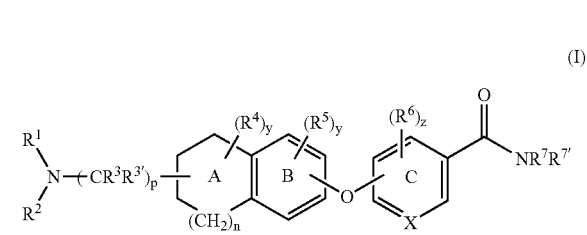

or a pharmaceutically acceptable salt, solvate, enantiomer, racemate, diastereomer or a mixture thereof, wherein X is C or N;

p is 0, 1, 2, or 3;

n is 0, 1, or 2;

$R^1$ and $R^2$ are independently selected from hydrogen, $C_1$-$C_8$alkyl, $C_2$-$C_8$alkenyl, $C_2$-$C_8$alkynyl, $C_1$-$C_{10}$alkylaryl, $C_4$-$C_{10}$alkylcycloalkane, $C_1$-$C_8$alkoxyalkyl, $(CH_2)_nC(O)OR^8$, $(CH_2)_nC(O)R^8$, $(CH_2)_mC(O)NR^8R^8$, and $(CH_2)_mNSO_2R^8$; wherein each of the alkyl, alkenyl, and aryl groups are optionally substituted with one to five groups independently selected from $C_1$-$C_8$alkyl, $C_2$-$C_8$alkenyl, phenyl, $C_1$-$C_8$alkylaryl, and $C_4$-$C_{10}$alkylcycloalkane, and wherein $R^1$ and $R^2$ may optionally combine with each other to form a 4, 5, 6, or 7-member nitrogen-containing heterocycle which nitrogen-containing heterocycle may further have substituents selected from the group consisting of oxo, amino, $C_1$-$C_8$ alkyl, $C_2$-$C_8$alkenyl, $C_2$-$C_8$alkynyl, phenyl, $C_1$-$C_8$alkylaryl, $C(O)C_1$-$C_8$alkyl, $CO(O)C_1$-$C_8$alkyl, halo, $C_1$-$C_8$haloalkyl;

$R^3$ and $R^{3'}$ are each independently selected from Hydrogen, $C_1$-$C_8$alkyl, $C_2$-$C_8$alkenyl, $C_2$-$C_8$alkynyl, phenyl, aryl, and $C_1$-$C_8$alkylaryl;

$R^4$, $R^5$, and $R^6$ are each independently selected from $C_1$-$C_8$alkyl, $C_2$-$C_8$alkenyl, $C_2$-$C_8$alkynyl, $C_1$-$C_8$alkoxy, halo, $C_1$-$C_8$haloalkyl, phenyl, aryl, $C_1$-$C_8$alkylaryl, $(CH_2)_m$ $NSO_2C_1$-$C_8$alkyl, $(CH_2)_mNSO_2$phenyl, $(CH_2)_m$ $NSO_2$aryl, —$C(O)C_1$-$C_8$alkyl, or —$C(O)OC_1$-$C_8$alkyl; wherein each $R^4$, $R^5$, and $R^6$ is attached to its respective ring only at carbon atoms, and wherein y is 0, 1, 2, or 3; and wherein z is 0, 1, 2, or 3

$R^7$ and $R^{7'}$ are each independently selected from hydrogen, $C_1$-$C_8$alkyl, $C_2$-$C_8$alkenyl, $C_2$-$C_8$ alkynyl, $C(O)C_1$-$C_8$alkyl, hydroxy, $C_1$-$C_8$alkoxy, $SO_2C_1$-$C_8$alkyl, $SO_2C_1$-$C_8$alkylaryl, $SO_2C_1$-$C_8$alkylheterocyclic, aryl, $C_1$-$C_8$alkylaryl, $C_3$-$C_7$cycloalkane, $C_1$-$C_{10}$ alkylcycloalkane, $(CH_2)_nC(O)OR^8$, $(CH_2)_nC(O)R^8$, $(CH_2)_mC(O)NR^8R^8$, and $(CH_2)_mNSO_2R^8$; wherein the alkyl, alkenyl, and aryl groups are each optionally substituted with one to five groups independently selected from $C_1$-$C_8$alkyl, $C_2$-$C_8$alkenyl, phenyl, and $C_1$-$C_8$alkylaryl; and wherein $R^7$ and R$^{7'}$ may independently combine with each other, and with the nitrogen atom to which they are attached to form a 4, 5, 6, or 7-member nitrogen containing heterocycle which nitrogen containing heterocycle may further have substituents selected from the group consisting of oxo, amino, $C_1$-$C_8$alkyl, $C_2$-$C_8$alkenyl, $C_2$-$C_8$alkynyl, phenyl, $C_1$-$C_8$alkylaryl, $C(O)C_1$-$C_8$alkyl, $CO(O)C_1$-$C_8$alkyl, hydroxy, $C_1$-$C_8$alkoxy, halo, and haloalkyl;

R$^8$ is hydrogen, $C_1$-$C_8$alkyl, $C_2$-$C_8$alkenyl, $C_5$-$C_8$alkylaryl, $(CH_2)_m NSO_2 C_1$-$C_8$alkyl, $(CH_2)_m NSO_2$Phenyl, $(CH_2)_m NSO_2$aryl, —$C(O)C_1$-$C_8$alkyl, or —$C(O)OC_1$-$C_8$alkyl; and m is 1,2.

The present invention also provides a method of using a compound of formula I for the prevention, treatment and/or amelioration of the symptoms of obesity and Related Diseases comprising administering a therapeutically effective amount of a compound of formula I to a patient in need thereof.

The present invention also provides a pharmaceutical formulation comprising a compound of formula I in association with a carrier, diluent and/or excipient.

The present invention relates to the use of a compound of formula I for the treatment and/or prophylaxis of obesity and Related Diseases including eating disorders (bulima, anorexia nervosa, etc.), diabetes, diabetic complications, diabetic retinopathy, sexual/reproductive disorders, depression, anxiety, epileptic seizure, hypertension, cerebral hemorrhage, congestive heart failure, sleeping disorders, atherosclerosis, rheumatoid arthritis, stroke, hyperlipidemia, hypertriglycemia, hyperglycemia, and hyperlipoproteinenamia, substance abuse, drug overdose, compulsive behavior disorders (such as paw licking in dog), addictive behaviors such as gambling.

The present invention provides a compound of formula (I) useful for the manufacture of a medicament for the treatment, prevention and/or amelioration of symptoms associated with obesity and Related Diseases.

In another embodiment, the present invention provides a compound of formula I or a pharmaceutically acceptable salt, solvate, enantiomer, racemate, diastereomer or a mixture thereof, useful as an appetite suppressant.

DETAILED DESCRIPTION OF THE INVENTION

As used herein, the term "patient" includes human and non-human animals such as companion animals (dogs and cats and the like) and livestock animals.

The preferred patient or subject of treatment, amelioration and/or prevention of obesity and Related Diseases is a human.

The terms "treating" and "treat", as used herein, include their generally accepted meanings, i.e., preventing, prohibiting, restraining, alleviating, ameliorating, slowing, stopping, or reversing the progression or severity of a pathological condition, or sequela thereof, described herein.

The terms "ameliorating" "preventing", "prevention of", "prophylaxis", "prophylactic" and "prevent" are used herein interchangeably and refer to reducing the severity of the symptoms associated with obesity and Related Diseases in a patient afflicted with same, or reducing the likelihood that the recipient of a compound of formula I will incur or develop any of the pathological conditions, or sequela thereof, described herein.

As used herein, the term "effective amount" is synonymous with "effective dose" and means an amount of a compound of formula I that is sufficient in one or more administrations for preventing, ameliorating or treating a condition, or detrimental effects thereof, herein described, or an amount of a compound of formula I that is sufficient for antagonizing the opioid receptors to achieve the objectives of the invention.

The term "pharmaceutically acceptable" is used herein as an adjective and means substantially non-deleterious to the recipient patient.

The term "Active Ingredient" as used herein means a compound of formula I or a combination of compounds of formula I or a combination of a compound of formula I and a co-antagonist of the opioid receptor.

The term "formulation", as in pharmaceutical formulation, or "pharmaceutical composition" is intended to encompass a product comprising the Active Ingredient and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical formulations of the present invention encompass any effective composition made by admixing a compound of the present invention and a pharmaceutical carrier. The pharmaceutical formulations of the present invention also encompass a compound of the formula I and a pharmaceutically acceptable co-antagonist of the opioid receptors useful for the treatment and/or prevention of obesity and/or Related Diseases.

The term "Related Diseases" as used herein refers to such symptoms, diseases or conditions caused by, exacerbated by, induced by or adjunct to the condition of being obese. Such diseases, conditions and/or symptoms include but are not limited to eating disorders (bulimia, anorexia nervosa, etc.), diabetes, diabetic complications, diabetic retinopathy, sexual/reproductive disorders, depression (particularly that induced by the awareness and loss of self esteem associated with obesity), anxiety, epileptic seizure, hypertension, cerebral hemorrhage, congestive heart failure, sleeping disorders, atherosclerosis, rheumatoid arthritis, stroke, hyperlipidemia, hypertriglycemia, hyperglycemia, and hyperlipoproteinenamia.

The term "suitable solvent" refers to any solvent, or mixture of solvents, inert to the ongoing reaction that sufficiently solubilizes the reactants to afford a medium within which the desired reaction is reasonably effected.

The term "mutual solvent" means a solvent that is used to dissolve sufficiently, two or more components of a reaction or mixture separately prior to reaction or mixing, that is a solvent common to more than one reagents or components of a mixture.

The term "nitrogen containing heterocycle" refers to a monocycle which is a 4, 5, 6, or 7-member ring containing 1, 2 or 3 nitrogen atoms in addition to the carbon atoms completing the ring size, or a combination of 1 nitrogen atom and 1, or 2 atoms selected from oxygen, and sulfur in addition to the appropriate number of carbon atoms completing the ring size. A nitrogen containing heterocycle as used here may have 0, 1 or 3 double bonds.

The term $C_1$-$C_8$alkyl refers to and includes all groups, structural isomers and/or homologues of alkyl groups having from 1 to 8 carbon atoms. When the term $C_1$-$C_8$alkyl precedes or prefixes another group, the term $C_1$-$C_8$alkyl, only limits the number of carbon atoms in the alkyl component. For example $C_1$-$C_8$alkyaryl means an aryl group having a $C_1$-$C_8$alkyl group substituent such that the number of carbon atoms in the group $C_1$-$C_8$alkylaryl is effectively the number of carbon atoms in the aryl group plus the number of carbon atoms in the $C_1$-$C_8$alkyl group. Similarly, the term $C_1$-$C_8$alkylcycloalkane, refers to a cycloalkane group having a $C_1$-$C_8$alkyl substituent, and wherein the entire group $C_1$-$C_8$alkylcycloalkane may itself be a substituent attached at either the alkyl group or the cycloalkyl group to a substrate.

The term "cycloalkane" means a cyclic alkyl group having from 3 to 8 carbon atoms i.e. from cyclopropane to cyclooctane unless otherwise indicated.

The term "halo" as used herein refers to a halogen including fluorine, chlorine, bromine or iodine.

As used herein the terms "alkenyl" refers to straight or branched carbon atoms having 1 or 2 carbon-carbon double bonds.

As used herein the terms "alkynyl" refers to straight or branched carbon atoms having 1 or 2 carbon-carbon triple bonds.

As used herein the term "alkoxy" refers to the group "O-alkyl" wherein alkyl is as indicated for the specific situation or as defined previously defined previously.

The term "aryl" as used herein refers to compounds or groups having the Huckel 4n+2 pi electron arrangement and includes phenyl, benzyl, naphthyl, but excludes carbazoles.

As used herein, the term "protecting group" refers to a group useful for masking reactive sites in a molecule to enhance the reactivity of another group or allow reaction at another desired site or sites following which the protecting group may be removed. Protecting groups are usually used to protect or mask groups including but not limited to —OH, —NH, and —COOH. Suitable protecting groups are known to one of skill in the art and are described in *Protecting groups in Organic Synthesis*, 3$^{rd}$ edition, Greene, T. W.; Wuts, P. G. M. Eds.; John Wiley and Sons, New York, 1999.

As used herein, the term "solvate" is a form of the compound of the invention wherein a crystal or crystals of a compound of the invention have been formed from a stoichiometric or non-stoichiometric amount of the compound of formula 1 and a solvent. Typical solvating solvents include for example, water, methanol, ethanol, acetone and dimethylformamide.

In those instances where a compound of the invention possesses acidic or basic functional groups, various salts may be formed which are more water soluble and/or more physiologically suitable than the parent compound. Representative pharmaceutically acceptable salts include but are not limited to the alkali and alkaline earth salts such as lithium, sodium, potassium, calcium, magnesium, aluminum and the like. Salts are conveniently prepared from the free acid by treating the acid in solution with a base or by exposing the acid to an ion-exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1-19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, hydrobromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, hydrochloride, hydroxynaphthoate, hydroiodide, isothionate, lactate, lactobionate, laurate, malate, malseate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

A compound of the invention as illustrated by formula I may occur as any one of its positional isomers, stereo chemical isomers or regioisomers, all of which are objects of the invention. Certain compounds of the invention may possess one or more chiral centers, and thus, may exist in optically active forms. Likewise, when the compounds contain an alkenyl or alkenylene group, there exist the possibility of cis- and trans-isomeric forms of the compounds. The R- and S-isomers and mixtures thereof, including racemic mixtures as well as mixtures of enantiomers or cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a racemic mixture may be reacted with a single enantiomer of some other compound i.e. a chiral resolving agent. This changes the racemic form into a mixture of stereoisomers and diastereomers, because they have different melting points, different boiling points, and different solubilities and can be separated by conventional means, such as, for example, crystallization or chromatography.

The compound(s) of the present invention have shown inhibition of orexigenic effects, and are thus useful as appetite suppressants either as a single therapy or in conjunction with exercise and/or other effective appetite suppressing or weight loss medications.

The efficacy of the compounds of the present invention has been shown by their activity in several biological activity models including an SPA GTP-gamma-S binding assay and other assays.

PREFERRED EMBODIMENTS OF THE INVENTION

A compound of formula I preferably exists as a pharmaceutically acceptable salt. More preferred is the hydrochloride, or the bisulfate salt, or the oxalic acid salt of the compound of formula I.

Though the groups $R^4$, $R^5$ and $R^6$ may exist as multiple substituents on their respective ring substrates, a preferred embodiment of the invention involves compounds wherein each of $R^4$, $R^5$, and $R^6$ are absent, or are singly or doubly substituted on their respective ring substrates. Preferred embodiments of the compound of formula I include the substructures Ia, Ib and Ic as shown below:

(Ia)

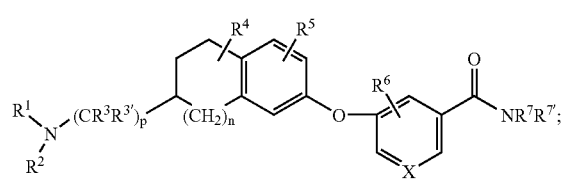

-continued

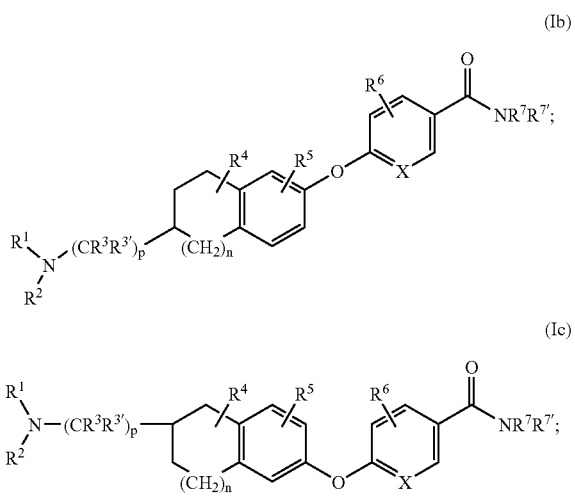

For the groups R¹ and R²

Preferred R¹ and R² groups are independently selected from the group consisting of Hydrogen, methyl, ethyl, propyl, pentyl, and isopropyl. Also preferred are R¹ and R² groups independently selected from the group consisting of:

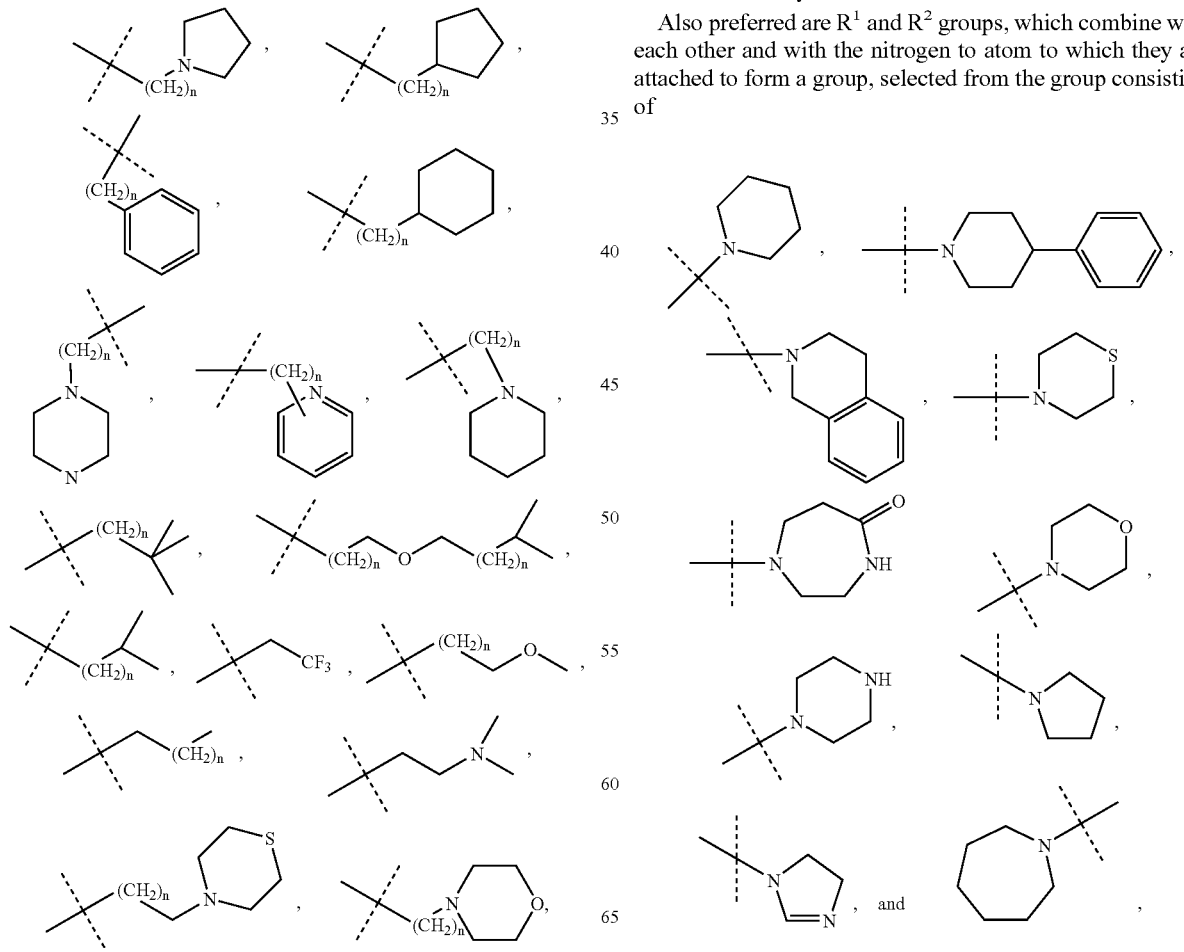

each of which is optionally substituted with a group selected from the group consisting of halogen, $C_1$-$C_8$ alkyl, $C_1$-$C_8$ haloalkyl, $C_1$-$C_8$ thioalkyl, $C_1$-$C_8$ alkylamino, phenyl; $C_1$-$C_8$ alkylsubstituted phenyl, $C_4$-$C_8$ heterocycle or $C_1$-$C_4$ alkyl heterocycle; or combine with a group selected from $C_1$-$C_8$ alkyl, halogen, $C_1$-$C_8$ haloalkyl, $C_1$-$C_8$ thioalkyl, $C_1$-$C_8$ alkylamino, phenyl, $C_1$-$C_8$ alkylsubstituted phenyl, $C_4$-$C_8$ heterocycle or $C_1$-$C_4$ alkyl heterocycle to form a substituted or unsubstituted bicycle.

Also preferred are R¹ and R² groups, which combine with each other and with the nitrogen to atom to which they are attached to form a group, selected from the group consisting of each of which is optionally substituted with a group selected from the group consisting of halogen, $C_1$-$C_8$ alkyl, $C_1$-$C_8$ haloalkyl, $C_1$-$C_8$ thioalkyl, $C_1$-$C_8$ alkylamino, phenyl, $C_1$-$C_8$ alkylsubstituted phenyl, $C_4$-$C_8$ heterocycle or $C_1$-$C_4$ alkylheterocycle.

Preferred $R^3$ and $R^{3'}$ Groups

A preferred $R^3$ is Hydrogen. A preferred $R^{3'}$ group is selected from hydrogen, methyl, ethyl, propyl, isopropyl, phenyl and benzyl.

Preferred $R^4$ Groups

A preferred $R^4$ group is selected from the group consisting of halo, $C_1$-$C_5$ alkyl, $C_1$-$C_5$ haloalkyl, $C_1$-$C_5$ alkoxy, $C_1$-$C_5$ alkylamino, phenyl, $C_1$-$C_5$ alkylphenyl, $C_1$-$C_5$ alkylcycloalkyl, and $C_1$-$C_5$ thioalkyl. More preferred is a $R^4$ group selected from the group consisting of methyl, ethyl, isopropyl, bromo, chloro, fluoro, trifluoromethyl, methoxy, ethoxy, thiomethyl, phenyl, and benzyl. A most preferred $R^4$ group is selected from the group consisting of methyl, ethyl, isopropyl, fluoro, chloro, bromo, trifluoromethyl, methoxy, ethoxy, propoxy, isopropoxy, and benzyl.

Preferred $R^5$ Groups

A preferred $R^5$ group is selected from the group consisting of halo, $C_1$-$C_5$ alkyl, $C_1$-$C_5$ haloalkyl, $C_1$-$C_5$ alkoxy, $C_1$-$C_5$ alkylamino, phenyl, $C_1$-$C_5$ alkylphenyl, C1-C5 alkylcycloalkyl, and $C_1$-$C_5$ thioalkyl. More preferred is an $R^5$ group selected from the group consisting of methyl, ethyl, isopropyl, bromo, chloro, fluoro, trifluoromethyl, methoxy, ethoxy, thiomethyl, phenyl, and benzyl. A most preferred $R^5$ group is selected from the group consisting of methyl, ethyl, isopopropyl, fluoro, bromo, chloro, trifluoromethyl, methoxy, ethoxy, Preferred $R^6$ Groups A preferred $R^6$ group is selected from the group consisting of halo, $C_1$-$C_5$ alkyl, $C_1$-$C_5$ haloalkyl, $C_1$-$C_5$ alkoxy, $C_1$-$C_5$ alkylamino, phenyl, $C_1$-$C_5$ alkylphenyl, $C_1$-$C_5$ alkylcycloalkyl, and $C_1$-$C_5$ thioalkyl. More preferred is an $R^6$ group selected from the group consisting of methyl, ethyl, isopropyl, bromo, chloro, fluoro, trifluoromethyl, methoxy, ethoxy, thiomethyl, phenyl, and benzyl. A most preferred $R^6$ group is selected from the group consisting of methyl, ethyl, isopropyl, fluoro, bromo, chloro, trifluoromethyl, methoxy, ethoxy, trifluoromethoxy, and benzyl.

Though the groups $R^4$, $R^5$ and $R^6$ may exist as multiple substituents on their respective ring substrates, a preferred embodiment of the invention involves compounds wherein each of $R^4$, $R^5$ and $R^6$ is absent, or is singly or doubly substituted on its respective ring substrate. In any event the requisite number of hydrogen atoms on the respective ring to satisfy valency requirements is implied.

Preferred $R^7$ and $R^{7'}$ Groups

Preferred are $R^7$ and $R^{7'}$ groups independently selected from the group consisting of Hydrogen, methyl, ethyl, propyl, pentyl, isopropyl, phenyl and benzyl,

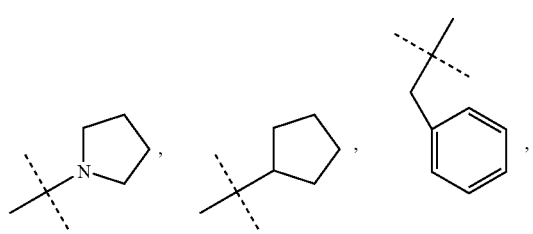

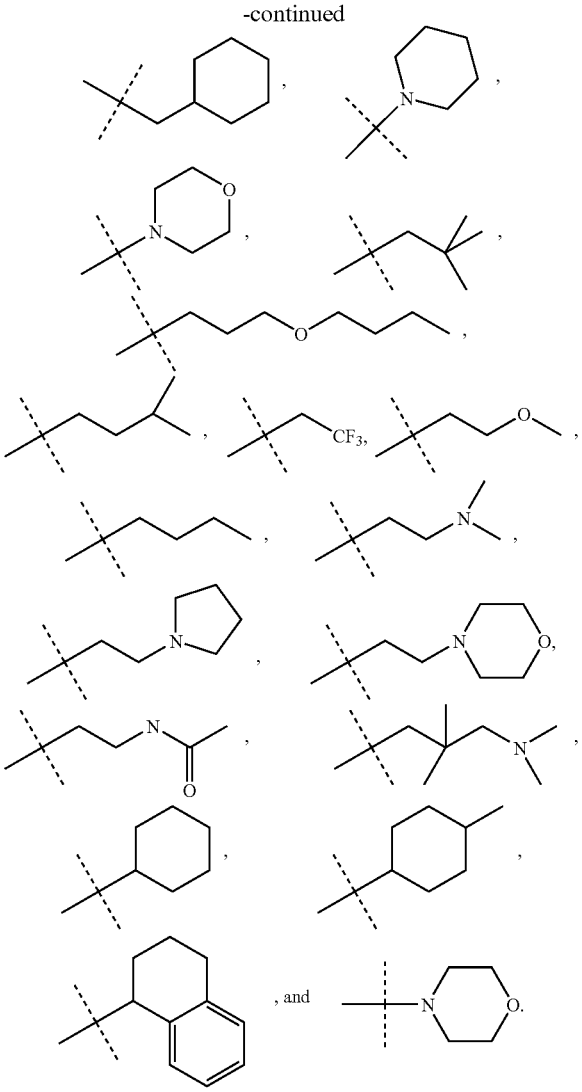

Most preferred $R^7$ and $R^{7'}$ are hydrogen atoms.

Preferred values for n and m, p, and z

A preferred value for n is 0, 1, or 2.

A preferred value for m is 1 or 2.

A preferred value for p is 0, 1, 2, or 3.

A preferred value for y or Z is 0, or 1 or 2.

Preferred A and C Rings

A preferred A ring is cyclopentane, or cyclohexane. A preferred C ring is phenyl, or pyridine Preferred compounds of the invention include but are not limited to compounds selected from the group consisting of
6-(8-Pentylamino-5,6,7,8-tetrahydro-naphthalen-2-yloxy)-nicotinamide,
6-(5-Pentylamino-5,6,7,8-tetrahydro-naphthalen-2-yloxy)-nicotinamide,
6-(5-Pentylamino-5,6,7,8-tetrahydro-naphthalen-1-yloxy)-nicotinamide,
6-(1-Pentylamino-indan-5-yloxy)-nicotinamide,
6-(1-Pentylamino-indan-4-yloxy)-nicotinamide,
6-(8-Benzylamino-5,6,7,8-tetrahydro-naphthalen-2-yloxy)-nicotinamide,
6-(5-Benzylamino-5,6,7,8-tetrahydro-naphthalen-2-yloxy)-nicotinamide, 6-(5-Benzylamino-5,6,7,8-tetrahydro-naphthalen-1-yloxy)-nicotinamide,
6-(1-Benzylamino-indan-4-yloxy)-nicotinamide,
6-(8-Phenethylamino-5,6,7,8-tetrahydro-naphthalen-2-yloxy)-nicotinamide,
6-(5-Phenethylamino-5,6,7,8-tetrahydro-naphthalen-2-yloxy)-nicotinamide,
6-(5-Phenethylamino-5,6,7,8-tetrahydro-naphthalen-1-yloxy)-nicotinamide,
6-(1-Phenethylamino-indan-4-yloxy)-nicotinamide,
6-{8-[2-(3-Fluoro-phenyl)-ethylamino]-5,6,7,8-tetrahydro-naphthalen-2-yloxy}-nicotinamide,
6-{5-[2-(3-Fluoro-phenyl)-ethylamino]-5,6,7,8-tetrahydro-naphthalen-2-yloxy}-nicotinamide,
6-{5-[2-(3-Fluoro-phenyl)-ethylamino]-5,6,7,8-tetrahydro-naphthalen-1-yloxy}-nicotinamide,
6-{3-[2-(3-Fluoro-phenyl)-ethylamino]-indan-5-yloxy}-nicotinamide,
6-{1-[2-(3-Fluoro-phenyl)-ethylamino]-indan-5-yloxy}-nicotinamide,
6-{1-[2-(3-Fluoro-phenyl)-ethylamino]-indan-4-yloxy}-nicotinamide,
6-[8-(3-Methyl-butylamino)-5,6,7,8-tetrahydro-naphthalen-2-yloxy]-nicotinamide,
6-[5-(3-Methyl-butylamino)-5,6,7,8-tetrahydro-naphthalen-2-yloxy]-nicotinamide,
6-[5-(3-Methyl-butylamino)-5,6,7,8-tetrahydro-naphthalen-1-yloxy]-nicotinamide,
6-[8-(4-Methyl-cyclohexylamino)-5,6,7,8-tetrahydro-naphthalen-2-yloxy]-nicotinamide,
6-[5-(4-Methyl-cyclohexylamino)-5,6,7,8-tetrahydro-naphthalen-2-yloxy]-nicotinamide,
6-[5-(4-Methyl-cyclohexylamino)-5,6,7,8-tetrahydro-naphthalen-1-yloxy]-nicotinamide,
6-[1-(4-Methyl-cyclohexylamino)-indan-5-yloxy]-nicotinamide,
6-[1-(4-Methyl-cyclohexylamino)-indan-4-yloxy]-nicotinamide,
6-(7-Pentylamino-5,6,7,8-tetrahydro-naphthalen-2-yloxy)-nicotinamide,
6-(6-Pentylamino-5,6,7,8-tetrahydro-naphthalen-2-yloxy)-nicotinamide,
6-(6-Pentylamino-5,6,7,8-tetrahydro-naphthalen-1-yloxy)-nicotinamide,
6-(7-Pentylamino-5,6,7,8-tetrahydro-naphthalen-1-yloxy)-nicotinamide,
6-(7-Benzylamino-5,6,7,8-tetrahydro-naphthalen-2-yloxy)-nicotinamide,
6-(6-Benzylamino-5,6,7,8-tetrahydro-naphthalen-2-yloxy)-nicotinamide,
6-(6-Benzylamino-5,6,7,8-tetrahydro-naphthalen-1-yloxy)-nicotinamide,
6-(7-Benzylamino-5,6,7,8-tetrahydro-naphthalen-1-yloxy)-nicotinamide,
6-(7-Phenethylamino-5,6,7,8-tetrahydro-naphthalen-2-yloxy)-nicotinamide,
6-(6-Phenethylamino-5,6,7,8-tetrahydro-naphthalen-2-yloxy)-nicotinamide,
6-(6-Phenethylamino-5,6,7,8-tetrahydro-naphthalen-1-yloxy)-nicotinamide,
6-(7-Phenethylamino-5,6,7,8-tetrahydro-naphthalen-1-yloxy)-nicotinamide,
6-{7-[2-(3-Fluoro-phenyl)-ethylamino]-5,6,7,8-tetrahydro-naphthalen-2-yloxy}-nicotinamide,
6-{6-[2-(3-Fluoro-phenyl)-ethylamino]-5,6,7,8-tetrahydro-naphthalen-2-yloxy}-nicotinamide,
6-{6-[2-(3-Fluoro-phenyl)-ethylamino]-5,6,7,8-tetrahydro-naphthalen-1-yloxy}-nicotinamide,
6-{7-[2-(3-Fluoro-phenyl)-ethylamino]-5,6,7,8-tetrahydro-naphthalen-1-yloxy}-nicotinamide,
6-[7-(3-Methyl-butylamino)-5,6,7,8-tetrahydro-naphthalen-2-yloxy]-nicotinamide,
6-[6-(3-Methyl-butylamino)-5,6,7,8-tetrahydro-naphthalen-2-yloxy]-nicotinamide,
6-[6-(3-Methyl-butylamino)-5,6,7,8-tetrahydro-naphthalen-1-yloxy]-nicotinamide,
6-[7-(3-Methyl-butylamino)-5,6,7,8-tetrahydro-naphthalen-1-yloxy]-nicotinamide,
6-[7-(4-Methyl-cyclohexylamino)-5,6,7,8-tetrahydro-naphthalen-2-yloxy]-nicotinamide,
6-[6-(4-Methyl-cyclohexylamino)-5,6,7,8-tetrahydro-naphthalen-1-yloxy]-nicotinamide,
6-[7-(4-Methyl-cyclohexylamino)-5,6,7,8-tetrahydro-naphthalen-1-yloxy]-nicotinamide,
6-[7-(3-Phenyl-propylamino)-5,6,7,8-tetrahydro-naphthalen-2-yloxy]-nicotinamide,
6-[6-(3-Phenyl-propylamino)-5,6,7,8-tetrahydro-naphthalen-2-yloxy]-nicotinamide,
6-[6-(3-Phenyl-propylamino)-5,6,7,8-tetrahydro-naphthalen-1-yloxy]-nicotinamide,
6-[7-(3-Phenyl-propylamino)-5,6,7,8-tetrahydro-naphthalen-1-yloxy]-nicotinamide,
6-[5-(2-Methylsulfanyl-ethylamino)-5,6,7,8-tetrahydro-naphthalen-2-yloxy]-nicotinamide,
6-[1-(2-Methylsulfanyl-ethylamino)-indan-5-yloxy]-nicotinamide,
6-{5-[2-(3-Methoxy-phenyl)-ethylamino]-5,6,7,8-tetrahydro-naphthalen-2-yloxy}-nicotinamide,
6-{1-[2-(3-Methoxy-phenyl)-ethylamino]-indan-5-yloxy}-nicotinamide,
6-[5-(2-Dimethylamino-ethylamino)-5,6,7,8-tetrahydro-naphthalen-2-yloxy]-nicotinamide,
6-[1-(2-Dimethylamino-ethylamino)-indan-5-yloxy]-nicotinamide,
6-[5-(2-Pyrrolidin-1-yl-ethylamino)-5,6,7,8-tetrahydro-naphthalen-2-yloxy]-nicotinamide,
6-[1-(2-Pyrrolidin-1-yl-ethylamino)-indan-5-yloxy]-nicotinamide,
6-[5-(2-Pyridin-2-yl-ethylamino)-5,6,7,8-tetrahydro-naphthalen-2-yloxy]-nicotinamide,
6-[1-(2-Pyridin-2-yl-ethylamino)-indan-5-yloxy]-nicotinamide,
6-[5-(2-Morpholin-4-yl-ethylamino)-5,6,7,8-tetrahydro-naphthalen-2-yloxy]-nicotinamide,
6-[1-(2-Morpholin-4-yl-ethylamino)-indan-5-yloxy]-nicotinamide,
6-[1-(1,2-Diphenyl-ethylamino)-indan-5-yloxy]-nicotinamide,
6-{5-[2-(4-Fluoro-phenyl)-ethylamino]-5,6,7,8-tetrahydro-naphthalen-2-yloxy}-nicotinamide,
6-{1-[2-(4-Fluoro-phenyl)-ethylamino]-indan-5-yloxy}-nicotinamide,
6-[5-(2-Acetylamino-ethylamino)-5,6,7,8-tetrahydro-naphthalen-2-yloxy]-nicotinamide,
6-[1-(2-Acetylamino-ethylamino)-indan-5-yloxy]-nicotinamide,
6-{5-[2-(5-Fluoro-1H-indol-3-yl)-ethylamino]-5,6,7,8-tetrahydro-naphthalen-2-yloxy}-nicotinamide,
6-{1-[2-(5-Fluoro-1H-indol-3-yl)-ethylamino]-indan-5-yloxy}-nicotinamide,
3-[6-(5-Carbamoyl-pyridin-2-yloxy)-1,2,3,4-tetrahydro-naphthalen-1-ylamino]-propionic acid isopropyl ester, 3-[5-(5-Carbamoyl-pyridin-2-yloxy)-indan-1-ylamino]-propionic acid isopropyl ester,
6-(2-Pentylamino-indan-5-yloxy)-nicotinamide,
6-(2-Pentylamino-indan-4-yloxy)-nicotinamide,
6-(2-Benzylamino-indan-5-yloxy)-nicotinamide,
6-(2-Benzylamino-indan-4-yloxy)-nicotinamide,
6-[2-(3-Phenyl-propylamino)-indan-5-yloxy]-nicotinamide,
6-[2-(3-Phenyl-propylamino)-indan-4-yloxy]-nicotinamide,
6-[2-(3-Methyl-butylamino)-indan-5-yloxy]-nicotinamide,
6-[2-(3-Methyl-butylamino)-indan-4-yloxy]-nicotinamide,
6-[2-(2-Phenyl-propylamino)-indan-5-yloxy]-nicotinamide,
6-[2-(2-Phenyl-propylamino)-indan-4-yloxy]-nicotinamide,
6-(2-Phenethylamino-indan-5-yloxy)-nicotinamide,
6-(2-Phenethylamino-indan-4-yloxy)-nicotinamide,
6-{2-[(5-Fluoro-1H-indol-3-ylmethyl)-amino]-indan-5-yloxy}-nicotinamide,
6-{2-[(5-Fluoro-1H-indol-3-ylmethyl)-amino]-indan-4-yloxy}-nicotinamide,
6-[2-(3-Dimethylamino-2,2-dimethyl-propylamino)-indan-5-yloxy]-nicotinamide,
6-[2-(3-Dimethylamino-2,2-dimethyl-propylamino)-indan-4-yloxy]-nicotinamide,
6-{5-[(Benzo[b]thiophen-3-ylmethyl)-amino]-5,6,7,8-tetrahydro-naphthalen-2-yloxy}-nicotinamide,
6-{1-[(Benzo[b]thiophen-3-ylmethyl)-amino]-indan-5-yloxy}-nicotinamide,
6-[5-(2-Methoxy-ethylamino)-5,6,7,8-tetrahydro-naphthalen-2-yloxy]-nicotinamide,
6-[1-(2-Methoxy-ethylamino)-indan-5-yloxy]-nicotinamide,
6-{5-[2-(3-Trifluoromethyl-phenyl)-ethylamino]-5,6,7,8-tetrahydro-naphthalen-2-yloxy}-nicotinamide,
6-{1-[2-(3-Trifluoromethyl-phenyl)-ethylamino]-indan-5-yloxy}-nicotinamide,
6-[5-(2-m-Tolyl-ethylamino)-5,6,7,8-tetrahydro-naphthalen-2-yloxy]-nicotinamide,
6-{5-[2-(4-Fluoro-phenyl)-1,1-dimethyl-ethylamino]-5,6,7,8-tetrahydro-naphthalen-2-yloxy}-nicotinamide,
6-{1-[2-(4-Fluoro-phenyl)-1,1-dimethyl-ethylamino]-indan-5-yloxy}-nicotinamide,
6-[5-(3-Hydroxy-propylamino)-5,6,7,8-tetrahydro-naphthalen-2-yloxy]-nicotinamide,
6-[1-(3-Hydroxy-propylamino)-indan-5-yloxy]-nicotinamide,
6-[5-(2,2,2-Trifluoro-ethylamino)-5,6,7,8-tetrahydro-naphthalen-2-yloxy]-nicotinamide,
6-[1-(2,2,2-Trifluoro-ethylamino)-indan-5-yloxy]-nicotinamide,
6-[5-(2,2-Diphenyl-ethylamino)-5,6,7,8-tetrahydro-naphthalen-2-yloxy]-nicotinamide,
6-[5-(4-Phenyl-piperidin-1-yl)-5,6,7,8-tetrahydro-naphthalen-2-yloxy]-nicotinamide,
6-[1-(4-Phenyl-piperidin-1-yl)-indan-5-yloxy]-nicotinamide,
6-[5-(Benzyl-methyl-amino)-5,6,7,8-tetrahydro-naphthalen-2-yloxy]-nicotinamide,
6-[1-(Benzyl-methyl-amino)-indan-5-yloxy]-nicotinamide,
6-[5-(3,4-Dihydro-1H-isoquinolin-2-yl)-5,6,7,8-tetrahydro-naphthalen-2-yloxy]-nicotinamide,
6-[1-(3,4-Dihydro-1H-isoquinolin-2-yl)-indan-5-yloxy]-nicotinamide,
6-(5-Thiomorpholin-4-yl-5,6,7,8-tetrahydro-naphthalen-2-yloxy)-nicotinamide,
6-(1-Thiomorpholin-4-yl-indan-5-yloxy)-nicotinamide,
2-[6-(5-Carbamoyl-pyridin-2-yloxy)-1,2,3,4-tetrahydro-naphthalen-1-yl]-1,2,3,4-tetrahydro-isoquinoline-3-carboxylic acid tert-butylamide,
2-[6-(5-Carbamoyl-pyridin-2-yloxy)-1,2,3,4-tetrahydro-naphthalen-1-yl]-1,2,3,4-tetrahydro-isoquinoline-3-carboxylic acid tert-butylamide,
6-[5-(5-Oxo-[1,4]diazepan-1-yl)-5,6,7,8-tetrahydro-naphthalen-2-yloxy]-nicotinamide,
6-[1-(5-Oxo-[1,4]diazepan-1-yl)-indan-5-yloxy]-nicotinamide,
6-[5-(Methyl-phenethyl-amino)-5,6,7,8-tetrahydro-naphthalen-2-yloxy]-nicotinamide,
6-[1-(3-Acetylamino-pyrrolidin-1-yl)-indan-5-yloxy]-nicotinamide,
6-[1-(3-Phenyl-piperidin-1-yl)-indan-5-yloxy]-nicotinamide,
6-[1-(3-Phenyl-pyrrolidin-1-yl)-indan-5-yloxy]-nicotinamide,
6-[1-(3-Propylamino-propylamino)-indan-5-yloxy]-nicotinamide,
6-[1-(3,3-Dimethyl-butylamino)-indan-5-yloxy]-nicotinamide,
6-(1-Decylamino-indan-5-yloxy)-nicotinamide,
6-[1-(2-Ethyl-hexylamino)-indan-5-yloxy]-nicotinamide,
6-{1-[(Tetrahydro-furan-2-ylmethyl)-amino]-indan-5-yloxy}-nicotinamide,
6-(1-Cycloheptylamino-indan-5-yloxy)-nicotinamide,
6-{1-[2-(1-Methyl-pyrrolidin-2-yl)-ethylamino]-indan-5-yloxy}-nicotinamide,
6-(1-Cyclopropylamino-indan-5-yloxy)-nicotinamide,
6-[1-(1,3-Dimethyl-butylamino)-indan-5-yloxy]-nicotinamide,
6-(1-Cyclooctylamino-indan-5-yloxy)-nicotinamide,
6-[1-(2,3-Dimethyl-cyclohexylamino)-indan-5-yloxy]-nicotinamide,
6-(1-Cyclobutylamino-indan-5-yloxy)-nicotinamide,
6-(1-Cyclopentylamino-indan-5-yloxy)-nicotinamide,
6-[1-(Cyclohexylmethyl-amino)-indan-5-yloxy]-nicotinamide,
6-{1-[(1-Ethyl-pyrrolidin-2-ylmethyl)-amino]-indan-5-yloxy}-nicotinamide,
6-[1-(3-Cyclohexylamino-propylamino)-indan-5-yloxy]-nicotinamide,
6-[1-(3-Methyl-cyclohexylamino)-indan-5-yloxy]-nicotinamide,
6-(1-Cyclohexylamino-indan-5-yloxy)-nicotinamide,
6-[1-(1-Isopropyl-2-methyl-propylamino)-indan-5-yloxy]-nicotinamide,
6-[1-(2-Cyclohex-1-enyl-ethylamino)-indan-5-yloxy]-nicotinamide,
6-[1-(2-Methyl-butylamino)-indan-5-yloxy]-nicotinamide,
6-[1-(4-Hydroxy-cyclohexylamino)-indan-5-yloxy]-nicotinamide,
6-[1-(1,4-Dimethyl-pentylamino)-indan-5-yloxy]-nicotinamide,
6-[1-(1-Cyclohexyl-ethylamino)-indan-5-yloxy]-nicotinamide,
6-[1-(3,3,5-Trimethyl-cyclohexylamino)-indan-5-yloxy]-nicotinamide,
6-[1-(2-Carbamoyl-cyclohexylamino)-indan-5-yloxy]-nicotinamide,
6-[1-(Cyclopropylmethyl-amino)-indan-5-yloxy]-nicotinamide,
6-[1-(3-Butoxy-propylamino)-indan-5-yloxy]-nicotinamide,
6-[1-(2,2,3,3,4,4,4-Heptafluoro-butylamino)-indan-6-yloxy]-nicotinamide,
6-{1-[3-(2-Oxo-pyrrolidin-1-yl)-propylamino]-indan-5-yloxy}-nicotinamide, 6-[1-(3-Azepan-1-yl-propylamino)-indan-5-yloxy]-nicotinamide,
6-[1-(2,2,3,3,3-Pentafluoro-propylamino)-indan-5-yloxy]-nicotinamide,
6-{1-[(2-Hydroxy-cyclooctylmethyl)-amino]-indan-5-yloxy}-nicotinamide,
6-[1-(Bicyclohexyl-2-ylamino)-indan-5-yloxy]-nicotinamide,
6-[1-(2-Hydroxy-cyclohexylamino)-indan-5-yloxy]-nicotinamide,
6-{1-[2-(2-Methyl-cyclohexyl)-ethylamino]-indan-5-yloxy}-nicotinamide,
6-{1-[2-(4-Methyl-cyclohexyl)-ethylamino]-indan-5-yloxy}-nicotinamide,
6-[1-(2-Cyclopentyl-ethylamino)-indan-5-yloxy]-nicotinamide,
6-[1-(Phenethylamino-methyl)-indan-5-yloxy]-nicotinamide,
6-[8-(Phenethylamino-methyl)-5,6,7,8-tetrahydro-naphthalen-2-yloxy]-nicotinamide,
6-[3-(Phenethylamino-methyl)-indan-5-yloxy]-nicotinamide,
6-[5-(Phenethylamino-methyl)-5,6,7,8-tetrahydro-naphthalen-1-yloxy]-nicotinamide,
6-[1-(Benzylamino-methyl)-indan-5-yloxy]-nicotinamide,
6-[8-(Benzylamino-methyl)-5,6,7,8-tetrahydro-naphthalen-2-yloxy]-nicotinamide,
6-[3-(Benzylamino-methyl)-indan-5-yloxy]-nicotinamide,
6-[5-(Benzylamino-methyl)-5,6,7,8-tetrahydro-naphthalen-1-yloxy]-nicotinamide,
6-{1-[(3-Methyl-butylamino)-methyl]-indan-5-yloxy}-nicotinamide,
6-{8-[(3-Methyl-butylamino)-methyl]-5,6,7,8-tetrahydro-naphthalen-2-yloxy}-nicotinamide,
6-{3-[(3-Methyl-butylamino)-methyl]-indan-5-yloxy}-nicotinamide,
6-{5-[(3-Methyl-butylamino)-methyl]-5,6,7,8-tetrahydro-naphthalen-1-yloxy}-nicotinamide,
6-{1-[(2-Cyclohexyl-ethylamino)-methyl]-indan-5-yloxy}-nicotinamide,
6-{8-[(2-Cyclohexyl-ethylamino)-methyl]-5,6,7,8-tetrahydro-naphthalen-2-yloxy}-nicotinamide,
6-{5-[(2-Cyclohexyl-ethylamino)-methyl]-5,6,7,8-tetrahydro-naphthalen-1-yloxy}-nicotinamide,
6-{1-[(Cyclohexylmethyl-amino)-methyl]-indan-5-yloxy}-nicotinamide,
6-{8-[(Cyclohexylmethyl-amino)-methyl]-5,6,7,8-tetrahydro-naphthalen-2-yloxy}-nicotinamide,
6-{3-[(Cyclohexylmethyl-amino)-methyl]-indan-5-yloxy}-nicotinamide,
6-{5-[(Cyclohexylmethyl-amino)-methyl]-5,6,7,8-tetrahydro-naphthalen-1-yloxy}-nicotinamide,
6-{1-[(2-Cyclopentyl-ethylamino)-methyl]-indan-5-yloxy}-nicotinamide, and a pharmaceutically acceptable salt, solvate or enantiomer thereof.

Most preferred compounds of the invention include compounds selected from the group consisting of:
6-(8-Pentylamino-5,6,7,8-tetrahydro-naphthalen-2-yloxy)-nicotinamide,
6-(5-Pentylamino-5,6,7,8-tetrahydro-naphthalen-2-yloxy)-nicotinamide,
6-(5-Pentylamino-5,6,7,8-tetrahydro-naphthalen-1-yloxy)-nicotinamide,
6-(1-Pentylamino-indan-5-yloxy)-nicotinamide,
6-(1-Pentylamino-indan-4-yloxy)-nicotinamide,
6-(B-Benzylamino-5,6,7,8-tetrahydro-naphthalen-2-yloxy)-nicotinamide,
6-(5-Benzylamino-5,6,7,8-tetrahydro-naphthalen-2-yloxy)-nicotinamide,
6-(5-Benzylamino-5,6,7,8-tetrahydro-naphthalen-1-yloxy)-nicotinamide,
6-(1-Benzylamino-indan-4-yloxy)-nicotinamide,
6-(8-Phenethylamino-5,6,7,8-tetrahydro-naphthalen-2-yloxy)-nicotinamide,
6-(5-Phenethylamino-5,6,7,8-tetrahydro-naphthalen-2-yloxy)-nicotinamide,
6-(5-Phenethylamino-5,6,7,8-tetrahydro-naphthalen-1-yloxy)-nicotinamide,
6-(1-Phenethylamino-indan-4-yloxy)-nicotinamide,
6-{8-[2-(3-Fluoro-phenyl)-ethylamino]-5,6,7,8-tetrahydro-naphthalen-2-yloxy}-nicotinamide, and a pharmaceutically acceptable salt, solvate or enantiomer thereof.

Preparing the Compound of the Invention

Compounds of formula I may be prepared as described in the following Schemes and Examples. The compounds employed as initial starting materials in the synthesis of compounds of the invention are well known and, to the extent not commercially available, are readily synthesized using specific references provided, or by standard procedures commonly employed by those of ordinary skill in the art and/or are found in general reference texts.

More particularly, the compounds of the invention are produced in accordance with schemes 1 through 10 that are described in detail below, or analogous methods thereto. These reactions are often carried out following known procedures, methods, or analogous methods thereto. Examples of such known procedures and methods include those described in general reference texts such as Comprehensive Organic Transformations, VCH Publishers Inc, 1989; Compendium of Organic Synthetic Methods, Volumes 1-10, 1974-2002, Wiley Interscience; Advanced Organic Chemistry, Reactions Mechanisms, and Structure, 5$^{th}$ Edition, Michael B. Smith and Jerry March, Wiley Interscience, 2001; Advanced Organic Chemistry, 4$^{th}$ Edition, Part B, Reactions and Synthesis, Francis A. Carey and Richard J. Sundberg, Kluwer Academic/Plenum Publishers, 2000, etc., and references cited therein.

Compounds of the present invention are generally prepared starting with a coupling reaction to form the ether linkage between the aryl groups Ar$^2$ and Ar$^3$. The alkylamino appendage or substituent on the bicyclic ring Ar$^2$ is formed by reductive amination on a keto functionality already present on the ring followed by elaboration of the substituent to form the desired group. The final compound is then obtained by elaboration of a cyano or amido group on the ring Ar$^3$. Alternatively the side chain on Ar$^2$ is formed by displacement of an alkylhalide substituent on the Ar$^2$ ring. The alkylhalide substituent is itself introduced via a hydroxy group or a reduced keto group. Details of specific procedures are provided in the schemes below.

Scheme 1

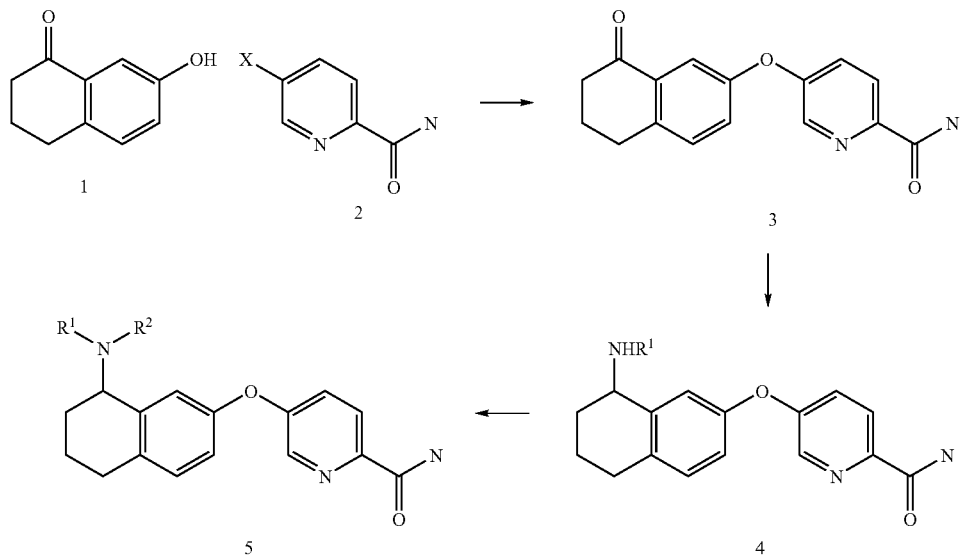

As shown in scheme 1, certain compounds of the present invention are prepared starting with an optionally substituted hydroxytetralone compound 1. The tetralone compound provides the framework for the 6,6-bicyclic structure representing $Ar^2$ of formula 1. The hydroxytetralone 1 is typically reacted with a halonicotinonitrile compound or a halonicotinamide 2 to afford the ether linked compound 3. Various positional isomers of hydroxytetralone, halonicotinonitrile or halonicotinamide may be employed to effect preparation of position isomers or analogs of the compound 3. Preferred halogen substituents for the displacement reaction are fluoro, chloro, or bromo. The displacement reaction is preferably performed under basic conditions such as with sodium or potassium carbonate in a suitable polar solvent such as for example, dimethylacetamide (DMA), dimethylformamide (DMF), dimethyl sulfoxide (DMSO) and the like. The reaction is typically performed a temperatures ranging from room temperature to reflux temperatures depending on the particular substrates. The ether 3 is then reductively aminated with a suitable amine to form the compound 4 or 5. The use of a primary amine results in the amine 4, which may be further converted to the tertiary amine 5 using processes known to one of skill in the art and/or disclosed in the experimental section. Alternatively, where a tertiary amine is desired and the reaction is not likely to be detrimentally affected by steric considerations, a secondary amine may be used in the reductive amination step to afford the compound 5 or analog thereof.

Preparing the benzamide analog of the compounds of formula 4 or 5 may be accomplished by using the appropriately substituted benzamide or benzonitrile as shown in scheme 2 below.

Scheme 2

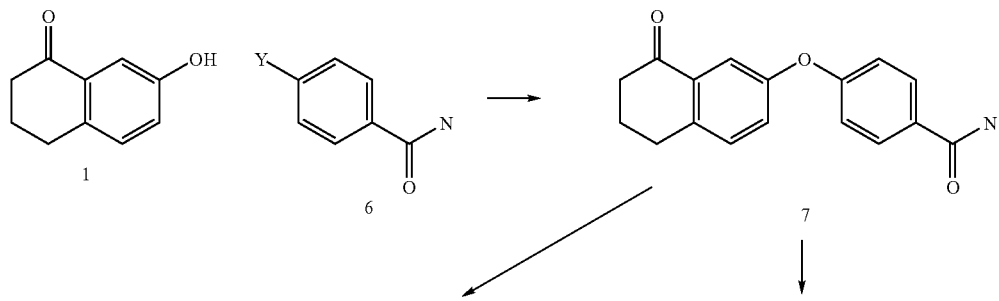

-continued

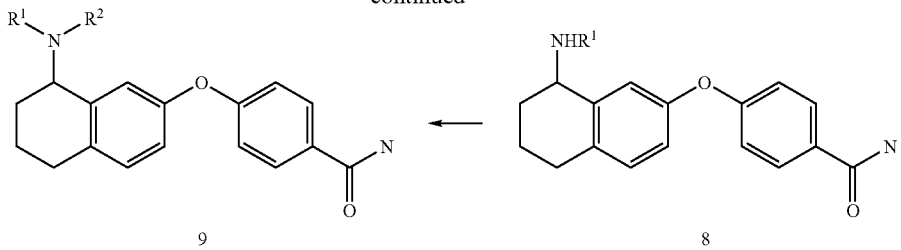

9    8

For Schemes 1 and 2, wherein the C-ring of formula I is introduced via the nitrile, the resulting nitrile may be converted to the amide by basic hydrolysis in the presence of hydrogen peroxide. Details of this and other methods of hydrolyzing nitrile to amide are known to one of skill in the art and/or are disclosed in the experimental section. Where the nitrile is used in the initial reaction, it may be preferable for some substrates that the conversion to the amide be effected prior to the reductive amination step. As in Scheme 1.

The indane analog (wherein the A-ring is a 5-member ring) of compounds of formula I may be similarly prepared using the desired 2-hydroxy indanone as starting material in a scheme such as Scheme 2 above. As with Scheme 1, the coupled product 7 is then reductively aminated with ammonia or a desired substituted amine to afford the compound 8 or 9 directly.

Compounds of formula I wherein the appropriately substituted hydroxytetralone or hydroxyindanone or hydroxy tetrahydroisoquinolone is not commercially available may be accessed starting from the corresponding methoxy compound 10 as shown in Scheme 3.

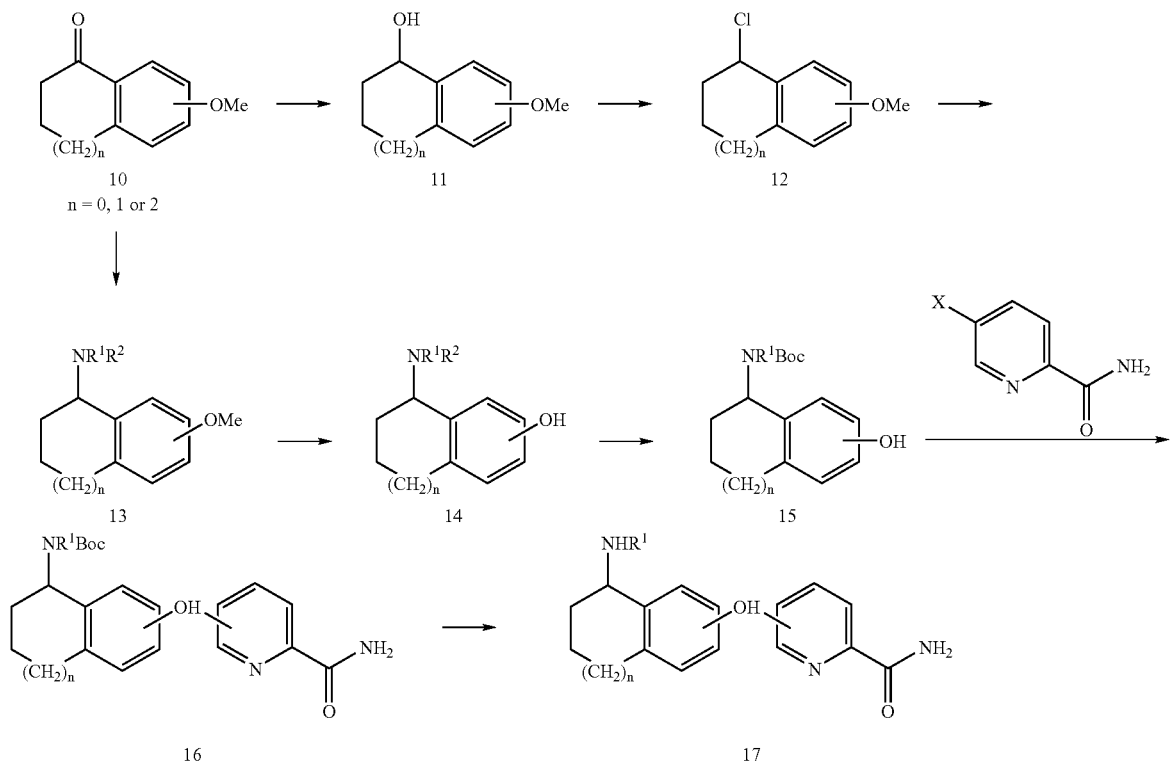

Protection of the hydroxy group as the methoxy group as in compound 10 also allows for installation of the amino side chain on the bicyclic ring via a displacement reaction of an intermediate halide. As shown in Scheme 3, the tetralone or indanone compound 10 is reduced to the alcohol 11 using known reducing agents such as the borohydride reagents e.g. sodium borohydride, or the aluminum hydride reducing agents, e.g. $NaAlH_4$. The procedures and conditions for effecting such reductions are known to one of skill in the art, may be found in general organic reference texts disclosed herein or are disclosed in the experimental section. The alcohol 11 is then displaced with a nucleophile source to afford a leaving group such as for example, chloride or bromide or other sulfonate ester. Formation of chloride leaving group for example, is accomplished by reacting the intermediate 11 with for example, thionyl chloride in a suitable solvent such as toluene or dichloromethane at temperatures ranging from ambient to reflux temperatures. The resulting chloride 12 is displaced with an amine in a suitable polar aprotic solvent to afford either the primary, secondary or tertiary amine depending on whether the reacting amine source is ammonia, primary or secondary amine. The reactive hydrogen of a primary or secondary amine 13 (where one or both of $R^1$ and $R^2$ are hydrogen) may be protected as the Boc-group after de-methylation to form compound 15. Compound 15 may be reacted with a source of nicotinamide or nicotinonitrile or benzamide or benzonitrile as desired. The use of optionally substituted 3-halonicotinamide is shown in the Scheme 3. One of skill in the art is aware that other sources of the Ar3 group according to formula I may be introduced as discussed herein or as disclosed in the experimental section.

A modification of the scheme 3 protocol wherein the coupling to form the ether backbone of a compound of formula I is effected prior to formation of the amino side chain is shown in scheme 4 below.

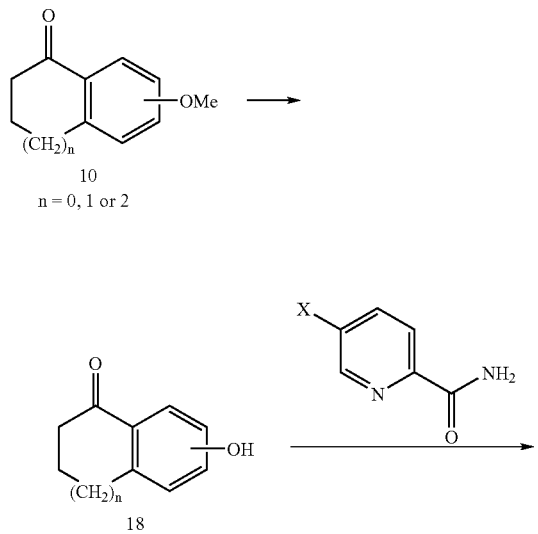

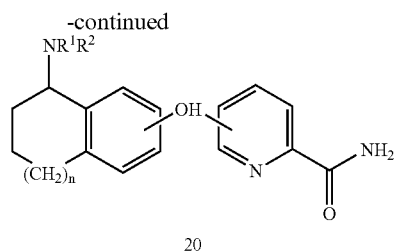

According to Scheme 4, the starting material 10 is de-methylated to afford the hydroxy compound 18. The de-methylation may be accomplished by use of 48% HBr or boron tribromide. Details of the procedures for effecting the above de-methylation has been discussed previously, are known to one of skill in the art and/or disclosed in the experimental section herein. The hydroxy compound 18 is then coupled with a benzamide or nicotinonitrile or other source of the C-ring of a compound of formula I. The use of halonico-tinonitrile in shown in the scheme above to afford the ether compound 19. The conditions to effect the coupling reaction have been described earlier and in the experimental section. The ether 19 is reductively aminated at the carbonyl group to afford the amine compound 17. The amine 17 may be converted to the compound 20 wherein both $R^1$ and $R^2$ are not hydrogen atoms following procedures known to one of skill in the art.

Compounds of formula I wherein the alkyl chain length of the amino side chain i.e. p is 1, may be prepared following the protocol of Scheme 5 below or known variations thereof.

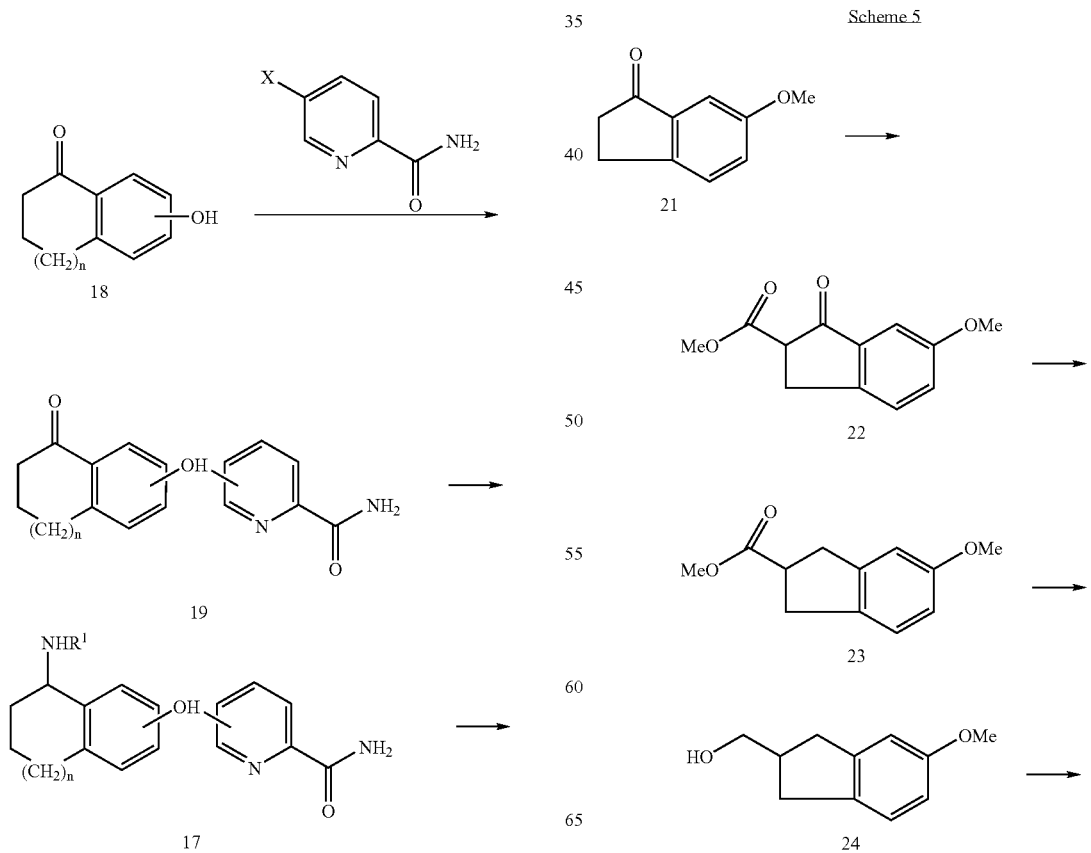

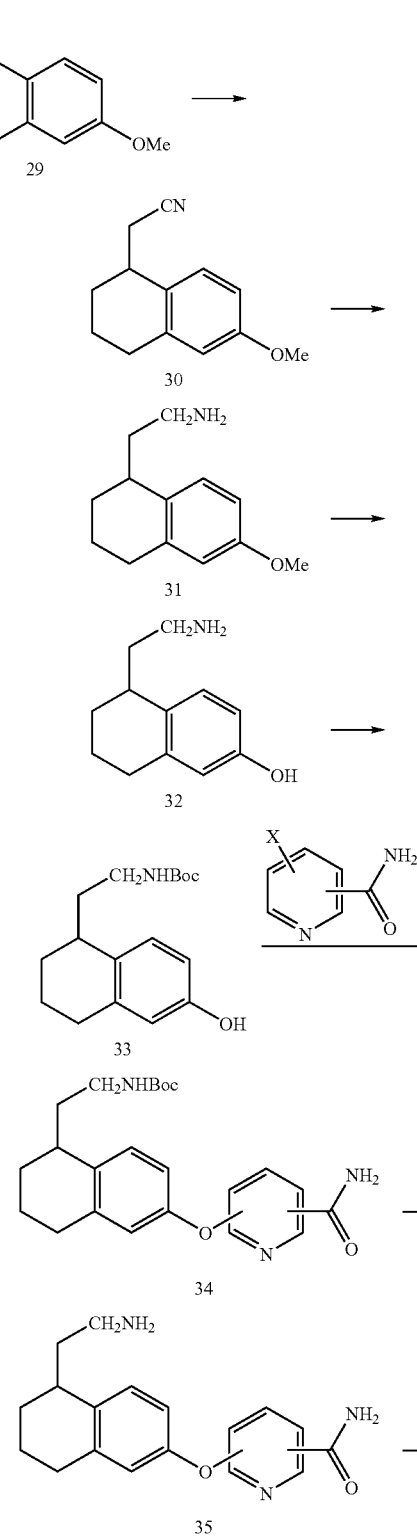

Compounds of formula I wherein p is 2 may be prepared by the procedure given in schemes 7 or 8 below or analogous procedures obtained by modifications known to one of skill in the art.

As shown in Scheme 5, 5-methoxy indanone (21) may be reacted with dimethylcarbonate in the presence of a strong base such as sodium hydride to afford the 5-methoxy-indan-1-oxo-2-carboxylic acid methyl ester (22). The indanone ester 22 may be reduced to the indane methyl ester 23 using palladium on carbon in the presence of a proton donor such as perchloric acid, and a suitable solvent such as acetic acid. The resulting indane methylester 23 is further reduced to the methoxyindane alcohol 24 using lithium aluminum hydride or other suitable reducing agents. The free hydroxy group of compound 24 may be protected using suitable OH-protecting groups prior to de-methylation reaction of 24 to afford the product 25. The removal of the methoxy group of the protected methoxyindane alcohol 24 may be accomplished using concentrated HBr, e.g. 48% HBr. Alternatively, boron tribromide may be used. The resulting hydroxy compound 25 is then coupled with a source of nicotinonitrile, nicotinamide, benzonitrile or benzamide. A suitable source in each case is an appropriately substituted halide. Scheme 5, for example shows the use of a halonicotinamide. A preferred halogen is the chloride. The coupling reaction to form the ether linkage has been described previously, and affords the ether 26 following deprotection as appropriate. Oxidation of the alcoholic functionality of the ether 26 affords the aldehyde 27. Specific procedures for oxidation of the alcohol include the Swern oxidation. The Swern oxidation may be accomplished by adding the alcohol 26 into a cold solution/mixture formed by adding dimethyl sulfoxide to a solution of oxalyl chloride in a suitable solvent such as dichloromethane. Detailed procedures for effecting the Swern oxidation and other methods of oxidizing alcohols are provided in general reference texts, are known to one of skill in the art, and/or disclosed in the experimental section herein. The aldehyde 27 is then reductively aminated with the desired amine to afford the compound 28.

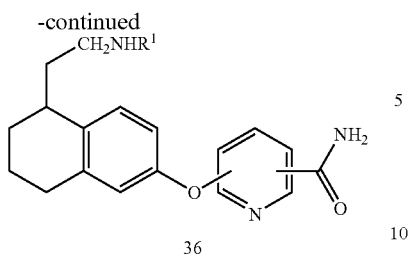

36

Compound 29 of Scheme 6 may be converted to compound 30 via a series of reactions beginning with formation of an acrylonitrile via the Horner-Emmons-Wadsworth modification of the Wittig reaction using diethylphosphonoacetonitrile diethylcyanomethyl phosphonate to form an acrylonitrile intermediate (see *J. Org. Chem.* 30, 505 (1965) and also *J. Am. Chem. Soc.*, 83 1733 (1961). The acrylonitrile intermediate or substituted derivative thereof, may be reduced to the saturated nitrile 30 using for example hydrogenation using palladium (II) chloride catalyst, and sodium borohydride in a protic solvent such as methanol. For reference see Jelliman, C., et al, *J. Med. Chem.*, 43 (22) 4051-4062 (2000). The nitrile 30 may be reduced to the ethylamine derivative 31 by hydrogenation using Raney Nickel and ammonium hydroxide in THF as disclosed in Jelliman et. al., supra. The ethylamine compound 31 may be demethlyated to form the hydroxy compound 32. The hydroxy compound 32 may be reacted directly with a nicotinamide source or a benzamide source or synthon to afford a compound of the invention. Alternatively the hydroxy compound 32 is protected at the amine prior to coupling with a nicotinamide or benzamide source or synthon. The protected compound 33 is coupled with a source of the 'C' ring to afford the coupled and protected compound 34. The compound 34 is then de-protected to afford the desired compound of the invention 35 which may itself be converted to other substituted amine derivatives such as compound 36 following procedures known to one of skill in the art or disclosed herein. One of skill in the art is aware that compounds of formula I wherein $R^3$ and/or $R^{3'}$ are other than hydrogen may be prepared by alkylation at the free methyne carbon atom of the acrylonitrile intermediate from compound 29, or the nitrile 30 to afford substituted derivatives of a compound of formula I. Such alkylations may be accomplished by following procedures similar to those disclosed in *Synthesis*, 516 (19750.

In an alternate method, compounds of formula I wherein p is 2 may be prepared following a scheme such as Scheme 7.

Scheme 7

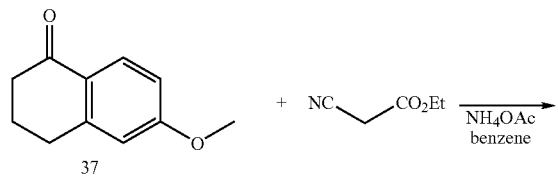

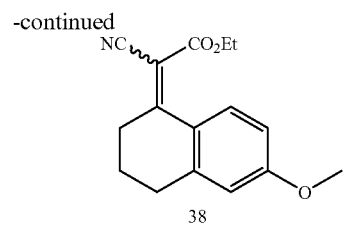

1) KCN, EtOH
2) LAH, THF
3) NaOH$_{eq}$

As shown in Scheme 7, methoxy tetralone 37 is subjected to a Knoevenagel type nucleophilic substitution with ethyl-cyanoacetate to afford upon elimination of water, the acrylonitrile acetate compound 38 according to procedures described in Mukhopadhyay et al. *J. Chem Res, Synop* 1993, 12, 476-477. Other examples of the Knoevenagel reaction may be found in *Name Reactions and Reagents in Organic Synthesis* by Bradford P. Mundy and Michael G, Ellerd, Wiley InterScience Publishers, 1988, New York, N.Y. and references cited therein. The compound 38 is then subjected to a decarboxylation and reduction sequence to afford the aminoethyl compound 40 according to a procedure similar to that described in New et al., *Synthesis* 1983, 388. The resulting 4-methoxy aminoethyl compound 40 is then demethylated to afford the hydroxy compound 41 using, for example, boron tribromide or 48% HBr as the demethylating agent. The hydroxy compound 41 is then reacted with an appropriately substituted halo nicotinamide or halo-benzamide source (e.g. 4-chlorobenzene carboxamide shown) or synthon thereof, to afford the ether compound 42. The ether compound 42 may be elaborated to substituted amines by procedures known to one of skill in the art.

In yet an alternative procedure compounds of formula I wherein p is 2 may be prepared following a scheme such as Scheme 8.

verted to a chloride intermediate by reaction with thionyl chloride or other chlorinating agent. The chloride intermediate is displaced with ammonia or amine to afford the primary or substituted amine 44 respectively. The methoxy amine compound 44 is then de-methylated at the methoxy group to form the alcohol 45. The alcohol 45 is then coupled with an appropriately substituted halonicotinamide, halo-benzamide or other desired heterocyclic amide source or synthon to afford compound 46, a compound of the invention.

Compounds of formula I wherein p for the amine side chain is 3 may be prepared as shown in scheme 9.

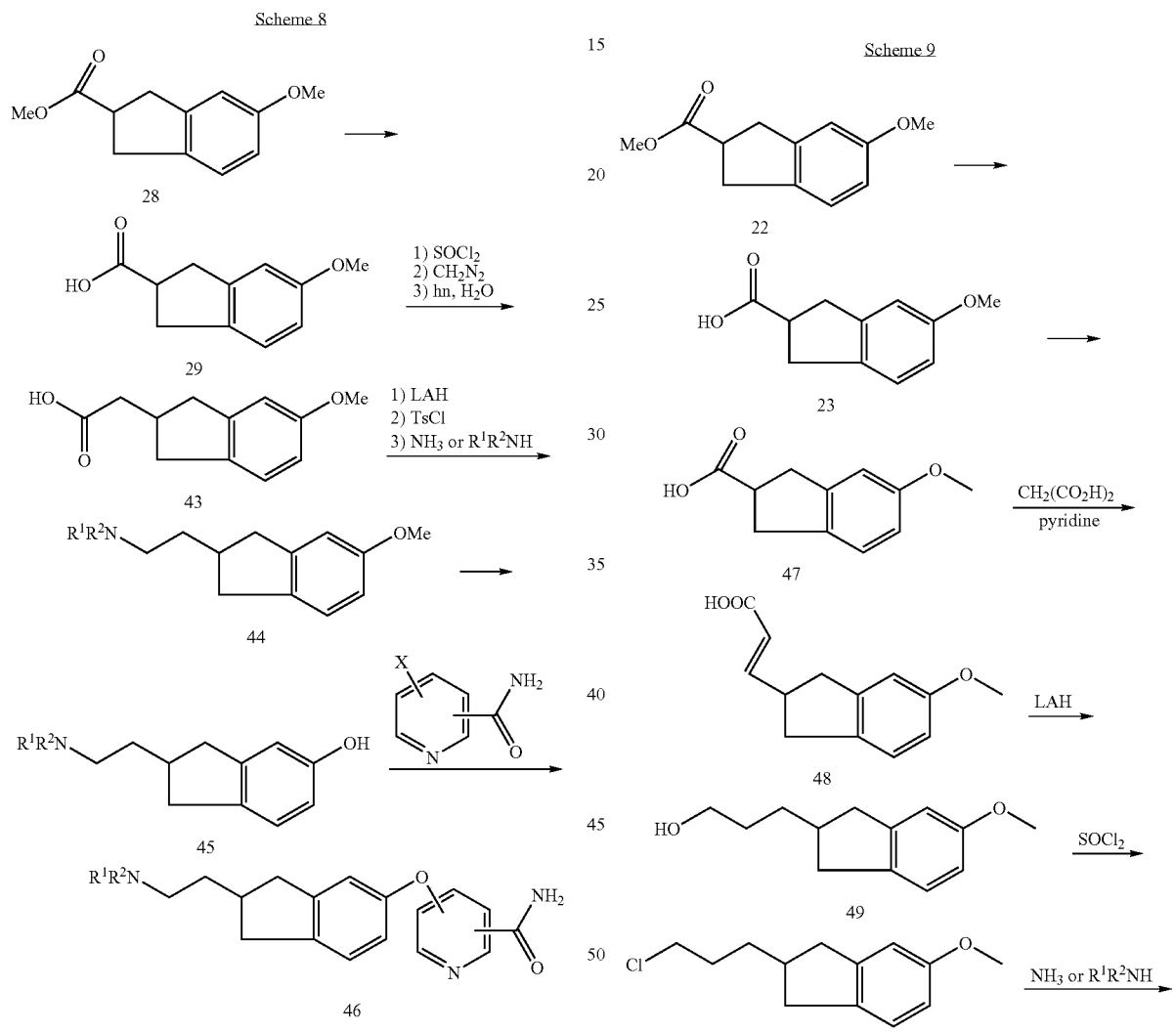

According to Scheme 8, compound 28 (Scheme 5) may be hydrolyzed to the acid 29. The acid 29 is farther converted to an acid halide intermediate, e.g. acyl chloride, using for example, thionyl chloride in an aprotic solvent. The acyl halide intermediate is then converted to a diazoketone intermediate by reaction with diazomethane. The diazoketone intermediate is converted to a methylester intermediate which upon a Arndt-Eistert reaction affords the acid 43. Procedures for converting the acid 29 to the acid 43 are similar to those employed and disclosed in Walsh, E. J., et al, *Tetrahedron Letters*, 1986, (27) 1127-1130 and references therein. The acid 43 is then reduced to the alcohol using, for example, lithium aluminum hydride. The intermediate alcohol is con- -continued

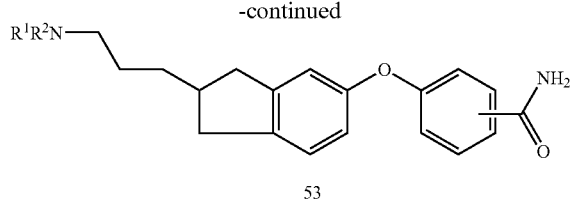

53

As shown in scheme 9, compound 22 which formation has been discussed previously, may be converted to the acid 23 by basic hydrolysis followed by acidic workup. The acid 23 may be reduced to the aldehyde 47. Procedures for reduction of acids to aldehydes are known to one of skill in the art. The aldehyde 47 is then reacted with malonic acid in the presence of a base to afford the acrylic acid 48. The acrylic acid 48 is reduced in one or two steps to the propanol derivative 49. The propanol derivative 49 is then converted to the primary amine or the substituted amine depending on whether ammonia or a substituted amine is used to react with the propyl chloride derivative 50 formed from a halogenation reaction of the propanol derivative 49. The halogenation of the propanol derivative 49 is effected with thionyl chloride or other chlorinating agent. The chloride 50 is then displaced with an amine source to afford the desired amine component 51. The methoxy group of the amine 51 may be reduced to the hydroxy group using procedures described herein to afford the phenoxy compound 52. The phenoxy compound 52 may be coupled with a source of nicotinamide, benzamide, synthon thereof, or other source of the C-ring of compound of formula I to afford the compound 53, a compound of the invention.

Method of Using the Invention

As noted above, the compounds of the present invention are useful in blocking the effect of agonists at mu, kappa, and/or delta opioid receptors. As such, the present invention also provides a method for blocking a mu, kappa, delta receptor or receptor combination (heterodimer) thereof in mammals comprising administering to a mammal requiring blocking of a mu, kappa, delta or combinations of mu, kappa, and/or delta receptors, a receptor blocking dose of a compound of formula I.

The term "receptor blocking dose", as used herein, means an amount of a compound of formula I necessary to block a mu, kappa, or delta receptor or receptor combination (heterodimer) thereof following administration to a mammal requiring blocking of a mu, kappa, or delta receptor or receptor combination (heterodimer) thereof.

The compounds of formula I or combinations thereof, are effective over a wide dosage range. For example, dosages per day will normally fall within the range of about 0.05 to about 250 mg/kg of body weight. In the treatment of adult humans, the range of about 0.05 to about 10 mg/kg, in single or divided doses, is preferred. However, it will be understood that the amount of the compound actually administered will be determined by a physician in light of the relevant circumstances, including the condition to be treated, the choice of compound to be administered, the age, weight, and response of the individual patient, the severity of the patient's symptoms, and the chosen route of administration, and therefore the above dosage ranges are not intended to limit the scope of the invention in any way. The compounds may be administered by a variety of routes such as the oral, transdermal, subcutaneous, intranasal, intramuscular and intravenous routes.

A variety of physiologic functions have been shown to be subject to or influenced by mu, kappa, or delta receptors or receptor combination (heterodimers) in the brain. As such, the compounds of the present invention are believed to have the ability to treat a variety of disorders in mammals associated with these receptors or combinations thereof, such as eating disorders, opioid overdose, depression, smoking, alcoholism, sexual dysfunction, shock, stroke, spinal damage and head trauma. As such, the present invention also provides methods of treating the above disorders by blocking the effect of agonists at a mu, kappa, delta receptor or receptor combination (heterodimer) thereof. The compounds of the present invention have been found to display excellent activity in an opioid receptor binding assay which measures the ability of the compounds to block the mu, kappa, delta or receptor combination (heterodimer) thereof.

GTP-γ-S Binding Assay

A scintillation proximity assay (SPA)-based GTP-γ-$S^{35}$ assay format was developed based on previous opioid (Emmerson et al., J. Pharm Exp Ther 278,1121,1996; Horng et al., Society for Neuroscience Abstracts, 434.6, 2000) and muscarinic (DeLapp et al., JPET 289, 946, 1999) assay formats. Membranes were resuspended in 20 mM HEPES, 100 mM NaCl, 5 mM $MgCl_2$, 1 mM DTT, and 1 mM EDTA. Fifty mL of GTP-γ-[35S], compound, membrane suspension (20 microgram/well), and wheat germ agglutinin coated SPA beads (1 mg/well) were added to clear bottom 96 well assay plates. GDP (200 mM) was added to the membrane solution prior to addition to the assay plates. Plates were sealed and incubated for four hours at room temperature then placed in a refrigerator overnight to allow the beads to settle. Signal stability at 4° C. was determined to be >60 hours. Plates were warmed to room temperature and counted in a Wallac Microbeta scintillation counter. For antagonist assays, specific agonists were added at the following concentrations: (MOR) DAMGO 1 micromolar, (DOR) DPDPE 30 nM, (KOR) U69593 300 nM. Kb's were determined by Cheng-Prusoff equation (see Cheng and Prusoff, Biochem. Pharmacol. 22, 3099, 1973). Results obtained for a sample of compounds of the invention in the GTP-γ-S Binding Assay are shown in table 1 below.

TABLE 1

| Compound of Example | IUPAC name | Mu Kb (nM) | Kappa Kb (nM) | Delta Kb (nM) |
|---|---|---|---|---|
| 90 | 6-{1-[2-(4-Fluoro-phenyl)-ethylamino]-indan-5-yloxy}-nicotinamide | 0.4 | 9.2 | 14.6 |
| 195 | 6-{5-[(2-Cyclohexyl-ethylamino)-methyl]-5,6,7,8-tetrahydro-naphthalen-1-yloxy}-nicotinamide | 0.5 | 76.0 | 7.9 |
| 192 | 6-{5-[(3-Methyl-butylamino)-methyl]-5,6,7,8-tetrahydro-naphthalen-1-yloxy}-nicotinamide | 1.1 | 11.8 | 9.4 |
| 202 | 6-{5-[(3,3-Dimethyl-butylamino)-methyl]-5,6,7,8- | 0.65 | 5.79 | 4.09 |

TABLE 1-continued

| Compound of Example | IUPAC name | Mu Kb (nM) | Kappa Kb (nM) | Delta Kb (nM) |
|---|---|---|---|---|
| 20 | tetrahydro-naphthalen-1-yloxy}-nicotinamide 6-{1-[Methyl-(3-methyl-butyl)-amino]-indan-5-yloxy}-nicotinamide | 0.73 | 2.5 | 13.48 |

Formulation

While it is possible to administer a compound of the invention directly without any formulation, the compounds are preferably employed in the form of a pharmaceutical formulation comprising a pharmaceutically acceptable carrier, diluent or excipient and a compound of the invention. Such compositions will contain from about 0.1 percent by weight to about 90.0 percent by weight of a present compound. As such, the present invention also provides pharmaceutical formulations comprising a compound of the invention and a pharmaceutically acceptable carrier, diluent or excipient thereof.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material that acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium, and soft and hard gelatin capsules.

Examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

For oral administration, a compound of this invention ideally can be admixed with carriers and diluents and molded into tablets or enclosed in gelatin capsules.

The compositions are preferably formulated in a unit dosage form, each dosage containing from about 1 to about 500 mg, more usually about 5 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In order to more fully illustrate the operation of this invention, the following formulation examples are provided. The examples are illustrative only, and are not intended to limit the scope of the invention. The formulations may employ as active compounds any of the compounds of the present invention.

Formulation 1

Hard gelatin capsules are prepared using the following ingredients:

| Compound | Amount per capsule (mg) | Concentration by weight (%) |
|---|---|---|
| Cyclohexyl-3-hydroxy-propyl)-3,4-dimethyl-piperidin-4-yl]-benzamide | 250 | 55 |
| Starch dried | 200 | 43 |
| Magnesium stearate | 10 | 2 |

The above ingredients are mixed and filled into hard gelatin capsules in 460 mg quantities.

Formulation 2

Capsules each containing 20 mg of medicament are made as follows:

| Compound | Amount per capsule (mg) | Concentration by weight (%) |
|---|---|---|
| Cyclohexyl-3-hydroxy-propyl)-3,4-dimethyl-piperidin-4-yl]-benzamide | 20 | 10 |
| Starch | 89 | 44.5 |
| Microcrystalline cellulose | 89 | 44.5 |
| Magnesium stearate | 2 | 1 |

The active ingredient, cellulose, starch and magnesium stearate are blended, passed through a No. 45 mesh U.S. sieve and filled into a hard gelatin capsule.

Formulation 3

Capsules each containing 100 mg of active ingredient are made as follows:

| Compound | Amount per capsule (mg) | Concentration by weight (%) |
|---|---|---|
| Cyclohexyl-3-hydroxy-propyl)-3,4-dimethyl-piperidin-4-yl]-benzamide | 100 | 30 |
| Polyoxyethylene Sorbitan monooleate | 50 mcg | 0.02 |
| Starch powder | 250 | 69.98 |

The above ingredients are thoroughly mixed and placed in an empty gelatin capsule.

Formulation 4

Tablets each containing 10 mg of active ingredient are prepared as follows:

| Compound | Amount per capsule (mg) | Concentration by weight (%) |
|---|---|---|
| Cyclohexyl-3-hydroxy-propyl)-3,4-dimethyl-piperidin-4-yl]-benzamide | 10 | 10 |

-continued

| Compound | Amount per capsule (mg) | Concentration by weight (%) |
|---|---|---|
| Starch | 45 | 45 |
| Microcrystalline cellulose | 35 | 35 |
| Polyvinylpyrrolidone (as 10% solution in water) | 4 | 4 |
| Sodium carboxymethyl starch | 4.5 | 4.5 |
| Magnesium stearate | 0.5 | 0.5 |
| talc | 1 | 1 |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granule so produced is dried at 50-60° C. and passed through a No. 18 mesh U.S. sieve. The sodium carboxymethyl starch, magnesium stearate and talc, previously passed through a No. 60 mesh U.S. sieve, are then added to the granule which, after mixing, is compressed on a tablet machine to yield a tablet weighing 100 mg.

Formulation 5

A tablet formula may be prepared using the ingredients below:

| Compound | Amount per capsule (mg) | Percent by weight (%) |
|---|---|---|
| Cyclohexyl-3-hydroxy-propyl)-3,4-dimethyl-piperidin-4-yl]-benzamide | 250 | 38 |
| Cellulose microcrystalline | 400 | 60 |
| Silicon dioxide fumed | 10 | 1.5 |
| Stearic acid | 5 | 0.5 |

The components are blended and compressed to form tablets each weighing 665 mg.

Formulation 6

Suspensions each containing 5 mg of medicament per 5 ml dose are made as follows:

| Compound | Amount per 5 mL suspension (ml) |
|---|---|
| Cyclohexyl-3-hydroxy-propyl)-3,4-dimethyl-piperidin-4-yl]-benzamide | 5 |
| Sodium carboxymethyl cellulose | 50 |
| Syrup | 1.25 |
| Benzoic acid solution | 0.10 |
| Flavor | q.v. |
| Color | q.v. |
| Water | q.s. to 5 mL |

The medicament is passed through a No. 45 mesh U.S. sieve and mixed with the sodium carboxymethylcellulose and syrup to form a smooth paste. The benzoic acid solution, flavor and color is diluted with some of the water and added to the paste with stirring. Sufficient water is then added to produce the required volume.

Formulation 7

An aerosol solution is prepared containing the following components:

| Compound | Concentration by weight (percent) |
|---|---|
| Cyclohexyl-3-hydroxy-propyl)-3,4-dimethyl-piperidin-4-yl]-benzamide hydrochloride | 0.25 |
| Ethanol | 29.75 |
| Propellant 22 (chlorodifluoromethane) | 70.0 |

The active compound is mixed with ethanol and the mixture added to a portion of the Propellant 22, cooled to −30° C. and transferred to a filling device. The required amount is then fed to a stainless steel container and diluted further with the remaining amount of propellant. The valve units are then fitted to the container.

Experimental Section

Intermediate 1

5-(8-Oxo-5,6,7,8-tetrahydro-naphthalen-2-yloxy)-nicotinamide

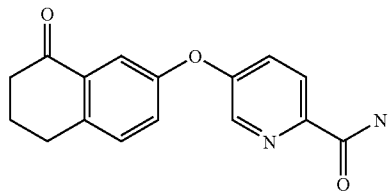

Combine 7-hydroxy-1-tetralone (J. Med. Chem. (1998), 41(7), 1068-1083), (3.37 g, 20.7 mmol), 6-chloronicotinamide (available from Aldrichj Chemical Company, Milwaukee, USA) (2.95 g, 18.8 mmol, $K_2CO_3$ (3.91 g, 28.3 mmol), DMA (dimethylacetamide) (45 ml) and toluene (25 ml) in a round bottom flask, equipped with Dean-Stark trap, condenser, and nitrogen inlet. Reflux the suspension for 2-3 hours before cooling to ambient temperature. Remove the solids via filtration, wash solids with EtOAc, and concentrate the filtrate/wash on a rotary evaporator. Dissolve the remaining oil in EtOAc, wash with water (2×) and brine, dry ($MgSO_4$) and concentrate. Triturate the resulting brown solid with boiling EtOAc, cool, and collect solid via filtration to give 4.76 g of the title compound as a yellow solid. Mass spectrum (ion spray): m/z=283 (M+1); $^1$HNMR (DMSO-$d_6$): 8.56 (s, 1H), 8.25 (d, 1H), 8.02 (s, 1H), 7.52 (s, 1H), 7.48 (s, 1H), 7.42 (d, 1H), 7.35 (d, 1H), 7.12 (d, 1H), 2.95 (t, 2H), 2.60 (t, 2H), 2.05 (m, 2H).

Intermediate 2

6-(5-Oxo-5,6,7,8-tetrahydro-naphthalen-2-yloxy)-nicotinamide

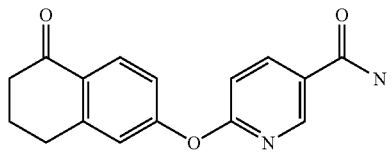

Using a method similar to Intermediate 1, using 6-hydroxy-1-tetralone (5.00 g, 30.8 mmol), 6-chloronicotinamide (4.38 g, 28.0 mmol) and K$_2$CO$_3$ (5.81 g, 42.0 mmol) gives the title compound (5.7 g) as a yellow solid. Mass spectrum (ion spray): m/z=283 (M+1); $^1$HNMR (DMSO-d$_6$): 8.63 (s, 1H), 8.29 (d, 1H), 8.06 (s, 1H), 7.90 (d, 1H), 7.51 (s, 1H), 7.16 (d, 1H), 7.12 (s, 1H), 7.09 (d, 1H), 2.92 (t, 2H), 2.58 (t, 2H), 2.03 (m, 2H).

Intermediate 3

6-(5-Oxo-5,6,7,8-tetrahydro-naphthalen-1-yloxy)-nicotinamide

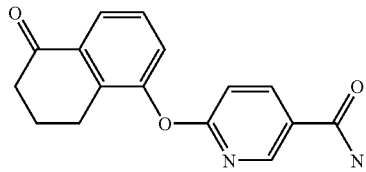

Using a method similar to Intermediate 1, using 5-hydroxy-1-tetralone (2.68 g, 16.5 mmol), 6-chloronicotinamide (2.34 g, 15.0 mmol) and K$_2$CO$_3$ (3.11 g, 22.5 mmol) gives the title compound (2.34 g) as a yellow solid. Mass spectrum (ion spray): m/z=283 (M+1); $^1$HNMR (DMSO-d$_6$): 8.55 (s, 1H), 8.27 (d, 1H), 8.02 (s, 1H), 7.80 (m, 1H), 7.48 (s, 1H), 7.43-7.37 (m, 1H), 7.14 (d, 1H), 2.66 (t, 2H), 2.58 (t, 2H), 1.96 (m, 2H).

Intermediate 4

6-(1-Oxo-indan-5-yloxy)-nicotinamide

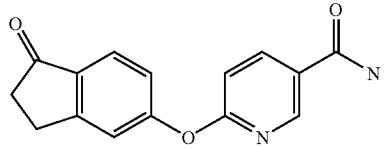

Using a method similar to Intermediate 1, using 5-hydroxy-1-indanone (2.44 g, 16.5 mmol), 6-chloronicotinamide (2.34 g, 15.0 mmol) and K$_2$CO$_3$ (3.11 g, 22.5 mmol) gives the title compound (1.90 g) as a yellow solid. Mass spectrum (ion spray): m/z=269 (M+1); $^1$HNMR (DMSO-d$_6$): 8.63 (s, 1H), 8.30 (d, 1H), 8.06 (s, 1H), 7.68 (d, 1H), 7.52 (s, 1H), 7.33 (s, 1H), 7.19 (d, 1H), 7.17 (d, 1H), 3.07 (t, 2H), 2.64 (t, 2H).

Intermediate 5

6-(1-Oxo-indan-4-yloxy)-nicotinamide

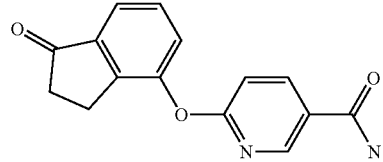

Using a method similar to Intermediate 1, using 4-hydroxy-1-indanone (2.44 g, 16.5 mmol), 6-chloronicotinamide (2.34 g, 15.0 mmol) and K$_2$CO$_3$ (3.11 g, 22.5 mmol) gives the title compound (1.22 g) as a yellow solid. Mass spectrum (ion spray): m/z=269 (M+1); $^1$HNMR (DMSO-d$_6$): 8.57 (s, 1H), 8.29 (d, 1H), 8.03 (s, 1H), 7.55-7.46 (M, 4H), 7.19 (d, 1H), 2.81 (t, 2H), 2.61 (t, 2H).

Intermediate 6

6-(3-Oxo-indan-5-yloxy)-nicotinamide

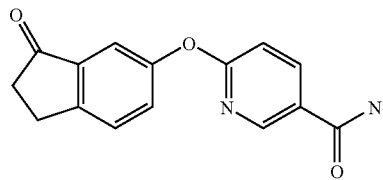

Using a method similar to Intermediate 1, using 6-hydroxy-1-indanone (J. Med. Chem. (1998), 41(7), 1068-1083) (2.07 g, 13.9 mmol), 6-chloronicotinamide (2.08 g, 13.3 mmol) and K$_2$CO$_3$ (2.75 g, 19.9 mmol) gives the title compound (1.36 g) as a yellow solid. Mass spectrum (ion spray): m/z=269 (M+1); $^1$HNMR (DMSO-d$_6$): 8.57 (s, 1H), 8.26 (d, 1H), 8.02 (s, 1H), 7.63 (d, 1H), 7.46 (m, 2H), 7.33 (s, 1H), 7.14 (d, 1H), 3.10 (t, 2H), 2.68 (t, 2H).

Intermediate 7

6-(7-Oxo-5,6,7,8-tetrahydro-naphthalen-2-yloxy)-nicotinamide

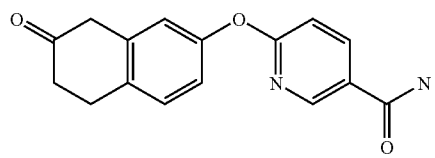

Combine 7-methoxy-2-tetralone (5.00 g, 28.3 mmol), thiophenol (3.39 g, 30.8 mmol), K$_2$CO$_3$ (213 mg, 1.54 mmol), and NMP (15 ml) in a round bottom flask equipped with nitrogen inlet. Heat at 180° C. for six hours and then stir at ambient temperature overnight. Treat reaction mixture with 1N aq. NaOH (20 ml) and water (20 ml) before extracting with Et$_2$O. Adjust the alkaline mixture to pH 4 with 1N aq. HCl and extract with Et$_2$O (3×). Dry (MgSO$_4$) the ethereal layer and concentrate to a yellow solid. Purify the crude material on silica gel, eluting with 5% EtOAc/DCM, to obtain 7-hydroxy-2-tetralone (1.88 g) as a light red solid. $^1$HNMR (CDCl$_3$): 7.09 (d, 1H), 6.69 (d, 1H), 6.62 (s, 1H), 4.86 (s, 1H), 3.53 (s, 2H), 2.99 (t, 2H), 2.54 (t, 2H).

Using a method similar to Example A, using 7-hydroxy-2-tetralone (1.88 g, 11.6 mmol), 6-chloronicotinamide (1.81 g, 11.6 mmol) and K$_2$CO$_3$ (2.40 g, 17.4 mmol) gives the title compound (742 mg), after purification on silica gel (30% THF/DCM), as an amber foam. Mass spectrum (ion spray): m/z=283 (M+1); $^1$HNMR (DMSO-d$_6$): 8.57 (s, 1H), 8.23 (d, 1H), 8.01 (s, 1H), 7.46 (s, 1H), 7.30 (d, 2H), 7.05 (d, 1H), 6.96 (m, 2H), 3.59 (s, 2H), 3.02 (t, 2H), 2.45 (t, 2H).

Intermediate 8

6-(6-Oxo-5,6,7,8-tetrahydro-naphthalen-2-yloxy)-nicotinamide

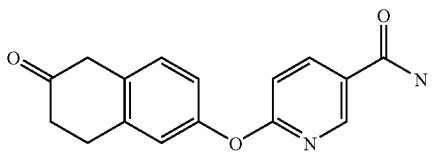

Using a method similar to Intermediate 1, using 6-hydroxy-2-tetralone (Journal of Organic Chemistry (1999), 64(26), 9719-9721.) (1.55 g, 9.55 mmol), 6-chloronicotinamide (1.49 g, 9.55 mmol) and K$_2$CO$_3$ (1.98 g, 14.3 mmol) gives the title compound (1.32 g), after purification on silica gel (50% THF/DCM), as an amber foam.

Mass spectrum (ion spray): m/z=283 (M+1); $^1$HNMR (DMSO-d$_6$): 8.59 (s, 1H), 8.23 (d, 1H), 8.01 (s, 1H), 7.47 (s, 1H), 7.19 (d, 2H), 7.07 (m, 2H), 6.97 (d, 1H), 3.59 (s, 2H), 3.01 (t, 2H), 2.43 (t, 2H).

Intermediate 9

6-(6-Oxo-5,6,7,8-tetrahydro-naphthalen-1-yloxy)-nicotinamide

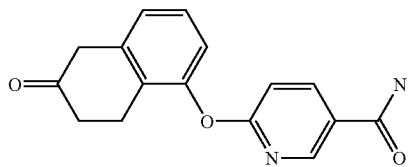

Using a method similar to Intermediate 1, using 5-hydroxy-2-tetralone (J. Med. Chem. (1978), 21(9), 913-22.) (1.98 g, 12.1 mmol), 6-chloronicotinamide (1.90 g, 12.1 mmol) and K$_2$CO$_3$ (2.52 g, 18.2 mmol) gives the title compound (1.80 g), after purification on silica gel (50% THF/DCM), as an amber foam. Mass spectrum (ion spray): m/z=283 (M+1); $^1$HNMR (DMSO-d$_6$): 8.55 (s, 1H), 8.24 (d, 1H), 8.00 (s, 1H), 7.46 (s, 1H), 7.25 (d, 2H), 7.08 (m, 2H), 7.00 (d, 1H), 3.64 (s, 2H), 2.77 (t, 2H), 2.34 (t, 2H).

Intermediate 10

6-(7-Oxo-5,6,7,8-tetrahydro-naphthalen-1-yloxy)-nicotinamide

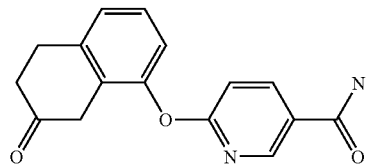

Using a method similar to Intermediate 1, using 8-hydroxy-2-tetralone (J. Med. Chem. (1978), 21(9), 913-22.) (1.55 g, 9.55 mmol), 6-chloronicotinamide (1.49 g, 9.55 mmol) and K$_2$CO$_3$ (1.98 g, 14.3 mmol) gives the title compound (652 mg),after purification on silica gel (50% THF/DCM), as an yellow foam. Mass spectrum (ion spray): m/z=283 (M+1); $^1$HNMR (CDCl$_3$): 8.52 (s, 1H), 8.18 (d, 1H), 7.30 (t, 1H), 7.17 (d, 1H), 7.02 (m, 2H), 5.92 (broad, 2H), 3.42 (s, 2H), 3.15 (t, 2H), 2.61 (t, 2H).

Intermediate 11

6-(3,3-Dimethyl-1-oxo-indan-5-yloxy)-nicotinamide

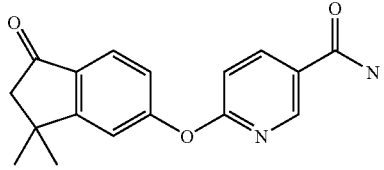

Add drop-wise a solution of BBr$_3$ (8.14 g, 32.5 mmol) dissolved in DCM (10 ml) to a solution of 5-Methoxy-3,3-dimethyl-1-indanone (U.S. Pat. No. 6,313,107) (2.47 g, 13.0 mmol) dissolved in DCM (20 ml) and cooled to −78° C. under nitrogen. After stirring at −78° C. for one hour, remove the cold bath and stir at ambient temperature overnight. Cool the reaction mixture to −78° C. and quench with saturated aqueous NaHCO$_3$. Dilute mixture with water and extract with EtOAc (2×). Wash extracts with water and brine, dry (MgSO$_4$) and concentrate on rotary evaporator to a dark amber solid. Triturate the solid with boiling Et$_2$O, cool, and collect 5-hydroxy-3,3-dimethyl-1-indanone (1.54 g) as a tan solid.

Add NaH (60%/oil, 196 mg, 4.91 mmol) to a mixture of 5-hydroxy-3,3-dimethyl-1-indanone (787 mg, 4.46 mmol) and DMSO (10 ml) stirring at ambient temperature under nitrogen. After ten minutes, add 6-chloronicotinonitrile (619 mg, 4.46 mmol) dissolved in DMSO (10 ml) and stir the resulting mixture at 60° C. overnight. Quench the reaction with saturated aqueous NH$_4$Cl and extract with EtOAc (2×). Wash extract with water and brine, dry (MgSO$_4$) and concentrate on rotary evaporator to a brown, oily solid. Purify on silica gel (10% EtOAc/DCM) to give 877 mg of 6-(3,3-Dimethyl-1-oxo-indan-5-yloxy)-nicotinonitrile as a yellow solid.

Add 30% aqueous H$_2$O$_2$ (3.15 ml) to a suspension of 6-(3,3-Dimethyl-1-oxo-indan-5-yloxy)-nicotinonitrile (877 mg, 3.15 mmol), K$_2$CO$_3$ (218 mg, 1.57 mmol) and DMSO (10 ml) stirring under nitrogen at ambient temperature. After four hours, dilute the reaction mixture with water (100 ml) and extract with EtOAc (2×). Wash the extract with water and brine, dry (MgSO$_4$) and concentrate on rotary evaporator to yield 876 mg of the title compound as an off-white solid. Mass spectrum (ion spray): m/z=297 (M+1); $^1$HNMR (CDCl$_3$): 8.62 (s, 1H), 8.24 (d, 1H), 7.75 (d, 1H), 7.24 (s, 1H), 7.14 (d, 1H), 7.07 (d, 1H), 5.91 (broad, 2H), 2.63 (s, 2H), 1.43 (s, 6H).

Intermediate 12

6-(4-Methyl-1-oxo-indan-5-yloxy)-nicotinamide

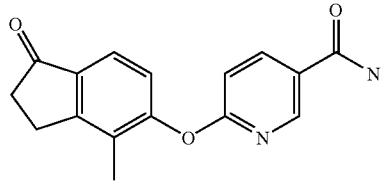

Add drop-wise a solution of BBr$_3$ (14.8 g, 59.1 mmol) dissolved in DCM (50 ml) to a solution of 5-Methoxy-4-methyl-1-indanone (Tetrahedron (1970), 26(11), 2599-608) (4.17 g, 23.6 mmol) dissolved in DCM (50 ml) and cooled to −78° C. under nitrogen. After stirring at −78° C. for one hour, remove the cold bath and stir at ambient temperature overnight. Cool the reaction mixture to −78° C. and quench with saturated aqueous NaHCO$_3$. Dilute mixture with water and extract with EtOAc (2×). Wash extracts with water and brine, dry (MgSO$_4$) and concentrate on rotary evaporator to give 5-hydroxy4-methyl-1-indanone (2.60 g) as an amber solid.

Add K$_2$CO$_3$ (1.24 g, 9.00 mmol) to a mixture of 5-hydroxy-4-methyl-1-indanone (973 mg, 6.00 mmol), 6-chloronicotinonitrile (831 mg, 6.00 mmol) and DMSO (15 ml) stirring at ambient temperature under nitrogen. Heat the mixture at 55° C. for three days. Quench the reaction with saturated aqueous NH$_4$Cl and extract with EtOAc (2×). Wash extract with water and brine, dry (MgSO$_4$) and concentrate on rotary evaporator to a brown foam. Purify on silica gel (10% EtOAc/DCM) to give 1.22 g of 6-(4-Methyl-1-oxo-indan-5-yloxy)-nicotinonitrile as a yellow solid.

Add 30% aqueous H$_2$O$_2$ (3.6 ml) to a suspension of 6-(4-Methyl-1-oxo-indan-5-yloxy)-nicotinonitrile (1.22 mg, 4.61 mmol), K$_2$CO$_3$ (319 mg, 2.31 mmol) and DMSO (20 ml) stirring under nitrogen at ambient temperature. After 2.5 hours, dilute the reaction mixture with water (100 ml) and extract with EtOAc (2×). Wash the extract with water and brine, dry (MgSO$_4$) and concentrate on rotary evaporator to yield 1.07 g of the title compound as a yellow solid. Mass spectrum (ion spray): m/z=283 (M+1); $^1$HNMR (DMSO-d$_6$): 8.55 (s, 1H), 8.27 (d, 1H), 8.01 (s, 1H), 7.51 (d, 1H), 7.47 (s, 1H), 7.17 (d, 1H), 7.12 (d, 1H), 3.03 (t, 2H), 2.66 (t, 2H), 2.07 (s, 3H).

Intermediate 13

6-(5-Chloro-5,6,7,8-tetrahydro-naphthalen-2-yloxy)-nicotinamide

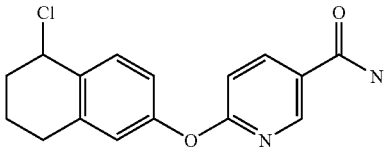

Add NaBH$_4$ (79.4 mg, 2.10 mmol) to a suspension of 6-(5-Oxo-5,6,7,8-tetrahydro-naphthalen-2-yloxy)-nicotinamide (Intermediate 2, 395 mg, 1.40 mmol) in MeOH (10 ml), stirring at ambient temperature. After 24 hours, concentrate the reaction mixture and redissolve in EtOAc. Wash with 5% aqueous KOH, water, and brine before drying (MgSO$_4$) and concentrating to a solid. Purify material on silica gel (50% THF/DCM) to give 6-(5-Hydroxy-5,6,7,8-tetrahydro-naphthalen-2-yloxy)-nicotinamide (288 mg) as a white solid. Mass spectrum (ion spray): m/z=285 (M+1); $^1$HNMR (CDCl$_3$): 8.58 (s, 1H), 8.16 (d, 1H), 7.50 (d, 1H), 6.97 (m, 2H), 6.88 (s, 1H), 5.95 (broad, 2H), 4.80 (t, 1H0, 2.82-2.74 (m, 2H), 2.03-1.77 (m, 4H), 1.68 (s, 1H).

Charge flask with 6-(5-Hydroxy-5,6,7,8-tetrahydro-naphthalen-2-yloxy)-nicotinamide (288 mg, 1.01 mmol) and SOCl$_2$ (5 ml) and heat at 50° C. under nitrogen atmosphere with stirring. After 3.5 hours, concentrate on rotary evaporator to give the title compound as a yellow oil. Due to instability, use this material without purification.

Intermediate 14

6-(1-Chloro-indan-5-yloxy)-nicotinamide

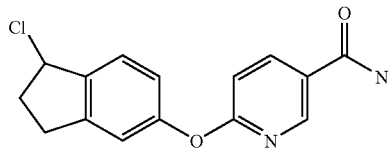

Using a method similar to intermediate 13, using 6-(1-Oxo-indan-5-yloxy)-nicotinamide (Intermediate 4, 500 mg, 1.86 mmol) and NaBH$_4$ (105 mg, 2.79 mmol) gives 6-(1-Hydroxy-indan-5-yloxy)-nicotinamide (346 mg) as a white solid. Mass spectrum (ion spray): m/z=271 (M+1); $^1$HNMR (DMSO-d$_6$): 8.58 (s, 1H), 8.22 (d, 1H), 8.00 (s, 1H), 7.45 (s, 1H), 7.34 (d, 1H), 7.03 (d, 1H), 6.97 (s, 1H), 6.93 (d, 1H), 5.03 (t, 1H), 2.93-2.86 (m, 1H), 2.73-2.66 (m, 1H), 2.38-2.30 (m, 1H), 1.84-1.72 (m, 1H), 1.33 (s, 1H). Convert 6-(1-Hydroxy-indan-5-yloxy)-nicotinamide to the title compound using a method similar to intermediate 13. Due to instability, use this material without purification.

Intermediate 15

6-(2-Amino-indan-5-yloxy)-nicotinamide

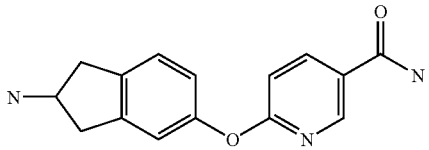

Reflux a mixture of 5-methoxy-2-aminoindane prepared according to Hajduk, Philip J., et al.; *J. Med. Chem.* 1999, 42, 3852-3859. (2.76 g, 16.9 mmol) and 48% aqueous HBr for three hours before cooling and concentrating on rotary evaporator. Treat the crude 5-hydroxy-2-aminoindane with THF (50 ml), 1M aqueous K$_2$CO$_3$ (42 ml), and Boc$_2$O (4.05 g, 18.6 mmol) and stir at ambient temperature overnight. Pour mixture into saturated aqueous NH$_4$Cl and extract with EtOAc (2×). Wash combined extracts with brine, dry (MgSO$_4$) and concentrate to a brown foam. Purify on silica gel (10% EtOAc/DCM) to give N-Boc-5-hydroxy-2-aminoindane (2.50 g) as a tan solid.

Combine N-Boc-5-hydroxy-2-aminoindane (2.50 g, 10.0 mmol), 6-chloronicotinamide (1.49 g, 9.55 mmol, $K_2CO_3$ (1.90 g, 14.3 mmol), DMA (25 ml) and toluene (20 ml) in a round bottom flask, equipped with Dean-Stark trap, condenser, and nitrogen inlet. Reflux the suspension for two hours before cooling to ambient temperature. Remove the solids via filtration, wash solids with EtOAc, and concentrate the filtrate/wash on a rotary evaporator. Dissolve the remaining oil in EtOAc, wash with water (2×) and brine, dry ($MgSO_4$) and concentrate. Purify the material on silica gel (20% THF/DCM) to give [5-(5-carbamoyl-pyridin-2-yloxy)-indan-2-yl]-carbamic acid tert-butyl ester (870 mg) as a light yellow solid.

Add TFA (5.37 g, 47.1 mmol) to a suspension of [5-(5-carbamoyl-pyridin-2-yloxy)-indan-2-yl]-carbamic acid tert-butyl ester (870 mg, 2.35 mmol) in DCM (30 ml) and stir at ambient temperature overnight. Concentrate mixture on rotary evaporator and purify on cation exchange column (5 g, Varian) to give the title compound (479 mg) as a white solid. Mass spectrum (ion spray): m/z=270 (M+1); $^1$HNMR (MeOH-$d_4$): 8.61 (s, 1H), 8.22 (d, 1H), 7.24 (d, 1H), 6.98 (s, 1H), 6.94 (d, 1H), 6.90 (d, 1H), 3.80 (m, 1H), 3.18 (m, 2H), 2.72 (m, 2H).

Intermediate 16

6-(2-Amino-indan-4-yloxy)-nicotinamide

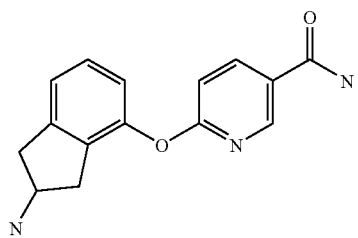

Using a method similar to intermediate 15, using 4-methoxy-2-aminoindane (J. Med. Chem. (1985), 28(4), 515-18, 6.64 g, 40.6 mmol) gives the title compound (2.26 g) as a white solid. Mass spectrum (ion spray): m/z=270 (M+1); $^1$HNMR (CDCl$_3$): 8.54 (s, 1H), 8.14 (d, 1H), 7.23 (t, 1H), 7.12 (d, 1H), 6.93 (m, 2H), 6.19 (br s, 2H), 3.81 (m, 1H), 3.22 (dd, 1H), 2.94 (dd, 1H), 2.71 (dd, 1H), 2.44 (dd, 1H).

Intermediate 17

6-(1-Aminoethyl-indan-5-yloxy)-nicotinamide

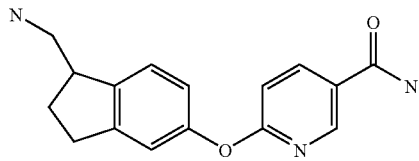

Dissolve sodium metal (1.51 g, 66.0 mmol) in abs. EtOH (50 ml) and DME (100 ml) and add the resulting solution drop-wise to a mixture of 5-methoxy-1-indanone (3.57 g, 22.0 mmol), tosylmethyl isocyanide (6.45 g, 33.0 mmol) and DME (150 ml) cooled to −5° C. under nitrogen. After addition is complete (ca. one hour), allow mixture to slowly obtain ambient temperature and stir overnight. After cooling to 0° C., carefully quench with water and extract with EtOAc (2×). Wash the combined extracts with water and brine, dry ($MgSO_4$) and concentrate. Purify on silica gel (toluene) to give 5-methoxy-indan-1-carbonitrile (2.55 g) as a yellow oil. $^1$HNMR (CDCl$_3$): 7.31 (d, 1H), 6.80 (m, 2H), 4.05 (t, 1H), 3.80 (s, 3H), 3.07 (m, 1H), 2.93 (m, 1H), 2.56 (m, 1H), 2.39 (m, 1H).

Subject a mixture of 5-methoxy-indan-1-carbonitrile (1.49 g, 8.60 mmol), Raney nickel (500 mg), anhydrous ammonia (10 ml), and abs. EtOH (50 ml) to 900 lbs of hydrogen gas and beat at 80° C. for five hours. After cooling and purging with nitrogen, remove the catalyst via filtration and concentrate the filtrate on a rotary evaporator. Suspend this material in DCM (30 ml) and cool to −78° C. before adding a solution of BBr$_3$/DCM (8 ml) drop-wise. After the addition is complete, allow the mixture to warm to ambient temperature and stir for 2.5 hours. Cool again to −78° C. and carefully quench with MeOH before concentrating. Treat this material with THF (35 ml), 1M aqueous $K_2CO_3$ (21.5 ml), and Boc$_2$O (2.25 g, 10.3 mmol) and stir vigorously at ambient temperature overnight. Pour the reaction mixture into saturated aqueous NH$_4$Cl and extract with EtOAc (2×). Wash combined extracts with brine, dry ($MgSO_4$) and concentrate to a yellow foam. Purify on silica gel (10% EtOAc/DCM) to obtain N-Boc-1-aminomethyl-indan-5-ol (945 mg) as a yellow foam. $^1$HNMR (CDCl$_3$): 6.98 (d, 1H), 6.85 (s, 1H), 6.73 (s, 1H), 6.65 (d, 1H), 4.69 (br s, 1H), 3.45 (m, 1H), 3.22 (m, 2H), 2.88-2.72 (m 2H), 2.20 (m, 1H), 1.78 (m, 1H), 1.45 (s, 9H).

Heat a mixture of N-Boc-1-aminomethyl-indan-5-ol (1.13 g, 4.29 mmol), 6-chloronicotinamide (671 mg, 4.29 mmol, $K_2CO_3$ (889 mg, 6.43 mmol), and DMSO (10 ml) at 100° C. for 19 hours. Pour the reaction mixture into saturated aqueous NH$_4$Cl and extract with EtOAc. Wash extract with brine, dry ($MgSO_4$) and concentrate to a brown foam. Purify on silica gel (30% EtOAc/DCM) to obtain [5-(5-carbamoyl-pyridin-2-yloxy)-indan-1-ylmethyl]-carbamic acid tert-butyl ester (847 mg) as a light yellow solid. $^1$HNMR (CDCl$_3$): 8.61 (s, 1H), 8.17 (d, 1H), 7.24 (d, 1H), 7.00 (s, 1H), 6.95 (m, 3H), 6.03 (br s, 2H), 4.65 (br s, 1H), 3.48 (m, 1H), 3.31 (m, 2H), 2.98-2.83 (m, 2H), 2.30 (m, 1H), 1.90 (m, 1H), 1.45 (s, 9H).

Add TFA (6.54 g, 57.4 mmol) to a suspension of [5-(5-carbamoyl-pyridin-2-yloxy)-indan-1-ylmethyl]-carbamic acid tert-butyl ester (1.05 g, 2.87 mmol) in DCM (20 ml) and stir at ambient temperature for four hours. Concentrate mixture on rotary evaporator and purify on cation exchange column (10 g, Varian) to give the title compound (519 mg) as a white solid. Mass spectrum (ion spray): m/z=284 (M+1); $^1$HNMR (DMSO-$d_6$): 8.58 (s, 1H), 8.21 (d, 1H), 8.00 (br s, 1H), 7.44 (br s, 1H), 7.27 (d, 1H), 7.01 (d, 1H), 6.96 (s, 1H), 6.87 (d, 1H), 3.05 (m, 1H), 2.84 (m, 2H), 2.77 (m, 1H), 2.62 (m, 1H), 2.18 (m, 1H), 1.82 (m, 1H), 1.71 (br s, 2H).

Intermediate 18

6-(3-Aminomethyl-indan-5-yloxy)-nicotinamide

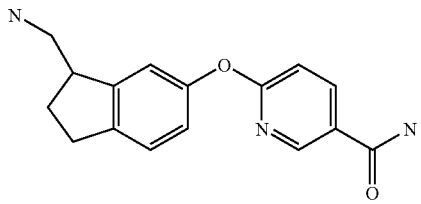

Using a method similar to intermediate 17, using 6-methoxy-1-indanone gave the title compound as a light yellow solid. Mass spectrum (ion spray): m/z=284 (M+1); $^1$HNMR (CDCl$_3$): 8.59 (s, 1H), 8.15 (d, 1H), 7.25 (d, 1H), 7.00 (s, 1H), 6.94 (d, 2H), 6.12 (br s, 2H), 3.23 (m, 1H), 2.99-2.84 (m, 4H), 2.33 (m, 1H), 1.89 (m, 1H), 1.40 (br s, 2H).

Intermediate 19

6-(8-Aminomethyl-5,6,7,8-tetrahydro-naphthalen-2-yloxy)-nicotinamide

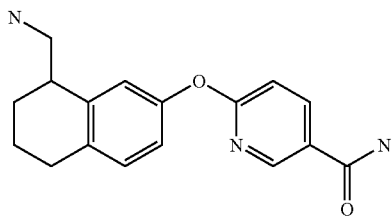

Using a method similar to intermediate 17, using 6-methoxy-1-tetralone gave the title compound as a light amber solid. Mass spectrum (ion spray): m/z=298 (M+1); $^1$HNMR (CDCl$_3$): 8.58 (s, 1H), 8.15 (d, 1H), 7.13 (d, 1H), 6.99 (s, 1H), 6.95 (d, 1H), 6.90 (d, 1H), 6.01 (br s, 2H), 2.93 (d, 2H), 2.81 (m, 1H), 2.77 (m, 2H), 1.91-1.70 (m, 8H).

Intermediate 20

6-(5-Aminomethyl-5,6,7,8-tetrahydro-naphthalen-1-yloxy)-nicotinamide

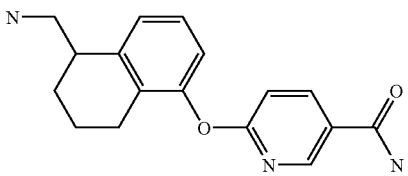

Using a method similar to intermediate 17, using 5-methoxy-1-tetralone gave the title compound as a light tan solid. Mass spectrum (ion spray): m/z=298 (M+1); $^1$HNMR (CDCl$_3$): 8.57 (s, 1H), 8.16 (d, 1H), 7.23-7.12 (m, 2H), 6.94-6.90 (m, 2H), 5.83 (br s, 2H), 3.03-2.82 (m, 3H), 2.62-2.47 (m, 2H), 1.88-1.66 (m, 4H), 1.34 (br s, 2H).

Intermediate 21

6-(5-Aminomethyl-5,6,7,8-tetrahydro-naphthalen-2-yloxy)-nicotinamide

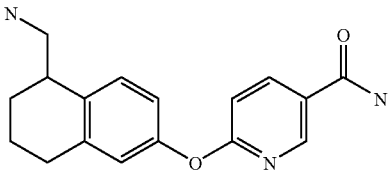

Using a method similar to intermediate 17, using 6-methoxy-1-tetralone gave the title compound as a white foam. Mass spectrum (ion spray): m/z=298 (M+1); $^1$HNMR (CDCl$_3$): 8.59 (s, 1H), 8.16 (d, 1H), 7.25 (d, 1H), 6.94 (d, 1H), 6.90 (d, 1H), 6.86 (s, 1H), 5.92 (br s, 2H), 3.00-2.90 (m, 2H), 2.85-2.79 (m, 1H), 2.78-2.73 (m, 2H), 1.89-1.69 (m, 4H), 1.34 (br s, 2H).

Intermediate 22

[5-(5-Cyano-pyridin-2-yloxy)-1,2,3,4-tetrahydro-naphthalen-1-ylmethyl]-carbamic acid tert-butyl ester

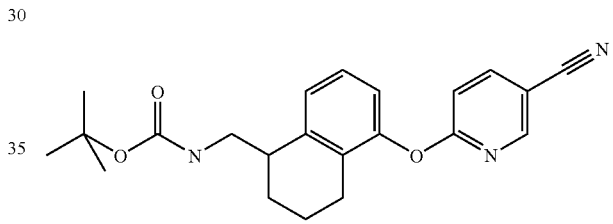

Combine N-Boc-1-aminomethyl-indan-5-ol (described in prep for Intermediate 17) (5.80 g, 20.9 mmol), 6-chloronicotinonitrile (2.89 g, 20.9 mmol), K$_2$CO$_3$ (4.33 g, 31.3 mmol) and DMA (50 ml) and heat at 100 C for 4.5 hours. After cooling, pour the reaction mixture into saturated, aqueous NH$_4$Cl and extract with EtOAc (2×). Wash extract with brine, dry (MgSO$_4$) and concentrate to a brown foam. Purify on silica gel (30% EtOAc/Hexane) to obtain the title compound (7.88 g) as a light yellow foam. Mass spectrum (ion spray): m/z=380 (M+1); $^1$HNMR (CDCl$_3$): 8.45 (s, 1H), 7.90 (d, 1H), 7.25-7.18 (m, 2H), 6.99 (d, 1H), 6.91 (d, 1H), 4.69 (m, 1H), 3.51-3.25 (m, 2H), 3.03 (m, 1H), 2.62-2.39 (m, 1H), 1.83-1.68 (m, 4H), 1.46 (s, 9H).

Intermediate 23

4-(1-Oxo-indan-5-yloxy)-benzonitrile

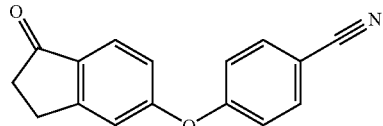

Combine 5-Hydroxyindanone (2.0 g, 13.50 mmol), 4-Fluorobenzonitrile (1.55 g, 12.80 mmol), K$_2$CO$_3$ (2.65 g, 19.20 mmol) and toluene/DMA (20 ml/40 ml), reflux under Nitrogen using a Dean-Stark Trap. After 4.0 hours, cool the reaction to room temperature and add Ethyl Acetate. Wash several times with 10% LiCl and Brine solution, then dry the organic layer over $Na_2SO_4$ follow by concentration. Flash chromatograph using 4/1 then 1/1 hexanes/ethyl acetate eluant to afford 1.64 g, 6.57 mmol (49% yield) of the title compound: $^1$H NMR (500 MHz, $CDCl_3$); 2.7-2.8 (2H, m), 3.1-3.2 (2H, m), 7.0-7.1 (2H, m), 7.1-7.2 (2H, m), 7.6-7.7 (2H, m), 7.7-7.8 (1H, m); MS m/z 250 (M+1).

Intermediate 24

4-(1-Oxo-indan-5-yloxy)-benzamide

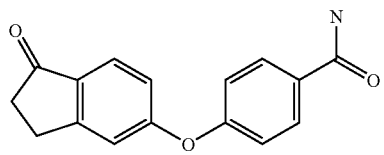

Combine 4-(1-Oxo-indan-5-yloxy)-benzonitrile (1.64 g, 6.58 mmol), tert-butyl alcohol (50 ml), and grounded KOH (1.85 g, 32.89 mmol) at room temperature under nitrogen atmosphere. Stir the reaction for 24 hours then concentrate under reduced pressure. Add Ethyl acetate to the reaction mixture and wash with brine. Dry the organic layer over $Na_2SO_4$. A yellow-orange solid precipitates out to afford 101.0 mg, 0.38 mmol (5.7% yield) of the title compound: No Characterization—Characterized by sequential reaction.

Intermediate 25

4-(5-Oxo-5,6,7,8-tetrahydro-naphthalen-2-yloxy)-benzonitrile

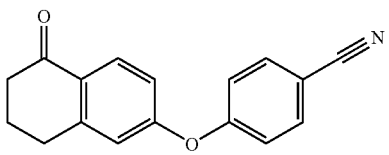

Combine 6-Hydroxytetralone (4.42 g, 27.24 mmol), 4-Fluorobenzonitrile (3.0 g, 24.76 mmol), $K_2CO_3$ (5.1 g, 37.14 mmol) and toluene/DMA (30 ml/90 ml), then reflux under Nitrogen using a Dean Stark Trap. After 4 hours, cool the reaction to room temperature and add to a separatory funnel. Add Ethyl acetate and wash the organic layer several times with water, then a brine solution, and dry the organic layer over $Na_2SO_4$. Flash chromatograph using 4/1 hexanes/ethyl acetate eluant to afford 5.34 g, 20.3 mmol (82% yield) of the title compound: $^1$H NMR (500 MHz, $CDCl_3$); 2.1-2.2 (2H, m), 2.6-2.7 (2H, m), 2.9-3.0 (2H, m), 6.85 (1H, s), 6.9-7.0 (1H, m), 7.05-7.15 (2H, m), 7.6-7.7 (2H, m), 8.05-8.10 (1H, m); MS m/z 264 (M+1).

Intermediate 26

4-(5-Oxo-5,6,7,8-tetrahydro-naphthalen-2-yloxy)-benzamide

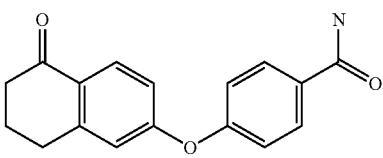

Combine 4-(5-Oxo-5,6,7,8-tetrahydro-naphthalen-2-yloxy)-benzonitrile (5.34, 20.3 mmol), t-butyl alcohol (100 ml), and KOH (5.7 g, 101.5 mmol). After the reaction stirs for 72 hours at room temperature, concentrate under reduced pressure and then add ethyl acetate. Wash the organic phase with water, a brine solution, and then dry the organic layer over $Na_2SO_4$. Flash chromatograph using 2/1 $CH_2Cl_2$/ethyl acetate eluent to afford 5.20 g, 18.5 mmol (91% yield) of the title compound: $^1$H NMR (500 MHz, $CDCl_{-3}$); 2.1-2.2 (2H, m), 2.6-2.7 (2H, m), 2.9-3.0 (2H, m), 5.6-6.2 9 (2H, br m), 6.85 (1H, s), 6.9-7.0 (1H, m), 7.05-7.15 (2H, m), 7.8-7.9 (2H, m), 8.05-8.10 (1H, m); MS m/z 284 (M+3).

Intermediate 27

6-Methoxy-1-oxo-indan-2-carboxylic acid methyl ester

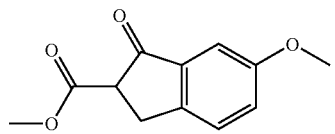

Combine NaH (5.4 g, 122.1 mmol), THF anhydrous (150 mL), and dimethylcarbonate (6.6 mL, 81.3 mmol). While refluxing the reaction under a nitrogen atmosphere, add dropwise 5-Methoxyindanone (3.46 g, 21.33 mmol) over one hour. After the reaction mixture refluxes for 12 hours, quench using Acetic acid and then add Ethyl acetate to the reaction mixture in a separatory funnel. Wash the organic layer several times with water and dry the organic layer over $Na_2SO_4$ followed by concentration under reduced pressure. Flash Chromatograph using 1:1 Hexanes:Ethyl acetate to afford 3.14 g, 14.3 mmol (67% yield) of the title compound: $^1$H NMR (500 MHz, $CDCl_3$); 3.3-3.4 (1H, dd), 3.5-3.6 (1H, dd), 3.7-3.8 (1H, m), 3.8 (3H, s), 3.9 (3H, s), 6.8-7.0 (2H, m), 7.7-7.8 (1H, m); TLC 2:1 Hexanes:Ethyl acetate $R_f$=0.4.

Intermediate 28

5-Methoxy-indan-2-carboxylic acid methyl ester

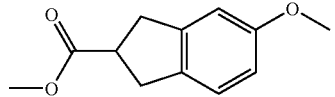

Combine in a Parr shaker 6-Methoxy-1-oxo-indan-2-carboxylic acid methyl ester (3.14 g, 14.25 mmol), added acetic acid (150 mL), perchloric acid (0.8 mL) and 5% Pd—C (0.14 mmol). After the reaction has been on the parr shaker under 40 atm of H$_2$ pressure at room temperature for 12 hours, filter the reaction mixture through a pad of Celite using ethyl acetate eluent. Then add the filtrate to a separatory funnel and wash with water then brine, and dry the organic layer over Na$_2$SO$_4$. After concentrating under reduced pressure, flash Chromatograph using 8:1 Hexanes:Ethyl acetate to afford 1.9 g, 9.21 mmol (65% yield) of the title compound as a clear oil: $^1$H NMR (500 MHz, CDCl$_3$); 3.2-3.4 (5H, m), 3.7 (3H, s), 3.8 (3H, s), 6.7-6.8 (2H, m), 7.1-7.2 (1H, m); TLC 1:1 Hexanes:Ethyl acetate R$_f$=0.6.

Intermediate 29

(5-Methoxy-indan-2-yl)-methanol

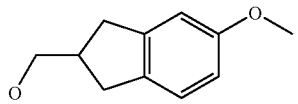

Combine 5-Methoxy-indan-2-carboxylic acid methyl ester (Intermediate 28, 1.90 g, 9.21 mmol), LiAlH$_4$ (0.70 g, 18.43 mmol), and THF anhydrous (60 ml). After the reaction stirs under a nitrogen atmosphere at room temperature for 2 hours, quench the reaction mixture with 5 mL of deionized water. Filter the mixture through a pad of Celite using EtOAc eluent, and wash the organic layer with brine, and dry over Na$_2$SO$_4$. After concentrating under reduced pressure, the flash chromatograph the mixture to afford 1.43 g, 8.0 mmol (87% yield) of the title compound as a clear oil: $^1$H NMR (500 MHz, CDCl$_3$); 1.4-1.6 (1H, br s), 2.6-2.8 (3H, m), 2.9-3.2 (2H, m), 3.6-3.7 (2H, m), 3.8 (3H, s), 6.7-6.8 (2H, m), 7.1-7.2 (1H, m); TLC 1:1 Hexanes:Ethyl acetate R$_f$=0.4.

Intermediate 30

2-Hydroxymethyl-indan-5-ol

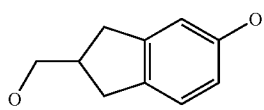

Combine (5-Methoxy-indan-2-yl)-methanol (117.0 mg, 0.65 mmol), and 48% HBr(aq). After the reaction refluxes for 30 minutes, cool to room temperature and extract the product with ethyl acetate. Wash with brine and dry over Na$_2$SO$_4$. After concentrating the organic layer under reduced pressure, flash chromatograph using 2/1 Hexanes/Ethyl acetate eluent to afford 67.3 mg, 0.41 mmol (63% yield) of the title compound: $^1$H NMR (500 MHz, CDCl$_3$); 2.6-2.8 (3H, m), 2.9-3.1 (2H, m), 3.6-3.8 (2H, m), 6.6-6.8 (2H, m), 7.0-7.1 (1H, m); TLC 1:1 Hexanes:Ethyl acetate R$_f$=0.3.

Intermediate 31

6-(2-Hydroxymethyl-indan-5-yloxy)nicotinamide

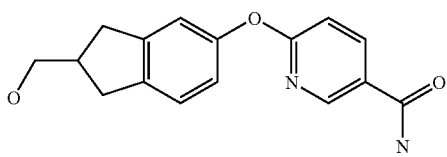

Combine in a round bottom flask equipped with a stir, Dean Stark Trap filled with toluene, and reflux condenser 2-Hydroxymethyl-indan-5-ol (630.2 mg, 3.84 mmol), K$_2$CO$_3$ (690.0 mg, 5.0 mmol), 6-Chloronicotinamide (600.0 mg, 3.84 mmol) and a solution of DMA:Toluene (15:5 mL). After the reaction refluxes under nitrogen atmosphere for 5 hours, concentrate under reduced pressure and then add ethyl acetate. Wash the organic layer several times with water, then brine, and dry over Na$_2$SO$_4$. After concentrating the reaction mixture under reduced pressure, flash chromatograph using 20% THF, 7% 1N NH$_3$-MeOH, 73% DCM eluent to afforded 481.1 mg, 1.69 mmol (44% yield) of the title compound: $^1$H NMR (500 MHz, CDCl$_3$); 1.8-2.2 (4H, m), 2.6-2.8 (3H, m), 3.6-3.8 (2H, br d), 3.9-4.0 (1H, m), 6.1-6.6 (2H, br d), 6.8-7.0 (3H, m), 7.2-7.3 (1H, m), 8.1-8.2 (1H, m), 8.6 (1H, s); MS m/z 285 (M+1).

Intermediate 32

6-(2-Formyl-indan-5-yloxy)-nicotinamide

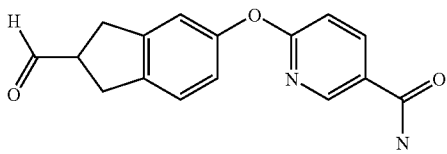

Combine DCM (3 mL) and oxalyl chloride (41 uL) under nitrogen atmosphere at −78° C., and then add DMSO (49 uL) in DCM (2 mL). After the solution stirs for 15 minutes, add 6-(2-Hydroxymethyl-indan-5-yloxy)nicotinamide (33.1 mg, 0.116 mmol) in DCM (2 mL). After 15 minutes, add Et$_3$N (97 uL, 0.70 mmol). After the reaction gradually warms to room temperature over the next 5 hours, then quench with water. Add the mixture to a separatory funnel and extract the product with DCM. Wash the organic phase with brine and then dry over Na$_2$SO$_4$. After concentrating under reduced pressure, flash chromatograph using 10% THF/CH$_2$Cl$_2$ eluent affords 27.4 mg, 0.10 mmol (84% yield) of the title compound: $^1$H NMR (500 MHz, CDCl$_3$); 3.1-3.2 (2H, m), 3.2-3.4 (3H, m), 6.8-7.0 (4H, m), 7.1-7.3 (1H, m), 8.8-8.9 (1H, m), 8.4 (1H, s), 9.7 (1H, s); TLC 1:6 THF:CH$_2$Cl$_2$ R$_f$=0.7.

Intermediate 33

2-Tert-butyldimethylsilyloxyphenethyl amine

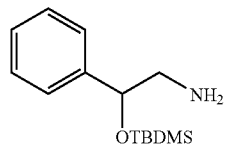

To a solution of TBDMSCl (2.1 equiv) and DBU (2.1 equiv) in CH$_2$Cl$_2$ (0.5 M), add the alcohol (1 equiv). Stir the resulting reaction mixture under N$_2$ at room temperature 3 hours. Wash the reaction mixture with water, 0.5% HCl and saturated aqueous solution of NaHCO$_3$, separate the organic layer, and dry over anhydrous NaSO$_4$. Evaporation of the solvent yields a residue which is purified by flash chromatography using EtOAc/CH$_2$Cl$_2$/2M NH$_3$ in methanol, 0.6/0.35/0.05) to afford the title compound. 92% Yield.

$^1$H NMR (CHCl$_3$-d$_3$) δ: 7.29 (s, 5H), 4.65 (t, 1H, J=5.4 Hz), 2.83 (d, 2H, J=5.4 Hz), 1.40 (bs, 2H), 0.91 (s, 9H), 0.05 (s, 3H), −0.10 (s, 3H).

Intermediate 34

6-(5-[2-(tert-Butyl-dimethyl-silanyloxy)-2-phenyl-ethylamino]-5,6,7,8-tetrahydro-naphthalen-2-yloxy}-nicotinamide

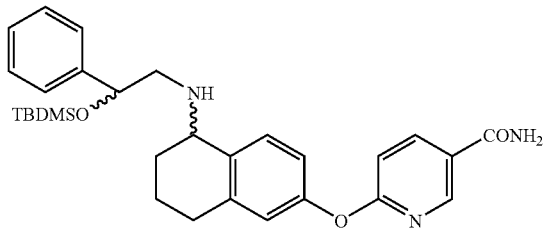

The compound is prepared according to General Procedure IV and used without further purification in the synthesis of example 219.

Intermediate 35

Benzyl-(2-methoxy-6,7,8,9-tetrahydro-5H-benzocyclohepten-6-yl)-amine

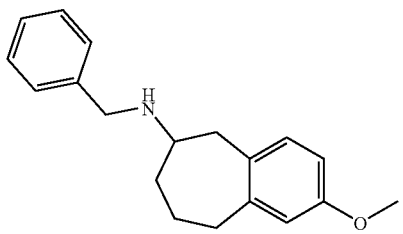

Dissolve 2-Methoxy-5,7,8,9-tetrahydro-benzocyclohepten-6-one (prepared according to JCS Perkin Trans. 1, 1992, 1475-1481, 83 mg, 0.44 mmol) in 1 mL of 19:1 methanol/acetic acid as solvent, and treat the solution with benzylamine (60 uL, 65 mg, 0.60 mmol) and NaCNBH$_3$ (80 mg, 1.27 mmol). Agitate the reaction mixture overnight, then dilute with 25 mL dichloromethane. Wash the organic layer with 25 mL 10% aqueous potassium carbonate solution, the 25 mL brine, dry over MgSO$_4$ and evaporate to yield 103 mg product, used in subsequent chemistry without further purification; 80% crude yield.

$^1$H NMR (CDCl$_3$): 7.2-7.4: m, 5H; 7.15: m, 1H; 6.6-6.7: m, 2H; 3.8-3.9: m, 2H; 3.78: s, 3H; 2.9: m, 2H; 2.65-2.8: m, 3H; 1.5-2.05: m, 5H.

Intermediate 36

(2-Methoxy-6,7,8,9-tetrahydro-5H-benzocyclohepten-6-yl)-phenethyl-amine

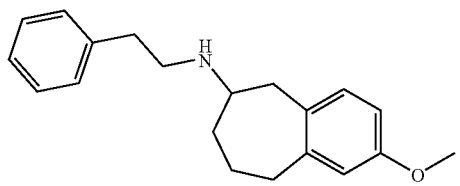

The compound is prepared analogously to Intermediate 35 using phenethylamine and was used in subsequent chemistry without further purification, 76% crude yield.

$^1$H NMR (CDCl$_3$): 7.15-7.35: m, 5H; 7.03: m, 1H; 6.03: m, 2H; 3.79: s, 3H; 2.6-3.0: m, 8H; 1.4-2.0: m, 5H.

Intermediate 37

Benzyl-(2-hydroxy-6,7,8,9-tetrahydro-5H-benzocyclohepten-6-yl)-carbamic acid tert-butyl ester

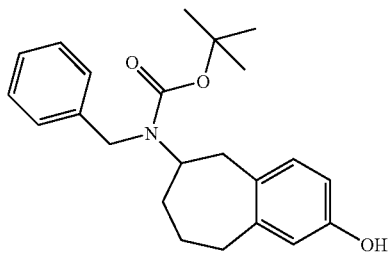

Intermediate 35 (100 mg, 0.35 mmol) is dissolved in 10 mL 48% aqueous HBr and heated under reflux for 2 hours. The reaction is then cooled to room temperature and stirred overnight, then the solvent is removed under reduced pressure. The residue is dissolved in 4 mL dioxane/1 mL 1N aqueous NaOH, and BOC anhydride (100 mg, 0.46 mmol) is added and the biphasic reaction mixture is stirred for 9 days at room temperature. And additional portion of BOC anhydride (100 mg, 0.46 mmol) is added and the reaction is stirred for 2 days at room temperature. The reaction is then poured into 25 mL saturated aqueous NH$_4$Cl, and the aqueous phase is extracted with 25 mL CH$_2$Cl$_2$. The organic layer is dried over MgSO$_4$ and evaporated, and the residue is purified by flash chromatography (20% Ethyl acetate/hexanes) to yield 30 mg of the desired material; 23% yield from Intermediate 35.

Intermediate 38

(2-Hydroxy-6,7,8,9-tetrahydro-5H-benzoeyclohepten-6-yl)-phenethyl-carbamic acid tert-butyl ester

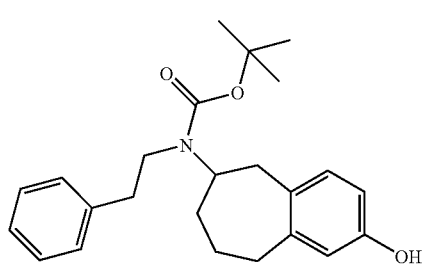

The compound is prepared analogously to Intermediate 37 starting from intermediate 36; 23% yield from Intermediate 36.

General Procedure I

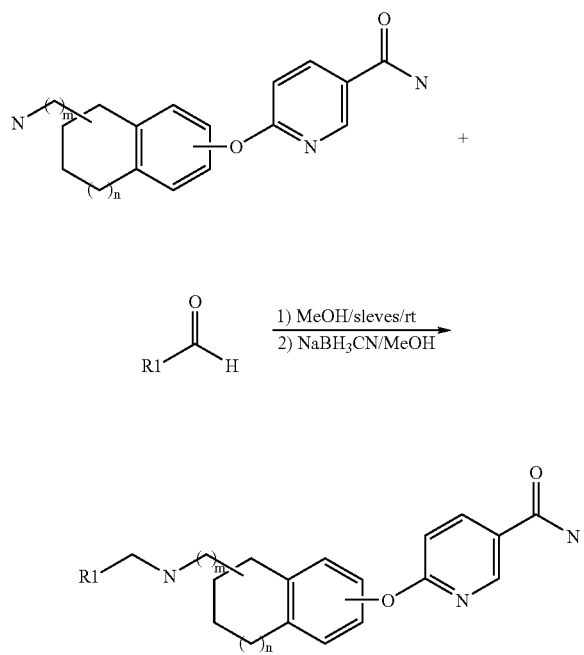

Agitate (orbital shaker) a 4 ml screw-cap vial charged with molecular sieves (ca. 200 mg), a solution of amine (0.10 M/MeOH, 100 umol, 1000 uL) and a solution of aldehyde (1.0 M/MeOH, 200 umol, 200 uL) at ambient temperature overnight. Treat mixture with a solution of NaBH$_3$CN (0.50 M/MeOH, 250 umol, 500 uL) and agitate an additional three hours. Remove the molecular sieves via filtration and concentrate the filtrate under a nitrogen stream. Redissolve the filtrate in 5% AcOH/MeOH and purify on cation exchange resin (500 mg, Varian). Further purify products on reverse-phase. HPLC (C18 column, 10% ACN/water (0.01% TFA buffer) to 95% ACN/water over 15 minutes) and free-base on cation exchange.

General Procedure II

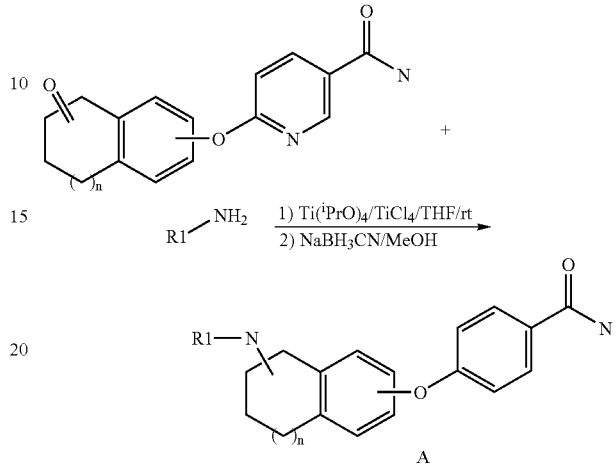

gitate (orbital shaker) a 4 ml screw-cap vial charged with amine (120 umol), a solution or suspension of ketone (0.10M/THF, 100 umol, 1000 uL), and solution of Ti($^i$PrO)$_4$ (0.40M/THF, 200 umol, 500 uL) at ambient temperature overnight. Treat the reaction with a 1.0M TiCl$_4$/DCM solution (200 umol, 200 uL) and agitate for an additional eight hours before adding NaBH$_3$CN (0.50 M/MeOH, 200 umol, 400 uL) and agitating overnight. Quench the reaction with 2N aq. NaOH (1 ml), agitate for one hour and spin down on centrifuge. Decant off supernate and concentrate supernate under nitrogen stream. Redissolve the filtrate in 5% AcOH/MeOH and purify on cation exchange resin (500 mg, Varian). Further purify products on reverse-phase HPLC (C18 column, 10% ACN/water (0.01% TFA buffer) to 95% ACN/water over 15 minutes) and free-base on cation exchange.

General Procedure III

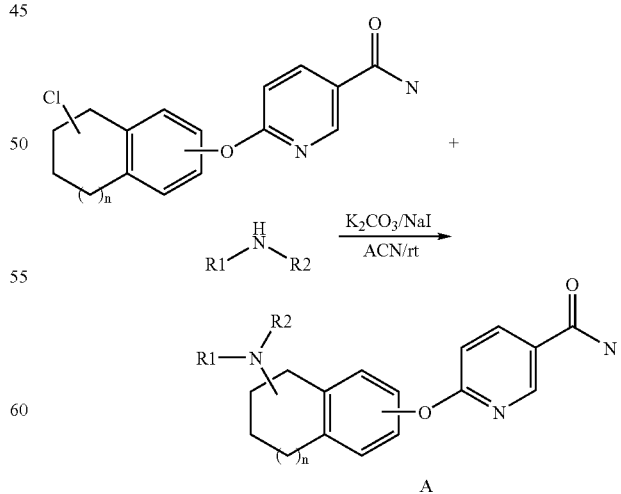

gitate (orbital shaker) a 4 ml screw-cap vial charged with amine (120 umol), K$_2$CO$_3$ (34 mg, 250 umol), NaI (3 mg, 20 umol), and a suspension of crude alkyl chloride (0.05M/ CAN, 100 umol, 2000 uL) at ambient temperature overnight. Remove the solids via filtration and concentrate the filtrate under a nitrogen stream. Redissolve the filtrate in 5% AcOH/ MeOH and purify on cation exchange resin (500 mg, Varian). Further purify products on reverse-phase HPLC (C18 column, 10% ACN/water (0.01% TFA buffer) to 95% ACN/ water over 15 minutes) and free-base on cation exchange.

General Procedure IV

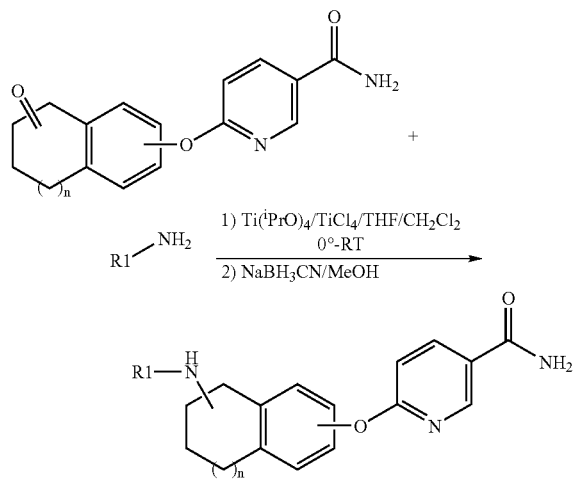

Add Ti(O$^i$Pr)$_4$ (2 equiv) to a mixture of amine (1.5 equiv), ketone (1 equiv.) in THF (0.04 M) is added at 0° C. and stir the resulting reaction mixture overnight under nitrogen atmosphere at room temperature. The following day add 1.0 M solution of TiCl$_4$ in CH$_2$Cl$_2$ (2 equiv), and after 2.5 hours add NaCNBH$_4$ (2 equiv) and stir the reaction mixture for 2 hours, then quench with saturated aqueous solution of NaHCO$_3$ diluted with ethyl acetate. Fitler off the solid and separate the organic layer, dry over anhydrous Na$_2$SO$_4$ and evaporate the solvent to yield a residue which is purified by flash chromatography using EtOAc/CH$_2$Cl$_2$/2M NH$_3$ in methanol, 0.6/ 0.35/0.05) to afford the title compound as a white solid.

EXAMPLE 1

6-[1-(3-Methyl-butylamino)-indan-5-yloxy]-nicotinamide

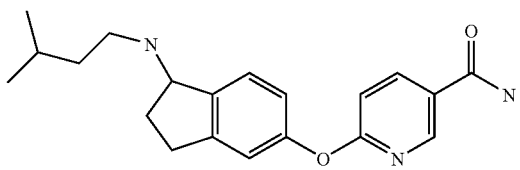

Add Ti($^i$PrO)$_4$ (1.70 g, 6.00 mmol) to a suspension-of 6-(1-oxo-indan-5-yloxy)-nicotinamide (Intermediate 4, 805 mg, 3.00 mmol), isoamyl amine (314 mg, 3.60 mmol) and THF (10 ml) and stir overnight under a nitrogen atmosphere at ambient temperature. Treat the reaction mixture with a solution of TiCl$_4$ (1.0M/DCM, 6.00 ml, 6.00 mmol) and stir at ambient temperature for three hours before adding NaBH$_3$CN (377 mg, 6.00 mmol) dissolved in MeOH (5 ml). After an additional three hours, quench the reaction with 2N aq. NaOH, making the suspension basic. Stir the suspension for one hour and filter through a filter aid to remove solids, washing them with EtOAc. Separate layers in the filtrate/ wash and wash the organic layer with brine before drying (MgSO$_4$) and concentrating. Purify on silica gel (5%(1N NH$_3$/MeOH)/45% EtOAc/DCM) to obtain 491 mg of the title compound as a light yellow solid. Mass spectrum (ion spray): m/z=340 (M+1); $^1$HNMR (CDCl$_3$): 8.59 (s, 1H), 8.16 (d, 1H), 7.39 (d, 1H), 7.00 (s, 1H), 6.97-6.94 (m, 2H), 5.87 (br. S, 2H), 4.25 (t, 1H), 3.02 (m, 1H), 2.83 (m, 1H), 2.75 (t, 2H), 2.46 (m, 1H), 1.89 (m, 1H), 1.67 (m, 1H), 1.44 (m, 2H), 0.92 (d, 6H).

EXAMPLE 2

6-[1-(2-Thiophen-2-yl-ethylamino)-indan-5-yloxy]-nicotinamide

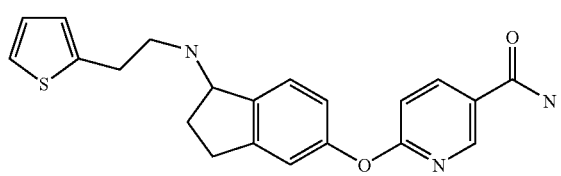

Using a method similar to Example 1, using 6-(1-oxo-indan-5-yloxy)-nicotinamide (Intermediate 4, 268 mg, 1.00 mmol), 2-thiopheneethylamine (152 mg, 1.20 mmol), Ti($^i$PrO)$_4$ (568 mg, 2.00 mmol), TiCl$_4$ (1.0M/DCM, 2.00 ml, 2.00 mmol), and NaBH$_3$CN (125 mg, 2.00 mmol) gives the title compound (196 mg) as a white solid. Mass spectrum (ion spray): m/z=380 (M+1); $^1$HNMR (CDCl$_3$): 8.58 (s, 1H), 8.15 (d, 1H), 7.35 (d, 1H), 7.16 (d, 1H). 6.99 (s, 1H), 6.96-6.93 (m, 3H), 6.86 (d, 1H), 5.81 (br. s, 2H), 4.28 (t, 1H), 3.11-2.96 (m, 5H), 2.83 (m, 1H), 2.46 (m, 1H), 1.87 (m, 1H).

EXAMPLE 3

6-{1-[2-(4-Methoxy-benzo[b]thiophen-3-yl)-ethylamino]-indan-5-yloxy}-nicotinamide

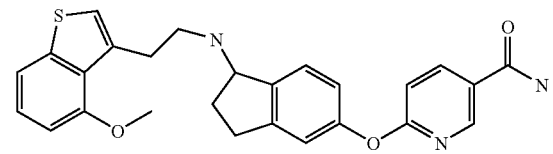

Using a method similar to Example 1, using 6-(1-oxo-indan-5-yloxy)-nicotinamide (Intermediate 4, 97 mg, 0.362 mmol), 2-(4-methoxy-benzo[b]thiophen-3-yl)-ethylamine HCl salt (J. Heterocycl. Chem. (1973), 10(3), 297-305, 93 mg, 0.435 mmol), Et$_3$N (44 mg, 0.435 mmol), Ti($^i$PrO)$_4$ (206 mg, 0.725 mmol), TiCl$_4$ (1.0M/DCM, 0.725 ml, 0.725 mmol), and NaBH$_3$CN (45 mg, 0.725 mmol) gives the title compound (83 mg) as a light yellow solid. Mass spectrum (ion spray): m/z=460 (M+1); $^1$HNMR (CDCl$_3$): 8.58 (s, 1H), 8.15 (d, 1H), 7.42 (d, 1H), 7.33 (d, 1H), 7.25 (t, 1H), 7.02 (s, 1H), 6.98 (s, 1H), 6.94-6.91 (m, 2H), 6.75 (d, 1H), 5.82 (br. s, 2H), 4.30 (t, 1H), 3.91 (s, 3H), 3.29 (t, 2H), 3.09 (m, 2H), 3.01 (m, 1H), 2.83 (m, 1H), 2.45 (m, 1H), 1.90 (m, 1H).

EXAMPLE 4

6-[5-(2-Thiophen-2-yl-ethylamino)-5,6,7,8-tetrahydro-naphthalen-2-yloxy]-nicotinamide

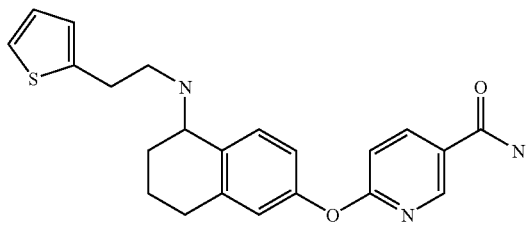

Using a method similar to Example 1, using 6-(5-oxo-5,6,7,8-tetrahydro-naphthalen-2-yloxy)-nicotinamide (Intermediate 2, 546 mg, 2.00 mmol), 2-thiopheneethylamine (305 mg, 2.40 mmol), Ti($^i$PrO)$_4$ (1.14 g, 4.00 mmol), TiCl$_4$ (1.0M/DCM, 4.00 ml, 4.00 mmol), and NaBH$_3$CN (251 mg, 4.00 mmol) gives the title compound (491.mg) as a light yellow solid. Mass spectrum (ion spray): m/z=394 (M+1); $^1$HNMR (CDCl$_3$): 8.58 (s, 1H), 8.15 (d, 1H), 7.36 (d, 1H), 7.15 (d, 1H), 6.95-6.89 (m, 3H), 6.85 (m, 2H), 5.87 (br. s, 2H), 3.81 (t, 1H), 3.12-3.02 (m, 3H), 2.98 (m, 1H), 2.83-2.68 (m, 2H), 1.98-1.82 (m, 3H), 1.73 (m, 1H).

EXAMPLE 5

6-{1-[2-(3-Chloro-phenyl)-ethylamino]-indan-5-yloxy}-nicotinamide

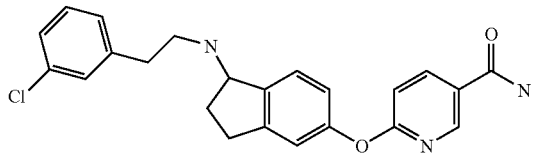

Using a method similar to Example 1, using 6-(1-oxo-indan-5-yloxy)-nicotinamide (Intermediate 4, 805 mg, 3.00 mmol), 2-(3-chlorophenyl)ethylamine (560 mg, 3.60 mmol), Ti($^i$PrO)$_4$ (1.70 g, 6.00 mmol), TiCl$_4$ (1.0M/DCM, 6.00 ml, 6.00 mmol), and NaBH$_3$CN (377 mg, 6.00 mmol) gives the title compound (738 mg) as a white solid.

Mass spectrum (ion-spray): m/z=408 (M+1); $^1$HNMR (CDCl$_3$): 8.58 (s, 1H), 8.15 (d, 1H), 7.31 (d, 1H), 7.25-7.18 (m, 3H), 7.11 (d, 1H), 6.98-6.93 (m, 3H), 5.89 (br. s, 2H), 4.26 (t, 1H), 3.03-2.96 (m, 3H), 2.87-2.78 (m, 3H), 2.44 (m, 1H), 1.85 (m, 1H).

EXAMPLE 6

6-{5-[2-(3-Chloro-phenyl)-ethylamino]-5,6,7,8-tetrahydro-naphthalen-2-yloxy}-nicotinamide

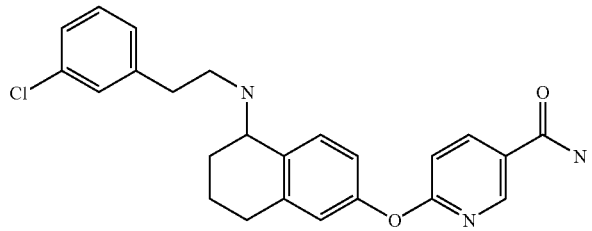

Using a method similar to Example 1, using 6-(5-oxo-5,6,7,8-tetrahydro-naphthalen-2-yloxy)-nicotinamide (Intermediate 2, 846 mg, 3.00 mmol), 2-(3-chlorophenyl)ethylamine (560 mg, 3.60 mmol), Ti($^i$PrO)$_4$ (1.70 g, 6.00 mmol), TiCl$_4$ (1.0M/DCM, 6.00 ml, 6.00 mmol), and NaBH$_3$CN (377 mg, 6.00 mmol) gives the title compound (1.16 g) as a white solid. Mass spectrum (ion spray): m/z=422 (M+1); $^1$HNMR (CDCl$_3$): 8.58 (s, 1H), 8.15 (d, 1H), 7.33 (d, 1H), 7.24-7.17 (m, 3H), 7.11 (d, 1H), 6.94 (d, 1H), 6.90 (d, 1H), 6.85 (s, 1H), 5.87 (br. s, 2H), 3.79 (t, 1H), 3.06-2.91 (m, 2H), 2.83-2.67 (m, 4H), 1.97-1.79 (m, 3H), 1.73 (m, 1H).

EXAMPLE 7

6-{1-[2-(2-Fluoro-phenyl)-ethylamino]-indan-5-yloxy}-nicotinamide

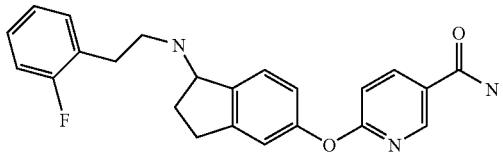

Using a method similar to Example 1, using 6-(1-oxo-indan-5-yloxy)-nicotinamide (Intermediate 4, 805 mg, 3.00 mmol), 2-(2-fluorophenyl)ethylamine (501 mg, 3.60 mmol), Ti($^i$PrO)$_4$ (1.70 g, 6.00 mmol), TiCl$_4$ (1.0M/DCM, 6.00 ml, 6.00 mmol), and NaBH$_3$CN (377 mg, 6.00 mmol) gives the title compound (398 mg) as a white solid.

Mass spectrum (ion spray): m/z=392 (M+1); $^1$HNMR (CDCl$_3$): 8.58 (s, 1H), 8.15 (d, 1H), 7.32 (d, 1H), 7.25-7.17 (m, 2H), 7.09-7.00 (m, 2H), 6.98 (s, 1H), 6.94 (d, 2H), 5.93 (br. s, 2H), 4.28 (t, 1H), 3.04-2.95 (m, 3H), 2.92-2.87 (m, 2H), 2.83 (m, 1H), 2.45 (m, 1H), 1.85 (m, 1H).

EXAMPLE 8

6-{5-[2-(2-Fluoro-phenyl)-ethylamino]-5,6,7,8-tetrahydro-naphthalen-2-yloxy}-nicotinamide

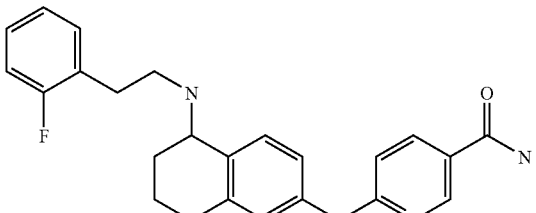

Using a method similar to Example 1, using 6-(5-oxo-5,6,7,8-tetrahydro-naphthalen-2-yloxy)-nicotinamide (Intermediate 2, 846 mg, 3.00 mmol), 2-(2-fluorophenyl)ethylamine (501 mg, 3.60 mmol), Ti($^i$PrO)$_4$ (1.70 g, 6.00 mmol), TiCl$_4$ (1.0M/DCM, 6.00 ml, 6.00 mmol), and NaBH$_3$CN (377 mg, 6.00 mmol) gives the title compound (1.01 g) as a white solid.
Mass spectrum (ion spray): m/z=406 (M+1); $^1$HNMR (CDCl$_3$): 8.59 (s, 1H), 8.15 (d, 1H), 7.35 (d, 1H), 7.26-7.16 (m, 2H), 7.09-6.99 (m, 2H), 6.93 (d, 1H), 6.89 (d, 1H), 6.84 (s, 1H), 5.89 (br. s, 2H), 3.81 (t, 1H), 3.07-2.85 (m, 4H), 2.83-2.67 (m, 2H), 1.98-1.80 (m, 3H), 1.73 (m, 1H).

EXAMPLE 9

6-[1-(2,2-Diphenyl-ethylamino)-indan-5-yloxy]-nicotinamide

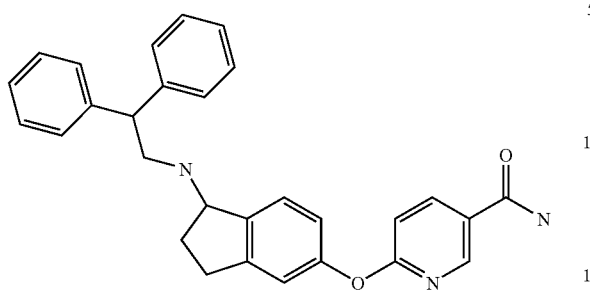

Using a method similar to Example 1, using 6-(1-oxo-indan-5-yloxy)-nicotinamide (Intermediate 4, 536 mg, 2.00 mmol), 2,2-diphenylethylamine (473 mg, 2.40 mmol), Ti($i$PrO)$_4$ (1.14 g, 4.00 mmol), TiCl$_4$ (1.0 M/DCM, 4.00 ml, 4.00 mmol), and NaBH$_3$CN (251 mg, 4.00 mmol) gives the title compound (608 mg) as a white solid. Mass spectrum (ion spray): m/z=450 (M+1); $^1$HNMR (CDCl$_3$): 8.57 (s, 1H), 8.14 (d, 1H), 7.33-7.18 (m, 11H), 6.98-6.90 (m, 3H), 5.85 (br. s, 2H), 4.33-4.23 (m, 2H), 3.41-3.31 (m, 2H), 2.95 (m, 1H), 2.81 (m, 1H), 2.46 (m, 1H), 1.85 (m, 1H).

EXAMPLE 10

6-[5-3-Phenyl-propylamino)-5,6,7,8-tetrahydro-naphthalen-2-yloxy]-nicotinamide

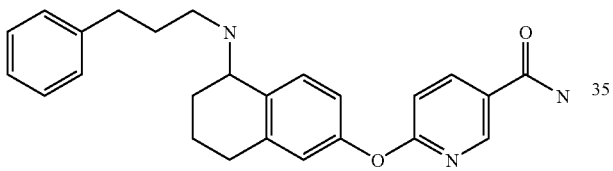

Using a method similar to Example 1, using 6-(5-oxo-5,6,7,8-tetrahydro-naphthalen-2-yloxy)-nicotinamide (Intermediate 2, 564 mg, 2.00 mmol), 3-phenylpropylamine (324 mg, 2.40 mmol), Ti($i$PrO)$_4$ (1.14 g, 4.00 mmol), TiCl$_4$ (1.0M/DCM, 4.00 ml, 4.00 mmol), and NaBH$_3$CN (251 mg, 4.00 mmol) gives the title compound (558 mg) as a light yellow solid. Mass spectrum (ion spray): m/z=402 (M+1); $^1$HNMR (CDCl$_3$): 8.59 (s, 1H), 8.14 (d, 1H), 7.40 (d, 1H), 7.30-7.25 (m, 2H), 7.21-7.16 (m, 3H), 6.93 (d, 1H), 6.91 (d, 1H), 6.85 (s, 1H), 5.99 (br. s, 2H), 3.74 (t, 1H), 2.84-2.64 (m, 6H), 2.00-1.79.(m, 5H), 1.72 (m, 1H).

EXAMPLE 11

6-[1-(3-Phenyl-propylamino)-indan-5-yloxy]-nicotinamide

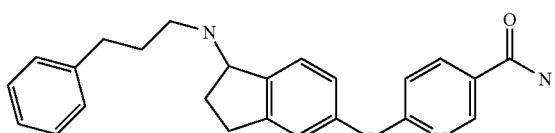

Using a method similar to Example 1, using 6-(1-oxo-indan-5-yloxy)-nicotinamide (Intermediate 4, 805 mg, 3.00 mmol), 3-phenylpropylamine (486 mg, 3.60 mmol), Ti($i$PrO)$_4$ (1.70 g, 6.00 mmol), TiCl$_4$ (1.0M/DCM, 6.00 ml, 6.00 mmol), and NaBH$_3$CN (377 mg, 6.00 mmol) gives the title compound (681 mg) as a light yellow solid. Mass spectrum (ion spray): m/z=388 (M+1); $^1$HNMR (CDCl$_3$): 8.59 (s, 1H), 8.15 (d, 1H), 7.35 (d, 1H), 7.30-7.25 (m, 2H), 7.22-7.16 (m, 3H), 6.99 (s, 1H), 6.95 (d, 1H), 5.85 (br. s, 2H), 4.23 (t, 1H), 3.00 (m, 1H), 2.83 (m, 1H), 2.78 (t, 2H), 2.70 (m, 2H), 2.43 (m, 1H), 1.87 (m, 3H).

EXAMPLE 12

6-(1-Hexylamino-indan-5-yloxy)-nicotinamide

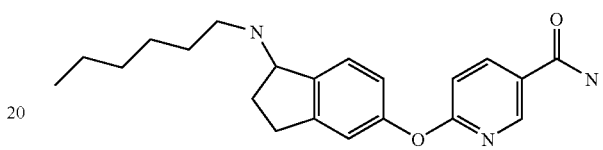

Using a method similar to Example 1, using 6-(1-oxo-indan-5-yloxy)-nicotinamide (Intermediate 4, 1.11 g, 4.14 mmol), n-hexylamine (502 mg, 4.96 mmol), Ti($i$PrO)$_4$ (2.35 g, 8.27 mmol), TiCl$_4$ (1.0M/DCM, 8.27 ml, 8.27 mmol), and NaBH$_3$CN (520 mg, 8.27 mmol) gives the title compound (495 mg) as a tan solid. Mass spectrum (ion spray): m/z=354 (M+1); $^1$HNMR (CDCl$_3$): 8.59 (s, 1H), 8.16 (d, 1H), 7.38 (d, 1H), 6.99 (s, 1H), 6.96 (d, 1H), 6.94 (d, 1H), 5.92 (br. s, 2H), 4.24 (t, 1H), 3.01 (m, 1H), 2.83 (m, 1H), 2.73 (t, 2H), 2.45 (m, 1H), 1.88 (m, 1H), 1.53 (m, 3H), 1.32 (m, 5H), 0.89 (t, 3H).

EXAMPLE 13

6-{1-[(2,2-Diphenyl-ethyl)-methyl-amino]-indan-5-yloxy}-nicotinamide

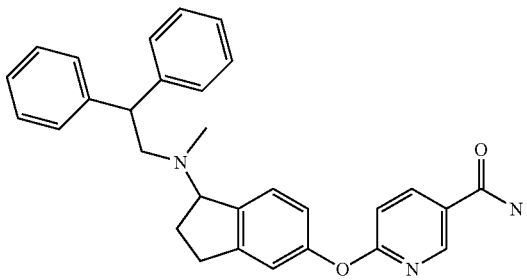

Add paraformaldehyde (57 mg) and NaBH$_3$CN (46 mg, 0.734 mmol) to a solution of 6-[1-(2,2-Diphenyl-ethylamino)-indan-5-yloxy)-nicotinamide (example 9, 110 mg, 0.245 mmol) in 5% AcOH/MeOH (3 ml) and stir at ambient temperature for two days. Concentrate the reaction mixture and partition remaining residue between EtOAc and 1M aq. K$_2$CO$_3$. Separate layers and wash organic with 1M aq. K$_2$CO$_3$ and brine before drying (MgSO$_4$) and concentrating. Purify on silica gel (5% (1N NH$_3$/MeOH)/45% EtOAc/DCM) to obtain 74 mg of the title compound as a white solid. Mass spectrum (ion spray): m/z=464 (M+1); $^1$HNMR (CDCl$_3$): 8.54 (s, 1H), 8.15 (d, 1H), 7.30-7.15 (m, 10H), 6.95-6.81 (m, 4H), 5.81 (br. s, 2H), 4.39 (t, 1H), 4.20 (t, 1H), 3.02 (d, 2H), 2.94-2.75 (m, 2H), 2.27 (s, 3H), 2.06 (m, 2H).

EXAMPLE 14

6-[1-(2-m-Tolyl-ethylamino)-indan-5-yloxy]-nicotinamide

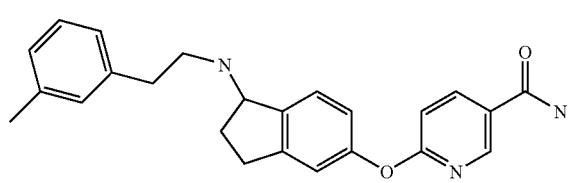

Add Ti($^i$Pro)$_4$ (1.70 g, 6.00 mmol) to a suspension of 6-(1-oxo-indan-5-yloxy)-nicotinamide (Intermediate 4,805 mg, 3.00 mmol), 2-(3-methylphenyl)ethylamine (446 mg, 3.30 mmol) and THF (20 ml) and stir for six hours under a nitrogen atmosphere at ambient temperature. After cooling in an ice/water bath, treat the reaction mixture with a solution of TiCl$_4$ (1.0M/DCM, 6.00 ml, 6.00 mmol) and stir at 0-5° C. for two hours before adding NaBH$_3$CN (377 mg, 6.00 mmol) dissolved in MeOH (5 ml). Allow the reaction mixture to warm to ambient temperature as the cold bath warms and stir overnight. Quench the reaction with 2N aq. NaOH, making the suspension basic. Stir the suspension for one hour and filter through a filter aid to remove solids, washing them with EtOAc. Separate layers in the filtrate/wash and wash the organic layer with brine before drying (MgSO$_4$) and concentrating. Purify on silica gel (5% (1N NH$_3$/MeOH)/45% EtOAc/DCM) to obtain 849 mg of the title compound as a light yellow solid. Mass spectrum (ion spray): m/z=388 (M+1); $^1$HNMR (CDCl$_3$): 8.59 (s, 1H), 8.15 (d, 1H), 7.30 (d, 1H), 7.19 (t, 1H), 7.05-7.01 (m, 3H), 6.98 (s, 1H), 6.93 (d, 2H), 5.96 (br. s, 2H), 4.26 (t, 1H), 3.02-2.94 (m, 3H), 2.86-2.76 (m, 3H), 2.44 (m, 1H), 2.33 (s, 3H), 1.84 (m, 1H).

EXAMPLE 15

6-[1-(Hexyl-methyl-amino)-indan-5-yloxy]-nicotinamide. 2103035. AG2-A02084-114.

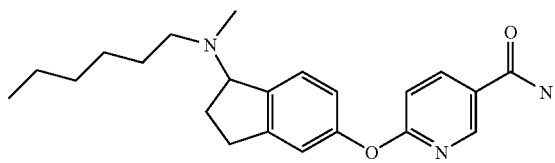

Using a method similar to Example 13, using 6-(1-hexylamino-indan-5-yloxy)-nicotinamide (example 12, 490 mg, 1.38 mmol), paraformaldehyde (443 mg), and NaBH$_3$CN (261 mg, 4.16 mmol) gives the title compound (373 mg) as a light yellow solid. Mass spectrum (ion spray): m/z=368 (M+1); $^1$HNMR (CDCl$_3$): 8.59 (s, 1H), 8.16 (d, 1H), 7.38 (d, 1H), 6.98-6.93 (m, 3H), 5.89 (br. s, 2H), 4.42 (t, 1H), 2.97-2.78 (m, 2H), 2.40 (m, 2H), 2.22 (s, 3H), 2.08 (m, 2H), 1.51 (m, 2H), 1.36-1.22 (m, 6H), 0.88 (t, 3H).

EXAMPLE 16

6-[1-(2-Cyclohexyl-ethylamino)-indan-5-yloxy]-nicotinamide

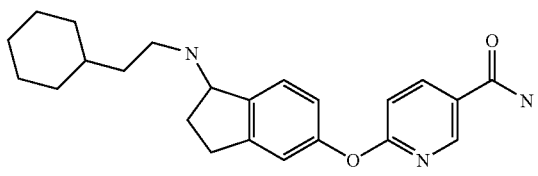

Using a method similar to Example 14, using 6-(1-oxo-indan-5-yloxy)-nicotinamide (Intermediate 4, 536 mg, 2.00 mmol), 2-cyclohexylethylamine HCl ((Synthesis (1983), (5), 388-9), 393 mg, 2.40 mmol), Et$_3$N (243 mg, 2.40 mmol), Ti($^i$PrO)$_4$ (1.14 g, 4.00 mmol), TiCl$_4$ (1.0M/DCM, 4.00 ml, 4.00 mmol), and NaBH$_3$CN (251 mg, 4.00 mmol) gives the title compound (628 mg) as a yellow solid. Mass spectrum (ion spray): m/z=380 (M+1); $^1$HNMR (CDCl$_3$): 8.59 (s, 1H), 8.15 (d, 1H), 7.38 (d, 1H), 6.99 (s, 1H), 6.95 (d, 1H), 6.94 (d, 1H), 5.89 (br. s, 2H), 4.24 (t, 1H), 3.01 (m, 1H), 2.82 (m, 1H), 2.75 (t, 2H), 2.45 (m, 1H), 1.88 (m, 1H), 1.74-1.62 (m, 5H), 1.43 (m, 2H), 1.38-1.13 (m, 4H), 0.93 (m, 2H).

EXAMPLE 17

6-(3,3-Dimethyl-1-phenethylamino-indan-5-yloxy)-nicotinamide

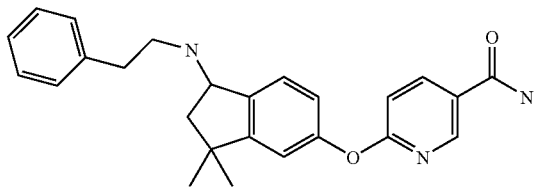

Using a method similar to Example 14, using 6-(3,3-dimethyl-1-oxo-indan-5-yloxy)-nicotinamide (Intermediate 11, 100 mg, 0.337 mmol), phenethylamine (49 mg, 0.405 mmol), Ti($^i$PrO)$_4$ (192 mg, 0.675 mmol), TiCl$_4$ (1.0M/DCM, 0.675 ml, 0.675 mmol), and NaBH$_3$CN (42 mg, 0.675 mmol) gives the title compound (90 mg) as a white solid. Mass spectrum (ion spray): m/z=402 (M+1); $^1$HNMR (CDCl$_3$): 8.60 (s, 1H), 8.14 (d, 1H), 7.32-7.19 (m, 6H), 6.95-6.88 (m, 3H), 6.25 (br. s, 2H), 4.31 (t, 1H), 3.02 (m, 2H), 2.86 (m, 2H), 2.33 (m, 1H), 1.68 (m, 1H), 1.31 (s, 3H), 1.17 (s, 3H).

EXAMPLE 18

6-(1-Phenethylamino-indan-5-yloxy)-nicotinamide

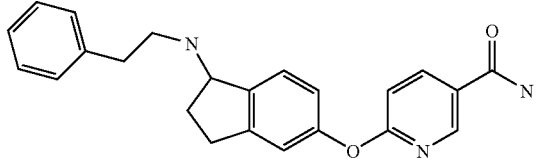

Using a method similar to Example 14, using 6-(1-oxo-indan-5-yloxy)-nicotinamide (Intermediate 4, 805 mg, 3.00 mmol), phenethylamine (436 mg, 3.60 mmol), Ti($^i$PrO)$_4$ (1.70 g, 6.00 mmol), TiCl$_4$ (1.0M/DCM, 6.00 ml, 6.00 mmol), and NaBH$_3$CN (377 mg, 6.00 mmol) gives the title compound (984 mg) as a light yellow solid. Mass spectrum (ion spray): m/z=374 (M+1); $^1$HNMR (CDCl$_3$): 8.59 (s, 1H), 8.15 (d, 1H), 7.33-7.19 (m, 6H), 6.98 (s, 1H), 6.95-6.91 (m, 2H), 5.99 (br. s, 2H), 4.26 (t, 1H), 3.04-2.94 (m, 3H), 2.88-2.74 (m, 3H), 2.44 (m, 1H), 1.84 (m, 1H).

EXAMPLE 19

6-(4-Methyl-1-phenethylamino-indan-5-yloxy)-nicotinamide

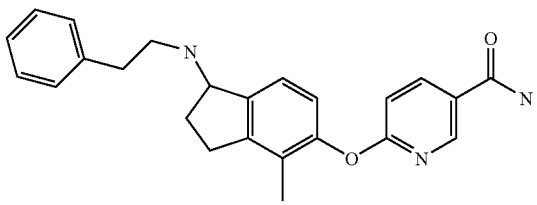

Using a method similar to Example 14, using 6-(4-methyl-1-oxo-indan-5-yloxy)-nicotinamide (Intermediate 12, 100 mg, 0.354 mmol), phenethylamine (52 mg, 0.425 mmol), Ti(iPrO)$_4$ (201 mg, 0.708 mmol), TiCl$_4$ (1.0M/DCM, 0.708 ml, 0.708 mmol), and NaBH$_3$CN (44 mg, 0.708 mmol) gives the title compound (112 mg) as a white solid. Mass spectrum (ion spray): m/z=388 (M+1); $^1$HNMR (CDCl$_3$): 8.57 (s, 1H), 8.14 (d, 1H), 7.32-7.19 (m, 5H), 7.14 (d, 1H), 6.91-6.87 (m, 2H), 6.03 (br. s, 2H), 4.28 (t, 1H), 3.01 (t, 2H), 2.94 (m, 1H), 2.85 (m, 2H), 2.74 (m, 1H), 2.44 (m, 1H), 2.02 (s, 3H), 1.86 (m, 1H).

EXAMPLE 20

6-{1-[Methyl-(3-methyl-butyl)-amino]-indan-5-yloxy)-nicotinamide

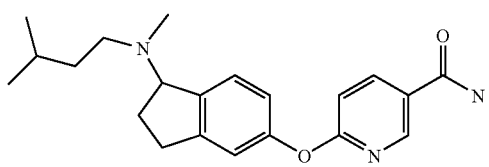

Heat a suspension of 6-(1-oxo-indan-5-yloxy)-nicotinamide (Intermediate 4, 268 mg, 1.00 mmol), methyl isoamylamine (121 mg, 1.20 mmol), Ti(iPrO)$_4$ (426 mg, 1.50 mmol), and THF (0.5 ml) at 50° C. overnight. Dilute the mixture with MeOH (5 ml), add NaBH$_3$CN (94 mg, 1.50 mmol), and stir at ambient temperature for 16 hours. Quench reaction with 2N aq. NaOH (10 ml) and stir for ca. one hour. Remove solids via filtration and wash filtercake with EtOAc. Separate layers in the filtrate/wash and wash organic layer with brine before drying (MgSO$_4$) and concentrating. Redissolve the filtrate in 5% AcOH/MeOH and purify on cation exchange resin (2 g, Varian). Further purify product on reverse-phase HPLC (C18 column, 10% ACN/water (0.01% TFA buffer) to 95% ACN/water over 15 minutes) and free-base with 1M aq. K$_2$CO$_3$/EtOAc to give the title compound (151 mg) as a white solid. Mass spectrum (ion spray): m/z=354 (M+1); $^1$HNMR (CDCl$_3$): 8.60 (s, 1H), 8.15 (d, 1H), 7.37 (d, 1H), 6.98-6.92 (m, 3H), 6.09 (br. s, 2H), 4.42 (t, 1H), 2.87 (m, 2H), 2.43 (m, 2H), 2.20 (s, 3H), 2.08 (m, 2H), 1.61 (m, 1H), 1.41 (m 2H), 0.88 (d, 6H).

EXAMPLE 21

6-[1-(Methyl-phenethyl-amino)-indan-5-yloxy]-nicotinamide

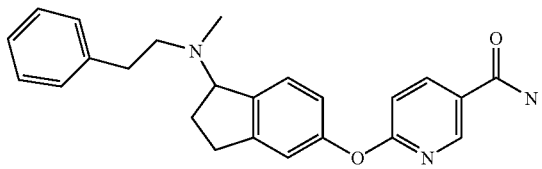

Using a method similar to Example 13, using 6-(1-phenethylamino-indan-5-yloxy)-nicotinamide (example 18, 980 mg, 2.62 mmol), paraformaldehyde (1.03 g), and NaBH$_3$CN (494 mg, 7.87 mmol) gives the title compound (930 mg) as a light yellow solid. Mass spectrum (ion spray): m/z=388 (M+1); $^1$HNMR (CDCl$_3$): 8.59 (s, 1H), 8.16 (d, 1H), 7.30-7.17 (m, 6H), 6.97-6.91 (m, 3H), 5.79 (br. s, 2H), 4.45 (t, 1H), 2.96-2.74 (m, 4H), 2.68 (m, 2H), 2.33 (s, 3H), 2.09 (m, 2H).

EXAMPLES 22-200

| Example | IUPAC name | General Procedure | Intermed. # | Reagent | Mass (pos. ion) |
|---|---|---|---|---|---|
| 22 | 6-(8-Pentylamino-5,6,7,8-tetrahydro-naphthalen-2-yloxy)-nicotinamide | II | 1 | n-pentylamine | 354 |
| 23 | 6-(5-Pentylamino-5,6,7,8-tetrahydro-naphthalen-2-yloxy)-nicotinamide | II | 2 | n-pentylamine | 354 |
| 24 | 6-(5-Pentylamino-5,6,7,8-tetrahydro-naphthalen-1-yloxy)-nicotinamide | II | 3 | n-pentylamine | 354 |
| 25 | 6-(1-Pentylamino-indan-5-yloxy)-nicotinamide | II | 4 | n-pentylamine | 340 |
| 26 | 6-(1-Pentylamino-indan-4-yloxy)-nicotinamide | II | 5 | n-pentylamine | 340 |

| Example | IUPAC name | General Procedure | Intermed. # | Reagent | Mass (pos. ion) |
|---|---|---|---|---|---|
| 27 | 6-(8-Benzylamino-5,6,7,8-tetrahydro-naphthalen-2-yloxy)-nicotinamide | II | 1 | benzylamine | 374 |
| 28 | 6-(5-Benzylamino-5,6,7,8-tetrahydro-naphthalen-2-Yloxy)-nicotinamide | II | 2 | benzylamine | 374 |
| 29 | 6-(5-Benzylamino-5,6,7,8-tetrahydro-naphthalen-1-yloxy)-nicotinamide | II | 3 | benzylamine | 374 |
| 30 | 6-(1-Benzylamino-indan-4-yloxy)-nicotinamide | II | 5 | benzylamine | 360 |
| 31 | 6-(8-Phenethylamino-5,6,7,8-tetrahydro-naphthalen-2-yloxy)-nicotinamide | II | 1 | phenethylamine | 388 |
| 32 | 6-(5-Phenethylamino-5,6,7,8-tetrahydro-naphthalen-2-yloxy)-nicotinamide | II | 2 | phenethylamine | 388 |
| 33 | 6-(5-Phenethylamino-5,6,7,8-tetrahydro-naphthalen-1-yloxy)-nicotinamide | II | 3 | phenethylamine | 388 |
| 34 | 6-(1-Phenethylamino-indan-4-yloxy)-nicotinamide | II | 5 | phenethylamine | 374 |
| 35 | 6-{8-[2-(3-Fluoro-phenyl)-ethylamino]-5,6,7,8-tetrahydro-naphthalen-2-yloxy}-nicotinamide | II | 1 | 3-fluorophenethylamine | 406 |
| 36 | 6-{5-[2-(3-Fluoro-phenyl)-ethylamino]-5,6,7,8-tetrahydro-naphthalen-2-yloxy}-nicotinamide | II | 2 | 3-fluorophenethylamine | 406 |
| 37 | 6-{5-[2-(3-Fluoro-phenyl)-ethylamino]-5,6,7,8-tetrahydro-naphthalen-1-yloxy}-nicotinamide | II | 3 | 3-fluorophenethylamine | 406 |
| 38 | 6-{3-[2-(3-Fluoro-phenyl)-ethylamino]-indan-5-yloxy}-nicotinamide | II | 6 | 3-fluorophenethylamine | 392 |
| 39 | 6-{1-[2-(3-Fluoro-phenyl)-ethylamino]-indan-5-yloxy}-nicotinamide | II | 4 | 3-fluorophenethylamine | 392 |
| 40 | 6-{1-[2-(3-Fluoro-phenyl)-ethylamino]-indan-4-yloxy}-nicotinamide | II | 5 | 3-fluorophenethylamine | 392 |
| 41 | 6-[8-(3-Methyl-butylamino)-5,6,7,8-tetrahydro-naphthalen-2-yloxy]-nicotinamide | II | 1 | isoamylamine | 354 |
| 42 | 6-[5-(3-Methyl-butylamino)-5,6,7,8-tetrahydro-naphthalen-2-yloxy]-nicotinamide | II | 2 | isoamylamine | 354 |
| 43 | 6-[5-(3-Methyl-butylamino)-5,6,7,8-tetrahydro-naphthalen-1-yloxy]-nicotinamide | II | 3 | isoamylamine | 354 |
| 44 | 6-[8-(4-Methyl-cyclohexylamino)-5,6,7,8-tetrahydro-naphthalen-2-yloxy]-nicotinamide | II | 1 | 4-methylcyclohexylamine, cis/trans mixture | 380 |
| 45 | 6-[5-(4-Methyl-cyclohexylamino)-5,6,7,8-tetrahydro-naphthalen-2-yloxy]-nicotinamide | II | 2 | 4-methylcyclohexylamine, cis/trans mixture | 380 |
| 46 | 6-[5-(4-Methyl-cyclohexylamino)-5,6,7,8-tetrahydro-naphthalen-1-yloxy]-nicotinamide | II | 3 | 4-methylcyclohexylamine, cis/trans mixture | 380 |
| 47 | 6-[1-(4-Methyl-cyclohexylamino)-indan-5-yloxy]-nicotinamide | II | 4 | 4-methylcyclohexylamine, cis/trans mixture | 366 |
| 48 | 6-[1-(4-Methyl-cyclohexylamino)-indan-4-yloxy]-nicotinamide | II | 5 | 4-methylcyclohexylamine, cis/trans mixture | 366 |
| 49 | 6-(7-Pentylamino-5,6,7,8-tetrahydro-naphthalen-2-yloxy)-nicotinamide | II | 7 | n-pentylamine | 354 |

-continued

| Example | IUPAC name | General Procedure | Intermed. # | Reagent | Mass (pos. ion) |
|---|---|---|---|---|---|
| 50 | 6-(6-Pentylamino-5,6,7,8-tetrahydro-naphthalen-2-yloxy)-nicotinamide | II | 8 | n-pentylamine | 354 |
| 51 | 6-(6-Pentylamino-5,6,7,8-tetrahydro-naphthalen-1-yloxy)-nicotinamide | II | 9 | n-pentylamine | 354 |
| 52 | 6-(7-Pentylamino-5,6,7,8-tetrahydro-naphthalen-1-yloxy)-nicotinamide | II | 10 | n-pentylamine | 354 |
| 53 | 6-(7-Benzylamino-5,6,7,8-tetrahydro-naphthalen-2-yloxy)-nicotinamide | II | 7 | benzylamine | 374 |
| 54 | 6-(6-Benzylamino-5,6,7,8-tetrahydro-naphthalen-2-yloxy)-nicotinamide | II | 8 | benzylamine | 374 |
| 55 | 6-(6-Benzylamino-5,6,7,8-tetrahydro-naphthalen-1-yloxy)-nicotinamide | II | 9 | benzylamine | 374 |
| 56 | 6-(7-Benzylamino-5,6,7,8-tetrahydro-naphthalen-1-yloxy)-nicotinamide | II | 10 | benzylamine | 374 |
| 57 | 6-(7-Phenethylamino-5,6,7,8-tetrahydro-naphthalen-2-yloxy)-nicotinamide | II | 7 | phenethylamine | 387 |
| 58 | 6-(6-Phenethylamino-5,6,7,8-tetrahydro-naphthalen-2-yloxy)-nicotinamide | II | 8 | phenethylamine | 387 |
| 59 | 6-(6-Phenethylamino-5,6,7,8-tetrahydro-naphthalen-1-yloxy)-nicotinamide | II | 9 | phenethylamine | 387 |
| 60 | 6-(7-Phenethylamino-5,6,7,8-tetrahydro-naphthalen-1-yloxy)-nicotinamide | II | 10 | phenethylamine | 387 |
| 61 | 6-{7-[2-(3-Fluoro-phenyl)-ethylamino]-5,6,7,8-tetrahydro-naphthalen-2-yloxy}-nicotinamide | II | 7 | 3-fluorophenethylamine | 406 |
| 62 | 6-{6-[2-(3-Fluoro-phenyl)-ethylamino]-5,6,7,8-tetrahydro-naphthalen-2-yloxy}-nicotinamide | II | 8 | 3-fluorophenethylamine | 406 |
| 63 | 6-{6-[2-(3-Fluoro-phenyl)-ethylamino]-5,6,7,8-tetrahydro-naphthalen-1-yloxy}-nicotinamide | II | 9 | 3-fluorophenethylamine | 406 |
| 64 | 6-{7-[2-(3-Fluoro-phenyl)-ethylamino]-5,6,7,8-tetrahydro-naphthalen-1-yloxy}-nicotinamide | II | 10 | 3-fluorophenethylamine | 406 |
| 65 | 6-[7-(3-Methyl-butylamino)-5,6,7,8-tetrahydro-naphthalen-2-yloxy]-nicotinamide | II | 7 | isoamylamine | 354 |
| 66 | 6-[6-(3-Methyl-butylamino)-5,6,7,8-tetrahydro-naphthalen-2-yloxy]-nicotinamide | II | 8 | isoamylamine | 354 |
| 67 | 6-[6-(3-Methyl-butylamino)-5,6,7,8-tetrahydro-naphthalen-1-yloxy]-nicotinamide | II | 9 | isoamylamine | 354 |
| 68 | 6-[7-(3-Methyl-butylamino)-5,6,7,8-tetrahydro-naphthalen-1-yloxy]-nicotinamide | II | 10 | isoamylamine | 354 |
| 69 | 6-[7-(4-Methyl-cyclohexylamino)-5,6,7,8-tetrahydro-naphthalen-2-yloxy]-nicotinamide | II | 7 | 4-methylcyclohexylamine, cis/trans mixture | 380 |
| 70 | 6-[6-(4-Methyl-cyclohexylamino)-5,6,7,8-tetrahydro-naphthalen-1-yloxy]-nicotinamide | II | 9 | 4-methylcyclohexylamine, cis/trans mixture | 380 |
| 71 | 6-[7-(4-Methyl-cyclohexylamino)-5,6,7,8- | II | 10 | 4-methylcyclohexylamine, | 380 |

-continued

| Example | IUPAC name | General Procedure | Intermed. # | Reagent | Mass (pos. ion) |
|---|---|---|---|---|---|
| | tetrahydro-naphthalen-1-yloxy]-nicotinamide | | | cis/trans mixture | |
| 72 | 6-[7-(3-Phenyl-propylamino)-5,6,7,8-tetrahydro-naphthalen-2-yloxy]-nicotinamide | II | 7 | 3-phenylpropylamine | 402 |
| 73 | 6-[6-(3-Phenyl-propylamino)-5,6,7,8-tetrahydro-naphthalen-2-yloxy]-nicotinamide | II | 8 | 3-phenylpropylamine | 402 |
| 74 | 6-[6-(3-Phenyl-propylamino)-5,6,7,8-tetrahydro-naphthalen-1-yloxy]-nicotinamide | II | 9 | 3-phenylpropylamine | 402 |
| 75 | 6-[7-(3-Phenyl-propylamino)-5,6,7,8-tetrahydro-naphthalen-1-yloxy]-nicotinamide | II | 10 | 3-phenylpropylamine | 402 |
| 76 | 6-[5-(2-Methylsulfanyl-ethylamino)-5,6,7,8-tetrahydro-naphthalen-2-yloxy]-nicotinamide | II | 2 | 2-(methylthio)-ethylamine | 358 |
| 77 | 6-[1-(2-Methylsulfanyl-ethylamino)-indan-5-yloxy]-nicotinamide | II | 4 | 2-(methylthio)-ethylamine | 344 |
| 78 | 6-{5-[2-(3-Methoxy-phenyl)-ethylamino]-5,6,7,8-tetrahydro-naphthalen-2-yloxy}-nicotinamide | II | 2 | 3-methoxylphenethylamine | 418 |
| 79 | 6-{1-[2-(3-Methoxy-phenyl)-ethylamino]-indan-5-yloxy}-nicotinamide | II | 4 | 3-methoxylphenethylamine | 404 |
| 80 | 6-[5-(2-Dimethylamino-ethylamino)-5,6,7,8-tetrahydro-naphthalen-2-yloxy]-nicotinamide | II | 2 | N,N-dimethylaminoethylamine | 356 |
| 81 | 6-[1-(2-Dimethylamino-ethylamino)-indan-5-yloxy]-nicotinamide | II | 4 | N,N-dimethylaminoethylamine | 341 |
| 82 | 6-[5-(2-Pyrrolidin-1-yl-ethylamino)-5,6,7,8-tetrahydro-naphthalen-2-yloxy]-nicotinamide | II | 2 | 2-pyrrolidinoethylamine | 381 |
| 83 | 6-[1-(2-Pyrrolidin-1-yl-ethylamino)-indan-5-yloxy]-nicotinamide | II | 4 | 2-pyrrolidinoethylamine | 367 |
| 84 | 6-[5-(2-Pyridin-2-yl-ethylamino)-5,6,7,8-tetrahydro-naphthalen-2-yloxy]-nicotinamide | II | 2 | 2-(2-aminoethyl)pyridine | 389 |
| 85 | 6-[1-(2-Pyridin-2-yl-ethylamino)-indan-5-yloxy]-nicotinamide | II | 4 | 2-(2-aminoethyl)pyridine | 375 |
| 86 | 6-[5-(2-Morpholin-4-yl-ethylamino)-5,6,7,8-tetrahydro-naphthalen-2-yloxy]-nicotinamide | II | 2 | 4-(2-aminoethyl)-morpholine | 397 |
| 87 | 6-[1-(2-Morpholin-4-yl-ethylamino)-indan-5-yloxy]-nicotinamide | II | 4 | 4-(2-aminoethyl)-morpholine | 383 |
| 88 | 6-[1-(1,2-Diphenyl-ethylamino)-indan-5-yloxy]-nicotinamide | II | 4 | 1,2-diphenylethylamine | 450 |
| 89 | 6-{5-[2-(4-Fluoro-phenyl)-ethylamino]-5,6,7,8-tetrahydro-naphthalen-2-yloxy}-nicotinamide | II | 2 | 4-fluorophenethylamine | 406 |
| 90 | 6-{1-[2-(4-Fluoro-phenyl)-ethylamino]-indan-5-yloxy}-nicotinamide | II | 4 | 4-fluorophenethylamine | 390 |
| 91 | 6-[5-(2-Acetylamino-ethylamino)-5,6,7,8-tetrahydro-naphthalen-2-yloxy]-nicotinamide | II | 2 | N-acetyl-ethylenediamine | 369 |

-continued

| Example | IUPAC name | General Procedure | Intermed. # | Reagent | Mass (pos. ion) |
|---|---|---|---|---|---|
| 92 | 6-[1-(2-Acetylamino-ethylamino)-indan-5-yloxy]-nicotinamide | II | 4 | N-acetyl-ethylenediamine | 355 |
| 93 | 6-{5-[2-(5-Fluoro-1H-indol-3-yl)-ethylamino]-5,6,7,8-tetrahydro-naphthalen-2-yloxy}-nicotinamide | II | 2 | 5-fluorotryptamine | 445 |
| 94 | 6-{1-[2-(5-Fluoro-1H-indol-3-yl)-ethylamino]-indan-5-yloxy}-nicotinamide | II | 4 | 5-fluorotryptamine | 431 |
| 95 | 3-[6-(5-Carbamoyl-pyridin-2-yloxy)-1,2,3,4-tetrahydro-naphthalen-1-ylamino]-propionic acid isopropyl ester | II | 2 | 4-Amino-butyric acid isopropyl ester | 398 |
| 96 | 3-[5-(5-Carbamoyl-pyridin-2-yloxy)-indan-1-ylamino]-propionic acid isopropyl ester | II | 4 | 4-Amino-butyric acid isopropyl ester | 384 |
| 97 | 6-(2-Pentylamino-indan-5-yloxy)-nicotinamide | I | 15 | n-pentylamine | 340 |
| 98 | 6-(2-Pentylamino-indan-4-yloxy)-nicotinamide | I | 16 | n-pentylamine | 340 |
| 99 | 6-(2-Benzylamino-indan-5-yloxy)-nicotinamide | I | 15 | benzylamine | 360 |
| 100 | 6-(2-Benzylamino-indan-4-yloxy)-nicotinamide | I | 16 | benzylamine | 360 |
| 101 | 6-[2-(3-Phenyl-propylamino)-indan-5-yloxy]-nicotinamide | I | 15 | 3-phenylpropylamine | 388 |
| 102 | 6-[2-(3-Phenyl-propylamino)-indan-4-yloxy]-nicotinamide | I | 16 | 3-phenylpropylamine | 388 |
| 103 | 6-[2-(3-Methyl-butylamino)-indan-5-yloxy]-nicotinamide | I | 15 | isoamylamine | 340 |
| 104 | 6-[2-(3-Methyl-butylamino)-indan-4-yloxy]-nicotinamide | I | 16 | isoamylamine | 340 |
| 105 | 6-[2-(2-Phenyl-propylamino)-indan-5-yloxy]-nicotinamide | I | 15 | 2-phenylpropylamine | 388 |
| 106 | 6-[2-(2-Phenyl-propylamino)-indan-4-yloxy]-nicotinamide | I | 16 | 2-phenylpropylamine | 388 |
| 107 | 6-(2-Phenethylamino-indan-5-yloxy)-nicotinamide | I | 15 | phenethylamine | 374 |
| 108 | 6-(2-Phenethylamino-indan-4-yloxy)-nicotinamide | I | 16 | phenethylamine | 374 |
| 109 | 6-{2-[(5-Fluoro-1H-indol-3-ylmethyl)-amino]-indan-5-yloxy}-nicotinamide | I | 15 | 5-fluorotryptamine | 417 |
| 110 | 6-{2-[(5-Fluoro-1H-indol-3-ylmethyl)-amino]-indan-4-yloxy}-nicotinamide | I | 16 | 5-fluorotryptamine | 417 |
| 111 | 6-[2-(3-Dimethylamino-2,2-dimethyl-propylamino)-indan-5-yloxy]-nicotinamide | I | 15 | N,N,2,2-tetramethyl-1,3-propane-diamine | 382 |
| 112 | 6-[2-(3-Dimethylamino-2,2-dimethyl-propylamino)-indan-4-yloxy]-nicotinamide | I | 16 | N,N,2,2-tetramethyl-1,3-propane-diamine | 382 |
| 113 | 6-{5-[(Benzo[b]thiophen-3-ylmethyl)-amino]-5,6,7,8-tetrahydro-naphthalen-2-yloxy}-nicotinamide | II | 2 | 1-benzothiophen-3-ylmethylamine | 430 |
| 114 | 6-{1-[(Benzo[b]thiophen-3-ylmethyl)-amino]-indan-5-yloxy}-nicotinamide | II | 4 | 1-benzothiophen-3-ylmethylamine | 416 |
| 115 | 6-[5-(2-Methoxy-ethylamino)-5,6,7,8-tetrahydro-naphthalen-2-yloxy]-nicotinamide | II | 2 | 2-methoxyethylamine | 342 |
| 116 | 6-[1-(2-Methoxy-ethylamino)-indan-5-yloxy]-nicotinamide | II | 4 | 2-methoxyethylamine | 328 |
| 117 | 6-{5-[2-(3-Trifluoromethyl-phenyl)-ethylamino]-5,6,7,8-tetrahydro-naphthalen-2-yloxy}-nicotinamide | II | 2 | 3-(trifluoromethyl)-phenethylamine | 456 |
| 118 | 6-{1-[2-(3-Trifluoromethyl-phenyl)-ethylamino]-indan-5-yloxy}-nicotinamide | II | 4 | 3-(trifluoromethyl)-phenethylamine | 442 |

-continued

| Example | IUPAC name | General Procedure | Intermed. # | Reagent | Mass (pos. ion) |
|---|---|---|---|---|---|
| 119 | 6-[5-(2-m-Tolyl-ethylamino)-5,6,7,8-tetrahydro-naphthalen-2-yloxy]-nicotinamide | II | 2 | 3-methyl-phenethylamine | 402 |
| 120 | 6-{5-[2-(4-Fluoro-phenyl)-1,1-dimethyl-ethylamino]-5,6,7,8-tetrahydro-naphthalen-2-yloxy}-nicotinamide | II | 2 | 1,1-dimethyl-2-(4-fluorophenyl)-ethylamine | 299 |
| 121 | 6-{1-[2-(4-Fluoro-phenyl)-1,1-dimethyl-ethylamino]-indan-5-yloxy}-nicotinamide | II | 4 | 1,1-dimethyl-2-(4-fluorophenyl)-ethylamine | 285 |
| 122 | 6-[5-(3-Hydroxy-propylamino)-5,6,7,8-tetrahydro-naphthalen-2-yloxy]-nicotinamide | II | 2 | 3-hydroxypropylamine | 343 |
| 123 | 6-[1-(3-Hydroxy-propylamino)-indan-5-yloxy]-nicotinamide | II | 4 | 3-hydroxypropylamine | 329 |
| 124 | 6-[5-(2,2,2-Trifluoro-ethylamino)-5,6,7,8-tetrahydro-naphthalen-2-yloxy]-nicotinamide | II | 2 | 2,2,2-trifluoroethylamine | 299 |
| 125 | 6-[1-(2,2,2-Trifluoro-ethylamino)-indan-5-yloxy]-nicotinamide | II | 4 | 2,2,2-trifluoroethylamine | 285 |
| 126 | 6-[5-(2,2-Diphenyl-ethylamino)-5,6,7,8-tetrahydro-naphthalen-2-yloxy]-nicotinamide | II | 2 | 2,2-diphenylethylarmine | 464 |
| 127 | 6-[5-(4-Phenyl-piperidin-1-yl)-5,6,7,8-tetrahydro-naphthalen-2-yloxy]-nicotinamide | III | 13 | 4-phenylpiperidine | 428 |
| 128 | 6-[1-(4-Phenyl-piperidin-1-yl)-indan-5-yloxy]-nicotinamide | III | 14 | 4-phenylpiperidine | 414 |
| 129 | 6-[5-(Benzyl-methyl-amino)-5,6,7,8-tetrahydro-naphthalen-2-yloxy]-nicotinamide | III | 13 | N-methylbenzylamine | 388 |
| 130 | 6-[1-(Benzyl-methyl-amino)-indan-5-yloxy]-nicotinamide | III | 14 | N-methylbenzylamine | 374 |
| 131 | 6-[5-(3,4-Dihydro-1H-isoquinolin-2-yl)-5,6,7,8-tetrahydro-naphthalen-2-yloxy]-nicotinamide | III | 13 | 1,2,3,4-tetrahydro-isoquinoline | 400 |
| 132 | 6-[1-(3,4-Dihydro-1H-isoquinolin-2-yl)-indan-5-yloxy]-nicotinamide | III | 14 | 1,2,3,4-tetrahydro-isoquinoline | 386 |
| 133 | 6-(5-Thiomorpholin-4-yl-5,6,7,8-tetrahydro-naphthalen-2-yloxy)-nicotinamide | III | 13 | thio-morpholine | 370 |
| 134 | 6-(1-Thiomorpholin-4-yl-indan-5-yloxy)-nicotinamide | III | 14 | thio-morpholine | 356 |
| 135 | 2-[6-(5-Carbamoyl-pyridin-2-yloxy)-1,2,3,4-tetrahydro-naphthalen-1-yl]-1,2,3,4-tetrahydro-isoquinoline-3-carboxylic acid tert-butylamide | III | 13 | 1,2,3,4-tetrahydro-isoquinoline-3-carboxylic acid tert-butylamide | 499 |
| 136 | 2-[6-(5-Carbamoyl-pyridin-2-yloxy)-1,2,3,4-tetrahydro-naphthalen-1-yl]-1,2,3,4-tetrahydro-isoquinoline-3-carboxylic acid tert-butylamide | III | 13 | 1,2,3,4-tetrahydro-isoquinoline-3-carboxylic acid tert-butylamide | 499 |
| 137 | 6-[5-(5-Oxo-[1,4]diazepan-1-yl)-5,6,7,8-tetrahydro-naphthalen-2-yloxy]-nicotinamide | III | 13 | 2,3,6,7-tetrahydro-(1H)-1,4-diazepin-5(4H)-one | 381 |
| 138 | 6-[1-(5-Oxo-[1,4]diazepan-1-yl)-indan-5-yloxy]-nicotinamide | III | 14 | 2,3,6,7-tetrahydro-(1H)-1,4-diazepin-5(4H)-one | 367 |

| Example | IUPAC name | General Procedure | Intermed. # | Reagent | Mass (pos. ion) |
|---|---|---|---|---|---|
| 139 | 6-[5-(Methyl-phenethyl-amino)-5,6,7,8-tetrahydro-naphthalen-2-yloxy]-nicotinamide | III | 13 | N-methyl-phenethylamine | 402 |
| 140 | 6-[1-(3-Acetylamino-pyrrolidin-1-yl)-indan-5-yloxy]-nicotinamide | III | 14 | 3-acetamido-pyrrolidine | 381 |
| 141 | 6-[1-(3-Phenyl-piperidin-1-yl)-indan-5-yloxy]-nicotinamide | III | 14 | 3-phenylpiperidine | 414 |
| 142 | 6-[1-(3-Phenyl-pyrrolidin-1-yl)-indan-5-yloxy]-nicotinamide | III | 14 | 3-phenylpyrrolidine | 400 |
| 143 | 6-[1-(3-Propylamino-propylamino)-indan-5-yloxy]-nicotinamide | II | 4 | N-propyl-1,3-propanediamine | 369 |
| 144 | 6-[1-(3,3-Dimethyl-butylamino)-indan-5-yloxy]-nicotinamide | II | 4 | 3,3-dimethyl,-butylamine | 354 |
| 145 | 6-(1-Decylamino-indan-5-yloxy)-nicotinamide | II | 4 | n-decylamine | 410 |
| 146 | 6-[1-(2-Ethyl-hexylamino)-indan-5-yloxy]-nicotinamide | II | 4 | 2-ethyl-hexylamine | 382 |
| 147 | 6-{1-[(Tetrahydro-furan-2-ylmethyl)-amino]-indan-5-yloxy}-nicotinamide | II | 4 | tetrahydro-furfurylamine | 354 |
| 148 | 6-(1-Cycloheptylamino-indan-5-yloxy)-nicotinamide | II | 4 | cycloheptylamine | 366 |
| 149 | 6-{1-[2-(1-Methyl-pyrrolidin-2-yl)-ethylamino]-indan-5-yloxy}-nicotinamide | II | 4 | 2-(2-aminoethyl)-1-methylpyrrolidine | 381 |
| 150 | 6-(1-Cyclopropylamino-indan-5-yloxy)-nicotinamide | II | 4 | cyclopropylamine | 310 |
| 151 | 6-[1-(1,3-Dimethyl-butylamino)-indan-5-yloxy]-nicotinamide | II | 4 | 1,3-dimethyl-butylamine | 354 |
| 152 | 6-(1-Cyclooctylamino-indan-5-yloxy)-nicotinamide | II | 4 | cyclooctylamine | 380 |
| 153 | 6-[1-(2,3-Dimethyl-cyclohexylamino)-indan-5-yloxy]-nicotinamide | II | 4 | 2,3-dimethylcyclohexylamine, cis/trans mixture | 380 |
| 154 | 6-(1-Cyclobutylamino-indan-5-yloxy)-nicotinamide | II | 4 | cyclobutylamine | 324 |
| 155 | 6-(1-Cyclopentylamino-indan-5-yloxy)-nicotinamide | II | 4 | cyclopentylamine | 338 |
| 156 | 6-[1-(Cyclohexylmethyl-amino)-indan-5-yloxy]-nicotinamide | II | 4 | aminomethyl-cyclohexane | 366 |
| 157 | 6-{1-[(1-Ethyl-pyrrolidin-2-ylmethyl)-amino]-indan-5-yloxy}-nicotinamide | II | 4 | 2-aminomethyl-1-ethylpyrrolidine | 381 |
| 158 | 6-[1-(3-Cyclohexylamino-propylamino)-indan-5-yloxy]-nicotinamide | II | 4 | 3-Cyclohexylamino-propylamine | 409 |
| 159 | 6-[1-(3-Methyl-cyclohexylamino)-indan-5-yloxy]-nicotinamide | II | 4 | 3-methyl-cyclohexylamine | 366 |
| 160 | 6-(1-Cyclohexylamino-indan-5-yloxy)-nicotinamide | II | 4 | cyclohexylamine | 350 |
| 161 | 6-[1-(1-Isopropyl-2-methyl-propylamino)-indan-5-yloxy]-nicotinamide | II | 4 | 3-amino-2,4-dimethyl-pentane | 366 |
| 162 | 6-[1-(2-Cyclohex-1-enyl-ethylamino)-indan-5-yloxy]-nicotinamide | II | 4 | 2-(1-cyclohexenyl)-ethylamine | 378 |
| 163 | 6-[1-(2-Methyl-butylamino)-indan-5-yloxy]-nicotinamide | II | 4 | 2-methylbutylamine | 340 |
| 164 | 6-[1-(4-Hydroxy-cyclohexylamino)-indan-5-yloxy]-nicotinamide | II | 4 | trans-4-Hydroxy-cyclohexylamine | 368 |
| 165 | 6-[1-(1,4-Dimethyl-pentylamino)-indan-5-yloxy]-nicotinamide | II | 4 | 2,4-dimethylpentylamine | 368 |
| 166 | 6-[1-(1-Cyclohexyl-ethylamino)-indan-5-yloxy]-nicotinamide | II | 4 | 1-Cyclohexyl-ethylamine | 380 |

-continued

| Example | IUPAC name | General Procedure | Intermed. # | Reagent | Mass (pos. ion) |
|---|---|---|---|---|---|
| 167 | 6-[1-(3,3,5-Trimethyl-cyclohexylamino)-indan-5-yloxy]-nicotinamide | II | 4 | 3,3,5-Trimethyl-cyclohexylamine | 394 |
| 168 | 6-[1-(2-Carbamoyl-cyclohexylamino)-indan-5-yloxy]-nicotinamide | II | 4 | 2-amino-cyclohexane-carboxamide | 395 |
| 169 | 6-[1-(Cyclopropylmethyl-amino)-indan-5-yloxy]-nicotinamide | II | 4 | cyclopropyl-methylamine | 324 |
| 170 | 6-[1-(3-Butoxy-propylamino)-indan-5-yloxy]-nicotinamide | II | 4 | 3-butoxypropylamine | 384 |
| 171 | 6-[1-(2,2,3,3,4,4,4-Heptafluoro-butylamino)-indan-5-yloxy]-nicotinamide | II | 4 | 2,2,3,3,4,4,4-Heptafluoro-butylamine | 450 |
| 172 | 6-{1-[3-(2-Oxo-pyrrolidin-1-yl)-propylamino]-indan-5-yloxy}-nicotinamide | II | 4 | 1-(2-Amino-ethyl)-pyrrolidin-2-one | 395 |
| 173 | 6-[1-(3-Azepan-1-yl-propylamino)-indan-5-yloxy]-nicotinamide | II | 4 | 3-hexamethyleneimino-1-propylamine | 409 |
| 174 | 6-[1-(2,2,3,3,3-Pentafluoro-propylamino)-indan-5-yloxy]-nicotinamide | II | 4 | 2,2,3,3,3-Pentafluoro-propylamine | 402 |
| 175 | 6-{1-[(2-Hydroxy-cyclooctylmethyl)-amino]-indan-5-yloxy}-nicotinamide | II | 4 | cis-2-aminomethyl-cyclooctanol | 410 |
| 176 | 6-[1-(Bicyclohexyl-2-ylamino)-indan-5-yloxy]-nicotinamide | II | 4 | 2-aminobicyclohexyl | 434 |
| 177 | 6-[1-(2-Hydroxy-cyclohexylamino)-indan-5-yloxy]-nicotinamide | II | 4 | 2-hydroxy-cyclohexylamine | 368 |
| 178 | 6-{1-[2-(2-Methyl-cyclohexyl)-ethylamino]-indan-5-yloxy}-nicotinamide | II | 4 | 2-(2-Methyl-cyclohexyl)-ethylamine | 394 |
| 179 | 6-{1-[2-(4-Methyl-cyclohexyl)-ethylamino]-indan-5-yloxy}-nicotinamide | II | 4 | 2-(4-methylcyclohexyl)-ethylamine | 394 |
| 180 | 6-[1-(2-Cyclopentyl-ethylamino)-indan-5-yloxy]-nicotinamide | II | 4 | 2-cyclopentyl-ethylamine | 366 |
| 181 | 6-[1-(Phenethylamino-methyl)-indan-5-yloxy]-nicotinamide | I | 17 | phenethylamine | 388 |
| 182 | 6-[8-Phenethylamino-methyl)-5,6,7,8-tetrahydro-naphthalen-2-yloxy]-nicotinamide | I | 19 | phenethylamine | 402 |
| 183 | 6-[3-(Phenethylamino-methyl)-indan-5-yloxy]-nicotinamide | I | 18 | phenethylamine | 388 |
| 184 | 6-[5-(Phenethylamino-methyl)-5,6,7,8-tetrahydro-naphthalen-1-yloxy]-nicotinamide | I | 20 | phenethylamine | 402 |
| 185 | 6-[1-(Benzylamino-methyl)-indan-5-yloxy]-nicotinamide | I | 17 | benzylamine | 374 |
| 186 | 6-[8-(Benzylamino-methyl)-5,6,7,8-tetrahydro-naphthalen-2-yloxy]-nicotinamide | I | 19 | benzylamine | 388 |
| 187 | 6-[3-(Benzylamino-methyl)-indan-5-yloxy]-nicotinamide | I | 18 | benzylamine | 374 |
| 188 | 6-[5-(Benzylamino-methyl)-5,6,7,8-tetrahydro-naphthalen-1-yloxy]-nicotinamide | I | 20 | benzylamine | 388 |
| 189 | 6-{1-[(3-Methyl-butylamino)-methyl]-indan-5-yloxy}-nicotinamide | I | 17 | isoamylamine | 354 |
| 190 | 6-{8-[(3-Methyl-butylamino)-methyl]-5,6,7,8-tetrahydro-naphthalen-2-yloxy}-nicotinamide | I | 19 | isoamylamine | 368 |
| 191 | 6-{3-[(3-Methyl-butylamino)-methyl]-indan-5-yloxy}-nicotinamide | I | 18 | isoamylamine | 354 |

-continued

| Example | IUPAC name | General Procedure | Intermed. # | Reagent | Mass (pos. ion) |
|---|---|---|---|---|---|
| 192 | 6-{5-[(3-Methyl-butylamino)-methyl]-5,6,7,8-tetrahydro-naphthalen-1-yloxy}-nicotinamide | I | 20 | isoamylamine | 368 |
| 193 | 6-{1-[(2-Cyclohexyl-ethylamino)-methyl]-indan-5-yloxy}-nicotinamide | I | 17 | 2-cyclohexyl-ethylamine | 394 |
| 194 | 6-{8-[(2-Cyclohexyl-ethylamino)-methyl]-5,6,7,8-tetrahydro-naphthalen-2-yloxy}-nicotinamide | I | 19 | 2-cyclohexyl-ethylamine | 408 |
| 195 | 6-{5-[(2-Cyclohexyl-ethylamino)-methyl]-5,6,7,8-tetrahydro-naphthalen-1-yloxy}-nicotinamide | I | 20 | 2-cyclohexyl-ethylamine | 408 |
| 196 | 6-{1-[(Cyclohexylmethyl-amino)-methyl]-indan-5-yloxy}-nicotinamide | I | 17 | aminomethyl-cyclohexane | 380 |
| 197 | 6-{8-[(Cyclohexylmethyl-amino)-methyl]-5,6,7,8-tetrahydro-naphthalen-2-yloxy}-nicotinamide | I | 19 | aminomethyl-cyclohexane | 394 |
| 198 | 6-{3-[(Cyclohexylmethyl-amino)-methyl]-indan-5-yloxy}-nicotinamide | I | 18 | aminomethyl-cyclohexane | 380 |
| 199 | 6-{5-[(Cyclohexylmethyl-amino)-methyl]-5,6,7,8-tetrahydro-naphthalen-1-yloxy}-nicotinamide | I | 20 | aminomethyl-cyclohexane | 394 |
| 200 | 6-{1-[(2-Cyclopentyl-ethylamino)-methyl]-indan-5-yloxy}-nicotinamide | I | 17 | 2-cyclopentyl-ethylamine | 380 |

EXAMPLE 201

6-{5-[(3-Methyl-butylamino)-methyl]-5,6,7,8-tetrahydro-naphthalen-2-yloxy}-nicotinamide. 2116496

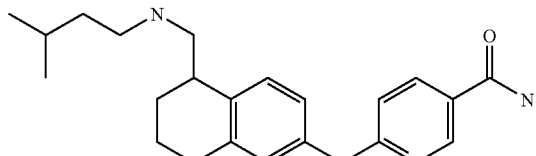

Add isovaleraldehyde (64.5 mg, 0.750 mmol) to a solution of 6-(5-aminomethyl-5,6,7,8-tetrahydro-naphthalen-2-yloxy)-nicotinamide (intermediate 21, 148 mg, 0.500 mmol) dissolved in MeOH (5 mL) and stir at ambient temperature for 1.5 hours before adding NaBH$_4$ (38 mg, 1.00 mmol). After stirring for an additional two hours, concentrate the reaction mixture and redissolved in EtOAc. Wash the EtOAc solution with 5% aq. KOH and brine before drying (MgSO$_4$) and concentrating. Purify on silica gel (5% (1N NH$_3$/MeOH)/DCM) to obtain 123 mg of the title compound as a white foam.

Mass spectrum (ion spray): m/z=368 (M+1); $^1$HNMR (CDCl$_3$): 8.59 (s, 1H), 8.15 (d, 1H), 7.25 (d, 1H), 6.94 (d, 1H), 6.89 (d, 1H), 6.85 (s, 1H), 5.82 (br. s, 2H), 2.97 (m, 1H), 2.84 (m, 2H), 2.76 (m, 2H), 2.66 (m, 2H), 1.85 (m, 3H), 1.74 (m 1H), 1.62 (m, 1H), 1.41 (m, 2H), 0.90 (d, 6H).

EXAMPLE 202

6-{5-[(3,3-Dimethyl-butylamino)-methyl]-5,6,7,8-tetrahydro-naphthalen-1-yloxy}-nicotinamide

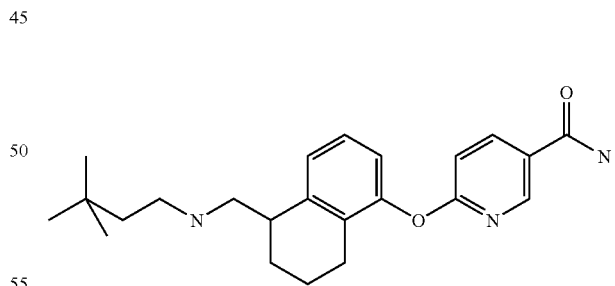

Using a method similar to Example 201, using 6-(5-aminomethyl-5,6,7,8-tetrahydro-naphthalen-1-yloxy)-nicotinamide (intermediate 20, 148 mg, 0.500 mmol), 3,3-dimethyl-butyraldehyde (75 mg, 0.750 mmol), and NaBH$_4$ (38 mg, 1.00 mmol) gives the title compound (130 mg) as a white foam. Mass spectrum (ion spray): m/z=382 (M+1); $^1$HNMR (CDCl$_3$): 8.55 (s, 1H), 8.14 (d, 1H), 7.22-7.14 (m, 2H), 6.90

(m, 2H), 5.76 (br. s, 2H), 3.03 (m, 1H), 2.92-2.80 (m, 2H), 2.71-2.55 (m, 3H), 2.49-2.41 (m, 1H), 1.85-1.65 (m, 4H), 1.42 (t, 2H), 0.90 (s, 9H).

EXAMPLE 203

6-(5-Hexylaminomethyl-5,6,7,8-tetrahydro-naphthalen-1-yloxy)-nicotinamide

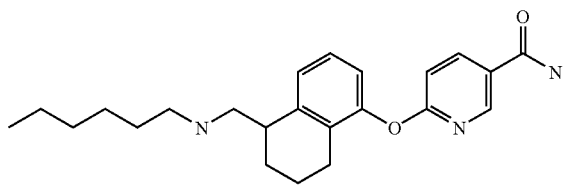

Using a method similar to Example 201, using 6-(5-aminomethyl-5,6,7,8-tetrahydro-naphthalen-1-yloxy)-nicotinamide (intermediate 20, 148 mg, 0.500 mmol), hexanal (75 mg, 0.750 mmol), and NaBH$_4$ (38 mg, 1.00 mmol) gives the title compound (110 mg) as a colorless glass. Mass spectrum (ion spray): m/z=382 (M+1); $^1$HNMR (CDCl$_3$): 8.57 (s, 1H), 8.15 (d, 1H), 7.21-7.14 (m, 2H), 6.90 (m, 2H), 6.05 (br. s, 2H), 3.01)m, 1H), 2.90-2.79 (m, 2H), 2.69-2.55 (m, 3H), 2.50-2.42 (m, 1H), 1.84-1.64 (m, 4H), 1.49 (m, 2H), 1.29 (m, 6H), 0.89 (t, 3H).

EXAMPLE 204

6-(5-Cyclohexylaminomethyl-5,6,7,8-tetrahydro-naphthalen-1-yloxy)-nicotinamide

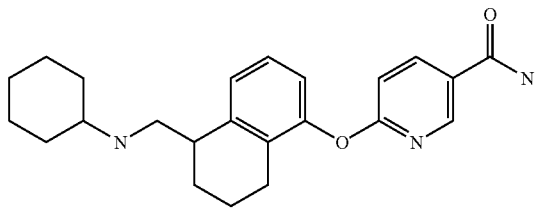

Add NaBH$_3$CN (63 mg, 1.00 mmol) to a solution of 6-(5-aminomethyl-5,6,7,8-tetrahydro-naphthalen-1-yloxy)-nicotinamide (intermediate 20, 148 mg, 0.500 mmol) and cyclohexanone (98 mg, 1.00 mmol) dissolved in 5% AcOH/MeOH (5 ml) and stir at ambient temperature for 16 hours. Concentrate the reaction mixture and redissolved in EtOAc. Wash the EtOAc solution with 5% aq. KOH and brine before drying (MgSO$_4$) and concentrating. Purify on silica gel (5% (1N NH$_3$/MeOH)/DCM) to obtain 145 mg of the title compound as a white foam. Mass spectrum (ion spray): m/z=380 (M+1); $^1$HNMR (CDCl$_3$): 8.56 (s, 1H), 8.15 (d, 1H), 7.22-7.14 (m, 2H), 6.90 (m, 2H), 5.79 (br. s, 2H), 2.99 (m, 1H), 2.96-2.79 (m, 2H), 2.63-2.41 (m, 3H), 1.91 (m, 2H), 1.85-1.67 (m, 6H), 1.31-1.04 (m, 6H).

EXAMPLE 205

6-(5-Cyclopentylaminomethyl-5,6,7,8-tetrahydro-naphthalen-1-yloxy)-nicotinamide

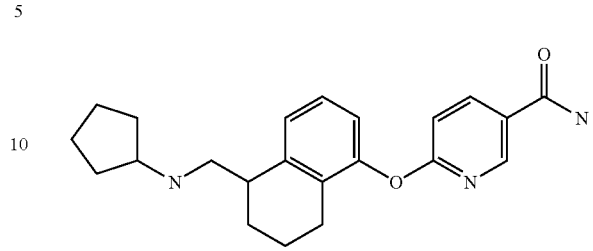

Using a method similar to Example 204, using 6-(5-aminomethyl-5,6,7,8-tetrahydro-naphthalen-1-yloxy)-nicotinamide (intermediate 20, 297 mg, 1.00 mmol), cyclopentanone (168 mg, 2.00 mmol), and NaBH$_3$CN (125 mg, 2.00 mmol) gives the title compound (137 mg) as a white foam. Mass spectrum (ion spray): m/z=366 (M+1); $^1$HNMR (CDCl$_3$): 8.56 (s, 1H), 8.15 (d, 1H), 7.22-7.15 (m 2H), 6.93-6.89 (m, 2H), 5.82 (br. s, 2H), 3.11 (m, 1H), 3.02 (m, 1H), 2.92-2.78 (m, 2H), 2.63-2.42 (m, 2H), 1.91-1.50 (m, 10H), 1.35 (m, 2H).

EXAMPLE 206

6-[5-(Isopropylamino-methyl)-5,6,7,8-tetrahydro-naphthalen-1-yloxy]-nicotinamide

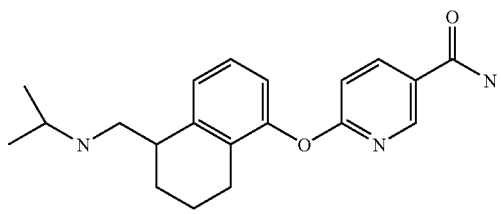

Using a method similar to Example 204, using 6-(5-aminomethyl-5,6,7,8-tetrahydro-naphthalen-1-yloxy)-nicotinamide (intermediate 20, 297 mg, 1.00 mmol), acetone (116 mg, 2.00 mmol), and NaBAH$_3$CN (125 mg, 2.00 mmol) gives the title compound (139 mg) as a white foam. Mass spectrum (ion spray): m/z=340 (M+1); $^1$HNMR (CDCl$_3$): 8.57 (s, 1H), 8.13 (d, 1H), 7.21-7.13 (m, 2H), 6.90-6.87 (m, 2H), 6.27 (br. s, 2H), 2.97 (m, 1H), 2.91-2.75 (m, 3H), 2.62-2.41 (m, 2H), 1.83-1.63 (m, 4H), 1.07 (d, 6H).

EXAMPLE 207

6-{5-[(Tetrahydro-pyran-4-ylamino)-methyl]-5,6,7,8-tetrahydro-naphthalen-1-yloxy}-nicotinamide

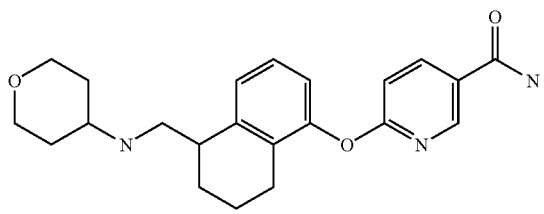

Using a method similar to Example 204, using 6-(5-aminomethyl-5,6,7,8-tetrahydro-naphthalen-1-yloxy)-nicotinamide (intermediate 20, 238 mg, 0.800 mmol), tetrahydro-4H-pyran-4-one (160 mg, 1.60 mmol), and NaBH$_3$CN (100 mg, 1.60 mmol) gives the title compound (138 mg) as a white foam. Mass spectrum (ion spray): m/z=382 (M+1); $^1$HNMR (CDCl$_3$): 8.57 (s, 1H), 8.16 (d, 1H), 7.23-7.16 (m, 2H), 6.94-6.90 (m, 2H), 5.86 (br. s, 2H), 4.00 (d, 2H), 3.40 (t, 2H), 3.15-2.78 (m, 3H), 2.65-2.41 (m, 2H), 1.97-1.46 (m, 9H).

EXAMPLE 208

6-{5-[(4-Methyl-pentylamino)-methyl]-5,6,7,8-tetrahydro-naphthalen-1-yloxy}-nicotinamide

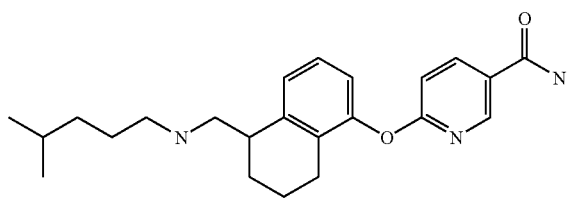

Add NaH (60% oil suspension, 30 mg, 0.750 mmol) to a solution of [5-(5-cyano-pyridin-2-yloxy)-1,2,3,4-tetrahydro-naphthalen-1-ylmethyl]-carbamic acid tert-butyl ester (Intermediate 22, 189 mg, 0.500 mmol) and DMF (5 ml) stirring at ambient temperature under nitrogen. After 20 minutes, add 1-bromo-4-methylpentane (247 mg, 1.50 mmol) and heat the mixture at 60° C. overnight. After cooling, pour the mixture into water and extract with EtOAc (2×). Wash the extract with water and brine before drying ((MgSO$_4$) and concentrating. Purify on silica gel (20% EtOAc/Hexane) to obtain 111 mg of [5-(5-cyano-pyridin-2-yloxy)-1,2,3,4-tetrahydro-naphthalen-1-ylmethyl]-(4-methyl-pentyl)-carbamic acid tert-butyl ester as a colorless glass.

Add 30% aq. H$_2$O$_2$ (239 uL) to a suspension of [5-(5-cyano-pyridin-2-yloxy)-1,2,3,4-tetrahydro-naphthalen-1-ylmethyl]-(4-methyl-pentyl)-carbamic acid tert-butyl ester (111 mg, 0.239 mmol), K$_2$CO$_3$ (16 mg, 0.120 mmol) and DMSO (3 ml) stirring in an ice/water bath. After 1.5 hours, pour the reaction mixture into water and extract with EtOAc. Wash the extract with water and brine before drying (MgSO$_4$) and concentrating to give [5-(5-Carbamoyl-pyridin-2-yloxy)-1,2,3,4-tetrahydro-naphthalen-1-ylmethyl]-(4-methyl-pentyl)-carbamic acid tert-butyl ester (114 mg) as a white foam. Use this material without further purification.

Add TFA (540 mg, 4.73 mmol) to a solution of [5-(5-Carbamoyl-pyridin-2-yloxy)-1,2,3,4-tetrahydro-naphthalen-1-ylmethyl]-(4-methyl-pentyl)-carbamic acid tert-butyl ester (114 mg, 0.236 mmol) and DCM (3 ml) stirring under nitrogen at ambient temperature. After 18 hours, concentrate the mixture, redissolve in EtOAc and wash with 1M aq. K$_2$CO$_3$, water, and brine. Dry (MgSO$_4$), concentrate, and purify on silica gel (5% (1N NH$_3$/MeOH)/DCM) to obtain the title compound (80 mg) as an off-white solid. Mass spectrum (ion spray): m/z=382 (M+1); $^1$HNMR (CDCl$_3$): 8.56 (s, 1H), 8.15 (d, 1H), 7.21-7.13 (m, 2H), 6.90 (m, 2H), 6.04 (br. s, 2H), 3.01 (m, 1H), 2.90-2.79 (m, 2H), 2.68-2.55 (m, 3H), 2.49-2.41 (m, 1H), 1.84-1.64 (m, 4H), 1.57-1.46 (m, 3H), 1.19 (m, 2H), 0.87 (d, 6H).

EXAMPLE 209

6-{5-[(2-Cyclopropyl-ethylamino)-methyl]-5,6,7,8-tetrahydro-naphthalen-1-yloxy}-nicotinamide

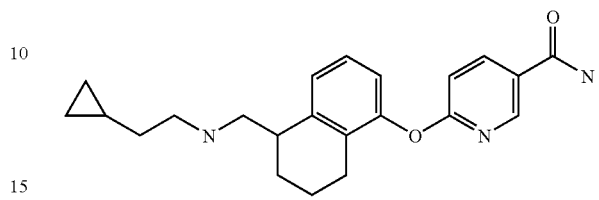

Using a method similar to Example 208, using [5-(5-cyano-pyridin-2-yloxy)-1,2,3,4-tetrahydro-naphthalen-1-ylmethyl]-carbamic acid tert-butyl ester (Intermediate 22, 379 mg, 1.00 mmol), toluene-4-sulfonic acid 2-cyclopropyl-ethyl ester (Tetrahedron (1986), 42(4), 1093-108, 721 mg, 3.00 mmol), and NaH (60% oil suspension, 80 mg, 2.00 mmol) gives the title compound (135 mg) as a white foam. Mass spectrum (ion spray): m/z=366 (M+1); $^1$HNMR (CDCl$_3$): 8.56 (s, 1H), 8.15 (d, 1H), 7.23-7.15 (m, 2H), 6.92 (m, 2H), 5.77 (br. s, 2H), 3.05 (m, 1H), 2.94-2.74 (m, 4H), 2.64-2.43 (m, 2H), 1.87-1.58 (m, 4H), 1.44 (m, 2H), 0.68 (m, 1H), 0.44 (m, 2H), 0.07 (m, 2H).

EXAMPLE 210

4-{1-[2-(3-Fluoro-phenyl)-ethylamino]-indan-5-yloxy}-benzamide

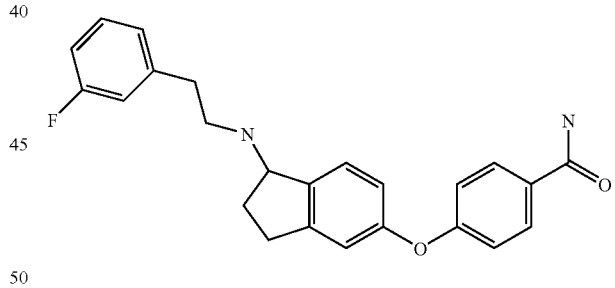

In a round bottom flask, combine 4-(1-Oxo-indan-5-yloxy)-benzamide (Intermediate 24, 45.0 mg, 0.17 mmol), m-Fluorophenethylamine (33 uL, 0.25 mmol), THF (5 mL), and Ti(OiPr)$_4$ (0.1 mL, 0.27 mmol) at 0° C. under nitrogen atmosphere. Stir the reaction for 3 hours then add TiCl$_4$ (0.3 mL, 0.27 mmol) at 0° C. For the next 2 hours, warm the reaction to room temperature and then add BH$_3$SMe$_2$ (0.09 mL, 0.17 mmol). Stir the reaction at room temperature for 12 hours, then add 1N NaOH (aq) and stir for 2 hours. Centrifuge and decant the reaction into a separatory funnel and wash the organic phase with water and dry over Na$_2$SO$_4$. Concentrate the reaction under reduced pressure and purify using reverse phase chromatography (5% to 95% 0.001% TFA buffer in acetonitrile/water) to afford 3.8 mg, 0.01 mmol (6% yield) of the title compound:

EXAMPLE 211

4-(1-Phenethylamino-indan-5-yloxy)-benzamide

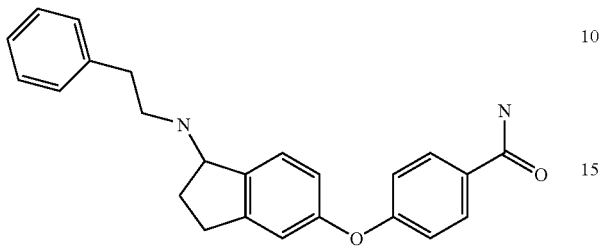

Using a method similar to Example 210, using Phenethylamine (32 uL, 0.25 mmol) gives 4.0 mg (6% yield) of the title compound:

EXAMPLE 212

4-(5-Benzylamino-5,6,7,8-tetrahydro-naphthalen-2-yloxy)-benzamide

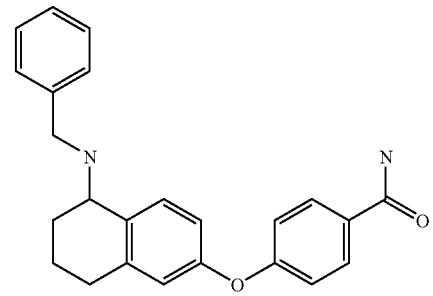

Combine 4-(5-Oxo-5,6,7,8-tetrahydro-naphthalen-2-yloxy)-benzamide (Intermediate 26, 120.0 mg, 0.43 mmol), Benzylamine (70 uL, 0.64 mmol), THF (3 mL), and Ti(OiPr)$_4$ (0.2 mL, 0.68 mmol) at 0° C. Stir the reaction for 12 hours allowing it to come to room temperature and then add TiCl$_4$ (0.7 mL, 0.68 mmol) at 0° C. After reaction stirs for 3 hours, add BH$_3$SMe$_2$ at room temperature. After the reaction stirs for 72 hours, add 1N NaOH aq (6 mL) at room temperature. Upon addition, a precipitate forms. Allow the reaction to stir for an additions 12 hours, centrifuge, and decant off aqueous and organic layers. Separate the organic layer and concentrate. Add the organic mixture to a 2 g SCX column, wash with MeOH, and elute with 1N NH$_3$ MeOH. Purify using reverse phase chromatography (5% to 95% 0.001% TFA buffer in acetonitrile/water) to afford 19.4 mg, 0.05 mmol (12% yield) of the title compound: $^1$H NMR (500 MHz, CDCl$_3$); 1.7-1.8 (2H, m), 1.9-2.1 (3H, m), 2.6-2.9 (2H, m), 3.8-4.0 (3H, m), 6.7-6.9 (2H, m), 6.9-7.0 (2H, m), 7.2-7.5 (6H, m), 7.7-7.9 (2H,m); MS m/z 284 (M of SM+3).

EXAMPLE 213

4-{5-[2-(3-Fluoro-phenyl)-ethylamino]-5,6,7,8-tetrahydro-naphthalen-2-yloxy}-benzamide

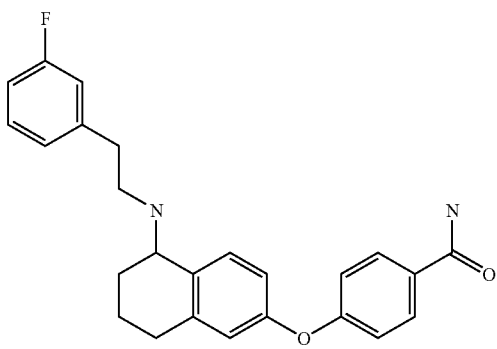

Using a method similar to Example 212, using m-Fluorophenethylamine (84 uL, 0.64 mmol) gives 26.5 mg (15% yield) of the title compound: $^1$H NMR (500 MHz, CDCl$_3$); 1.6-1.8 (1H, m), 1.8-2.0 (3H, m), 2.5-3.0 (6H, m), 3.7-3.8 (1H, m), 5.6-6.1 (2H, br d), 6.6-7.0 (7H, m), 7.1-7.3 (2H, m), 7.7-7.9 (2H, m); MS m/z 250 (M of SM+3).

EXAMPLE 214

4-[5-(3-Methyl-butylamino)-5,6,7,8-tetrahydro-naphthalen-2-yloxy]-benzamide

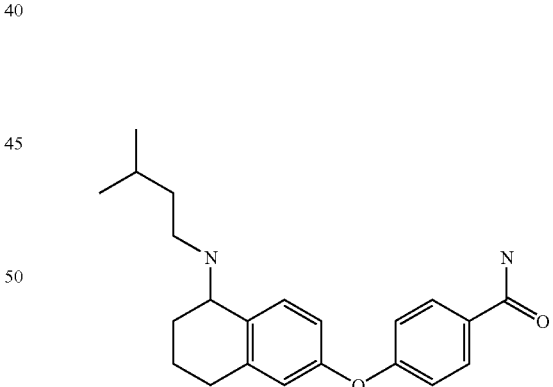

Using a method similar to Example 212, using Isoamylamine (74 uL, 0.64 mmol) gives 45.0 mg (30% yield) of the title compound: $^1$H NMR (500 MHz, CDCl$_3$); 0.8-1.0 (6H, m), 1.3-1.5 (2H, m), 1.5-1.8 (2H, m), 1.8-2.0 (3H, m), 2.6-2.8 (4H, m), 3.7-3.8 (1H, m), 5.8-6.2 (2H, br s), 6.7-6.9 (2H, m), 6.9-7.0 (2H,m), 7.2-7.4 (1H,m), 7.7-7.8 (2H, m); MS m/z 353 (M +1) and 284 (M of SM+3).

EXAMPLE 215

4-(5-Phenethylamino-5,6,7,8-tetrahydro-naphthalen-2-yloxy)-benzamide

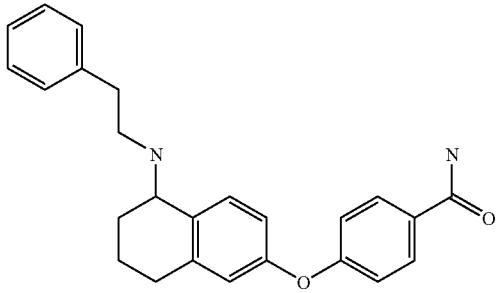

Using a method similar to Example 212, using Phenethylamine (80 uL, 0.64 mmol) gives 21.7 mg (13% yield) of the title compound: $^1$H NMR (500 MHz, CDCl$_3$); 1.5-2.2 (5H, m), 2.5-3.1 (6H, m), 3.2-3.4 (1H, m), 3.7-3.9 (1H, m), 6.7-6.9 (2H, m), 6.9-7.1 (2H, m), 7.1-7.4 (6H,m), 7.7-7.9 (2H,m); MS m/z 284 (M of SM+3).

EXAMPLE 216

4-(5-Pentylamino-5,6,7,8-tetrahydro-napthalen-2-yloxy)-benzamide

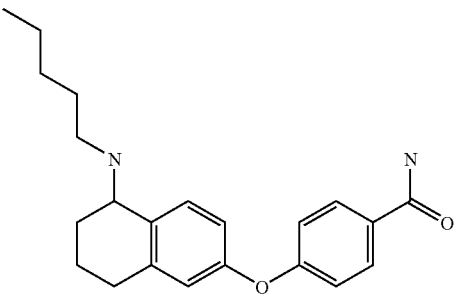

Using a method similar to Example 212, using Pentylamine (75 uL, 0.64 mmol) gives 73.6 mg (49% yield) of the title compound: $^1$H NMR (500 MHz, CDCl$_3$); 0.8-1.0 (3H, m), 1.2-1.4 (4H, m), 1.4-1.6 (2H, m), 1.6-1.8 (1H, m), 1.8-2.0 (3H, m), 2.6-2.9 (4H, m), 3.7-3.8 (1H, m),6.1-6.4 (2H, br s), 6.7-6.9 (2H,m), 6.9-7.1 (2H, m), 7.2-7.4 (1H, m), 7.7-7.9 (2H,m); MS m/z 284 (M of SM+3).

EXAMPLE 217

4-[5-(4-Methyl-cyclohexylamino)-5,6,7,8-tetrahydro-naphthalen-2-yloxy]-benzamide

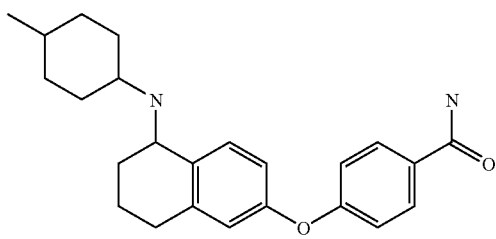

Using a method similar to Example 212, using 4-Methyl-cyclohexylamine (85 uL, 0.64 mmol) gives 95.0 mg (58% yield) of the title compound: $^1$H NMR (500 MHz, CDCl$_3$); 0.9-1.2 (6H, m), 1.3-1.6 (4H, m), 1.6-2.0 (7H, m), 2.6-3.0 (3H, m), 3.8-3.9 (1H, m), 6.2-6.4 (2H, br s), 6.7-7.0 (4H, m), 7.3-7.4 (1H,m), 7.7-7.9 (2H,m); MS m/z 284 (M of SM+3).

EXAMPLE 218

6-[5-(2-Phenyl-propylamino)-5,6,7,8-tetrahydro-naphthalen-2-yloxy]-nicotinamide

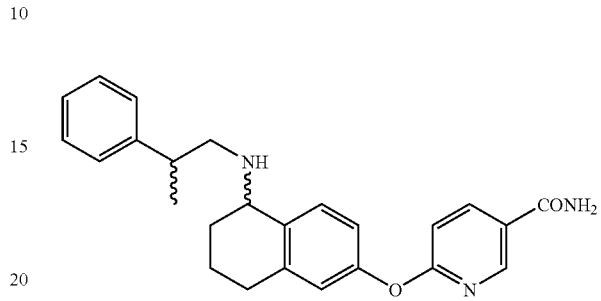

Prepared according to General Procedure IV using intermediate 2 and 2-methyl-phenethylamine, to afford a 50% yield.

$^1$H NMR (MeOD-d$_4$) δ: 8.56 (d, 1H, J=2.4 Hz), 8.17 (dd, 1H, J=8.6, 2.4 Hz), 7.40-7.10 (m, 5H), 7.02-6.75 (m, 4H), 3.80-3.90 (m, 1H), 3.00-2.90 (m, 3H), 2.70-2.60 (m, 2H), 1.95-1.60 (m, 4H), 1.30 (m, 4H).

$^{13}$C NMR (MeOD-d$_4$) δ: 167.2, 164.8, 164.7, 151.2, 151.1, 146.4, 143.9, 143.8, 138.5, 138.4, 138.3, 134.3, 134.2, 128.7, 128.4, 127.4, 126.0, 125.9, 125.3, 123.6, 120.1, 119.9, 117.4, 117.3, 109.3, 54.1, 53.0, 52.8, 51.5, 38.9, 38.5, 28.0, 27.9, 26.6, 26.2, 18.4, 18.3, 17.6, 17.3.

MS (Electrospray): 402.2 (M$^+$+1).

EXAMPLE 219

6-[5-(2-Hydroxy-2-phenyl-ethylamino)-5,6,7,8-tetrahydro-naphthalen-2-yloxy]-nicotinamide

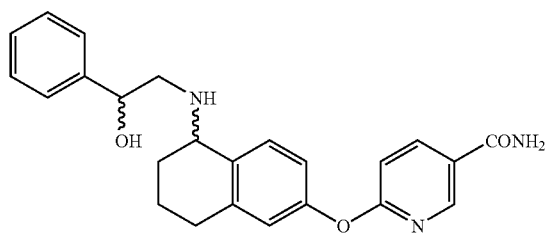

To a solution of the silyl derivative (Intermediate 34) in THF a solution 1M of tetrabutylammonium fluoride is added. The resulting solution is stirred overnight. Water and ethyl acetate is added. The aqueous layer is extracted with additional ethyl acetate. The combined organic phase was dried and evaporated to yield a crude which was purified by column chromatography.

98% Yield.

$^1$H NMR (MeOD-d$_4$) δ: 8.56 (d, 1H, J=2.4 Hz), 8.17 (dd, 1H, J=8.5, 2.4 Hz), 7.55-7.25 (m, 6H), 7.02-6.80 (m, 3H), 4.00-3.80 (m, 1H), 3.00-2.60 (m, 4H), 2.00-1.60 (m, 6H).

$^{13}$C NMR (MeOD-d$_4$) δ: 168.1, 165.7, 152.2, 147.3, 143.2, 139.5, 139.3, 135.1, 129.7, 127.9, 127.1, 125.6, 124.5, 121.0, 120.9, 118.4, 110.3, 72.6, 71.8, 54.9, 54.4, 53.9, 53.5, 28.9, 27.7, 27.5, 18.4, 18.2.

MS (Electrospray): 404.2 (M$^+$+1).

EXAMPLE 220

6-(6-Benzylamino-6,7,8,9-tetrahydro-5H-benzocyclohepten-2-yloxy)-nicotinamide

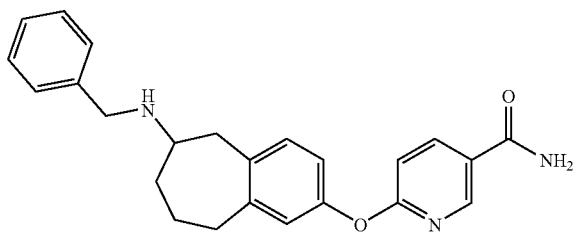

A solution of Intermediate 37 (30 mg, 0.08 mmol) in DMSO (0.5 mL) is treated with $K_2CO_3$ (15 mg, 0.11 mmol) and 6-chloronicotinamide (13 mg, 0.08 mmol). The reaction mixture is heated to 100° C. for 6 hours, then cooled to room temperature and poured into 25 mL $CH_2Cl_2$. The organics are washed with 25 mL water, 25 mL brine, then dried over $MgSO_4$ and evaporated to give 30 mg crude material. This material is partially purified by flash chromatography using 2:1 ethyl acetate/hexanes as solvent to give 8 mg of product contaminated with 6-chloronicotinamide. The product was dissolved in 1 mL $CH_2Cl_2$ and treated with 20 uL of trifluoroacetic acid. After 2 hours, an additional 20 uL of trifluoroacetic acid was added and the reaction was stirred overnight. The reaction mixture was then diluted with methanol and poured onto a 500 mg strong cation exchange column. The column was washed with methanol, and the product was eluted with 2N ammonia/methanol. Evaporation of the eluent gave 4.5 mg final product, or 14% yield from intermediate 37.

EXAMPLE 221

6-(6-Phenethylamino-6,7,8,9-tetrahydro-5H-benzocyclohepten-2-yloxy)-nicotinamide

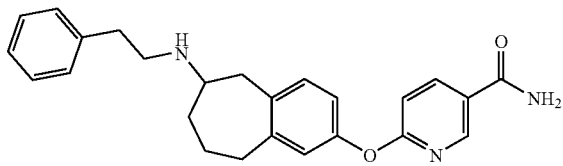

The compound is prepared analogously to example 220 starting from intermediate 38 to give 6.7 mg product, 21% yield.

EXAMPLE 222

6-[2-(2-Cyclohexyl-ethylamino)-indan-5-yloxy]-nicotinamide

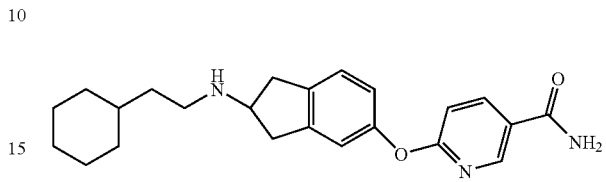

The above compound is prepared according to general Procedure V using Intermediate 15 and cyclohexane-acetaldehyde.

MS ES$^+$ (M+H)$^+$ 380.

$^1$H-NMR (CDCl$_3$, 400 MHz): 8.55 (d, J=2.44 Hz, 1H), 8.15 (dd, 1H, J=7.8, 2.44 Hz), 7.20 (d, J=8.3 Hz, 1H), 6.87-6.94 (m, 3H), 3.67 (p, J=6.84 Hz, 1H), 3.17 (m, 2H), 2.66-2.83 (m, 4H), 0.89-1.69 (m, 13H).

EXAMPLE 223

6-[2-(2-Cyclopentyl-ethylamino)-indan-5-yloxy]-nicotinamide

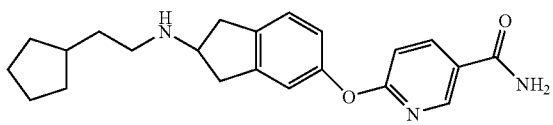

The above compound is prepared according to General Procedure V using Intermediate 15 and cyclopentane-acetaldehyde.

MS ES$^+$ (M+H)$^+$.

$^1$H-NMR (CDCl$_3$, 400 MHz): 8.57 (d, J=2.44 Hz, 1H), 8.15 (dd, 1H, J=2.44, 8.30 Hz), 7.20 (d, J=8.3 Hz, 1H), 6.88-6.95 (m, 3H), 3.68 (m, 1H), 3.18 (m, 2H), 2.66-2.84 (m, 4H), 1.10-1.79 (m, 11H).

EXAMPLES 224-246

| Example | Serial # | IUPAC name | General Procedure | Intermediate # | Reagent | Mass (pos. ion) |
|---|---|---|---|---|---|---|
| 224 | 2073577 | 6-[2-(Cyclopropylmethyl-amino)-indan-5-yloxy]-nicotinamide | V | 15 | cyclopropane carboxaldehyde | 342 |
| 225 | 2073578 | 6-(2-Isobutylamino-indan-5-yloxy)-nicotinamide | V | 15 | isobutyraldehyde | 326 |
| 226 | 2073579 | 6-(2-Butylamino-indan-5-yloxy)-nicotinamide | V | 15 | butyraldehyde | 326 |

-continued

| Example | Serial # | IUPAC name | General Procedure | Intermediate # | Reagent | Mass (pos. ion) |
|---|---|---|---|---|---|---|
| 227 | 2073580 | 6-[2-(2-Methyl-butylamino)-indan-5-yloxy]-nicotinamide | V | 15 | 2-methylbutyraldehyde | 340 |
| 228 | 2073581 | 6-[2-(3-Hydroxy-butylamino)-indan-5-yloxy]-nicotinamide | V | 15 | 3-hydroxybutyraldehyde | 342 |
| 229 | 2073582 | 6-[2-(Cyclopentylmethyl-amino)-indan-5-yloxy]-nicotinamide | V | 15 | cyclopentane carboxaldehyde | 352 |
| 230 | 2073583 | 6-[2-(2-Ethyl-butylamino)-indan-5-yloxy]-nicotinamide | V | 15 | 2-ethylbutyraldehyde | 354 |
| 231 | 2073584 | 6-[2-(2-Methyl-pentylamino)-indan-5-yloxy]-nicotinamide | V | 15 | 2-methylpentanal | 354 |
| 232 | 2073585 | 6-(2-Hexylamino-indan-5-yloxy)-nicotinamide | V | 15 | hexanal | 354 |
| 233 | 2073586 | 6-[2-(5-Hydroxy-pentylamino)-indan-5-yloxy]-nicotinamide | V | 15 | 5-hydroxypnetanal | 356 |
| 234 | 2073588 | 6-{2-[(Cyclohex-3-enylmethyl)-amino]-indan-5-yloxy}-nicotinamide | V | 15 | 3-cyclohexene-1-carboxaldehyde | 364 |
| 235 | 2073590 | 6-[2-(Cyclohexylmethyl-amino)-indan-5-yloxy]-nicotinamide | V | 15 | cyclohexane carboxaldehyde | 366 |
| 236 | 2073592 | 6-{2-[(Bicyclo[2.2.1]hept-5-en-2-ylmethyl)-amino]-indan-5-yloxy}-nicotinamide | V | 15 | norbornen-5-al | 376 |
| 237 | 2073593 | 6-[2-(4,4,4-Trifluoro-butylamino)-indan-5-yloxy]-nicotinamide | V | 15 | 4,4,4-trifluorobutyraldehyde | 380 |
| 238 | 2073594 | 6-[2-(3,5,5-Trimethyl-hexylamino)-indan-5-yloxy]-nicotinamide | V | 15 | 3,5,5-trimethylhexanal | 396 |
| 239 | 2073595 | 6-[2-(3-Phenyl-butylamino)-indan-5-yloxy]-nicotinamide | V | 15 | 3-methyl-3-phenyl-propionaldehyde | 402 |
| 240 | 2073596 | 6-[2-(2-Benzyloxy-ethylamino)-indan-5-yloxy]-nicotinamide | V | 15 | benzyloxyacetaldehyde | 404 |
| 241 | 2073598 | 6-{2-[3-(5-Methyl-furan-2-yl)-butylamino]-indan-5-yloxy}-nicotinamide | V | 15 | 3-(5-methyl-2-furyl)-butyraldehyde | 406 |
| 242 | 2073600 | 6-(2-Decylamino-indan-5-yloxy)-nicotinamide | V | 15 | decanal | 410 |
| 243 | 2073601 | 6-{2-[3-(4-Isopropyl-phenyl)-2-methyl-propylamino]-indan-5-yloxy}-nicotinamide | V | 15 | 3-(4-isopropylphenyl)-isobutyraldehyde | 444 |
| 244 | 2073603 | 6-[2-(3-Benzo[1,3]dioxol-5-yl-2-methyl- | V | 15 | 2-methyl-3-(3,4-methylenedioxyphenyl)-propanal | 446 |

| Example | Serial # | IUPAC name | General Procedure | Intermediate # | Reagent | Mass (pos. ion) |
|---|---|---|---|---|---|---|
| | | propylamino)-indan-5-yloxy]-nicotinamide | | | | |
| 245 | 2073605 | 6-[2-(2,2-Diphenyl-ethylamino)-indan-5-yloxy]-nicotinamide | V | 15 | diphenyl-acetaldehyde | 450 |
| 246 | 2076993 | 6-[2-(2-Cyclohexyl-ethylamino)-indan-5-yloxy]-nicotinamide | V | 15 | cyclohexyl-acetaldehyde | 380 |

EXAMPLE 247

6-{2-[(3-Methyl-butylamino)-methyl]-indan-5-yloxy}-nicatinamide

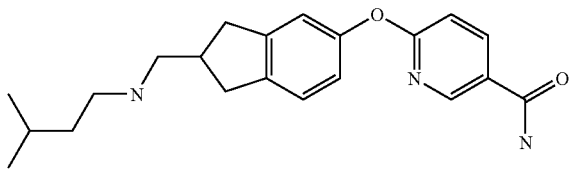

Combine 6-(2-Formyl-indan-5-yloxy)-nicotinamide (Intermediate 32, 25.3 mg, 0.09 mmol), MeOH (2.4 mL), trimethylorthoformate (1.6 mL), and isopentyl amine (9 uL, 0.08 mmol). After the reaction stirs at room temperature under a nitrogen atmosphere for 4.5 hours, add NaBH$_4$ (4.1 mg, 0.11 mmol), then stir at room temperature for another 12 hours. After that time, concentrate under reduced pressure then add ethyl acetate. Wash the organic phase with water, brine, and dry over Na$_2$SO$_4$. After concentration under reduced pressure the mixture, add to a 2 g SCX column, wash with MeOH and elute with 1N NH$_3$-MeOH. After concentration, flash chromatograph using 2% 1N NH$_3$-MeOH, 20% THF, 38% DCM to afford 7.0 mg, 0.02 mmol (25% yield) of the title compound: $^1$H NMR (500 MHz, d-Methanol); 0.9 (6H, d), 1.4-1.5 (2H, m), 1.6-1.7 (1H, m), 2.6-2.8 (6H, m), 3.1-3.2 (2H, m), 3.3-3.4 (1H, m), 6.8 (1H, d), 6.9 (1H, s), 7.1 (1H, d), 7.2 (1H, s), 8.1 (1H, d), 8.5 (1H, s); TLC 2% 1N NH$_3$-MeOH:20% THF:78% CH$_2$Cl$_2$: R$_f$=0.27.

EXAMPLE 248

6-[2-(3-Phenethylamino-methyl)-indan-5-yloxy]-nicotinamide

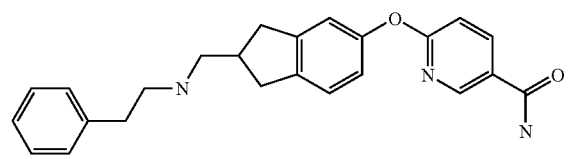

Using a method similar to Example 247, using Phenethylamine (20 uL, 0.16 mmol) gives 17.0 mg (27% yield) of the title compound: $^1$H NMR (500 MHz, CDCl$_3$); 2.6-3.2 (12H, d), 6.8-7.0 (3H, m), 7.1-7.4 (7H, m), 7.9 (1H, d), 8.5 (1H, s); TLC 2% 1N NH$_3$-MeOH:20% THF:78% CH$_2$Cl$_2$: R$_f$=0.31.

EXAMPLE 249

6-[2-(Benzylamino)-methyl]-indan-5-yloxy]-nicotinamide

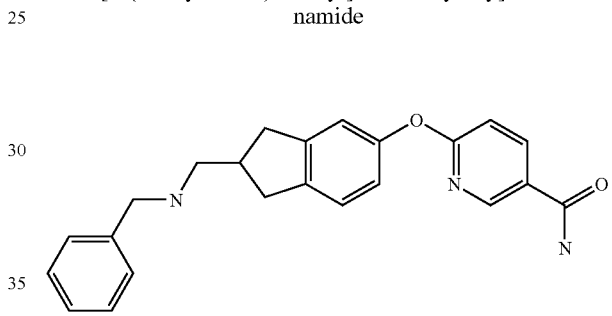

Using a method similar to Example 247, using Benzylamine (22 uL, 0.20 mmol) gives 41.7 mg (56% yield) of the title compound: $^1$H NMR (500 MHz, CDCl$_3$); 2.6-2.8 (5H, m), 3.0-3.2 (2H, m), 3.8 (2H, s), 6.8-7.0 (3H, m), 7.2-7.4 (6H, m), 7.9 (1H, d), 8.5 (1H, s); TLC 2% 1N NH$_3$-MeOH:20% THF:78% CH$_2$Cl$_2$: R$_f$=0.43

We claim:
1. A compound selected from the group consisting of:
   6-(8-Pentylamino-5,6,7,8-tetrahydro-naphthalen-2-yloxy)-nicotinamide,
   6-(5-Pentylamino-5,6,7,8-tetrahydro-naphthalen-2-yloxy)-nicotinamide,
   6-(5-Pentylamino-5,6,7,8-tetrahydro-naphthalen-1-yloxy)-nicotinamide,
   6-(1-Pentylamino-indan-5-yloxy)-nicotinamide,
   6-(1-Pentylamino-indan-4-yloxy)-nicotinamide,
   6-(8-Benzylamino-5,6,7,8-tetrahydro-naphthalen-2-yloxy)-nicotinamide,
   6-(5-Benzylamino-5,6,7,8-tetrahydro-naphthalen-2-yloxy)-nicotinamide,
   6-(5-Benzylamino-5,6,7,8-tetrahydro-naphthalen-1-yloxy)-nicotinamide,
   6-(1-Benzylamino-indan-4-yloxy)-nicotinamide,
   6-(8-Phenethylamino-5,6,7,8-tetrahydro-naphthalen-2-yloxy)-nicotinamide,
   6-(5-Phenethylamino-5,6,7,8-tetrahydro-naphthalen-2-yloxy)-nicotinamide,
   6-(5-Phenethylamino-5,6,7,8-tetrahydro-naphthalen-1-yloxy)-nicotinamide,

6-(1-Phenethylamino-indan-4-yloxy)-nicotinamide,
6-{8-[2-(3-Fluoro-phenyl)-ethylamino]-5,6,7,8-tetrahydro-naphthalen-2-yloxy}-nicotinamide, or a pharmaceutically acceptable salt or solvate thereof.

2. A pharmaceutical composition comprising a therapeutically effective amount of a compound of clam 1 association with a carrier, diluent and/or excipient.

* * * * *